(12) United States Patent
Grenon et al.

(10) Patent No.: US 10,278,587 B2
(45) Date of Patent: May 7, 2019

(54) EYELID ILLUMINATION SYSTEMS AND METHOD FOR IMAGING MEIBOMIAN GLANDS FOR MEIBOMIAN GLAND ANALYSIS

(71) Applicant: TEARSCIENCE, INC., Morrisville, NC (US)

(72) Inventors: Stephen M. Grenon, Morrisville, NC (US); Donald R. Korb, Boston, MA (US); Joshua Grenon, Morrisville, NC (US); Scott Liddle, Morrisville, NC (US); Steve Bacich, Half Moon Bay, CA (US); John M. Jans, Hillsborough, NC (US)

(73) Assignee: TearScience, Inc., Morrisville, NC (US)

( * ) Notice: Subject to any disclaimer, the term of this patent is extended or adjusted under 35 U.S.C. 154(b) by 16 days.

(21) Appl. No.: 14/269,646

(22) Filed: May 5, 2014

(65) Prior Publication Data
US 2014/0330129 A1   Nov. 6, 2014

Related U.S. Application Data

(60) Provisional application No. 61/987,982, filed on May 2, 2014, provisional application No. 61/819,143, filed on (Continued)

(51) Int. Cl.
*A61B 5/00* (2006.01)

(52) U.S. Cl.
CPC .......... *A61B 5/0082* (2013.01); *A61B 5/0077* (2013.01); *A61B 5/6821* (2013.01)

(58) Field of Classification Search
None
See application file for complete search history.

(56) References Cited

U.S. PATENT DOCUMENTS

| 3,909,771 A | 9/1975 | Pickering et al. |
| 3,941,901 A | 3/1976 | Harsch |

(Continued)

FOREIGN PATENT DOCUMENTS

| CN | 101663064 A | 3/2010 |
| CN | 202891897 U | 4/2013 |

(Continued)

OTHER PUBLICATIONS

Pflugfelder et al. 1998 Cornea. 1998 17:38-56.*

(Continued)

*Primary Examiner* — Baisakhi Roy
*Assistant Examiner* — Patrick M Mehl
(74) *Attorney, Agent, or Firm* — Withrow & Terranova, P.L.L.C.

(57) ABSTRACT

Eyelid illumination systems and methods for imaging meibomian glands for meibomian gland analysis are disclosed. In one embodiment, a patient's eyelid is IR trans-illuminated with an infrared (IR) light. A trans-illumination image of the patient's eyelid is captured showing meibomian glands in dark outlined areas, whereas non-gland material is shown in light areas. This provides a high contrast image of the meibomian glands that is X-ray like. The lid trans-illumination image of the meibomian glands can be analyzed to determine to diagnose the meibomian glands in the patient's eyelid. The eyelid may be trans-illuminated by a lid-flipping device configured to grasp and flip the eyelid for imaging the interior surface of the eyelid. Also, an IR surface meibography image of the meibomian glands may also be captured and combined with the trans-illumination image of the meibomian glands to provide a higher contrast image of the meibomian glands.

24 Claims, 30 Drawing Sheets
(5 of 30 Drawing Sheet(s) Filed in Color)

Related U.S. Application Data on May 3, 2013, provisional application No. 61/819,201, filed on May 3, 2013, provisional application No. 61/904,562, filed on Nov. 15, 2013.

(56) References Cited

U.S. PATENT DOCUMENTS

| | | |
|---|---|---|
| RE28,873 E | 6/1976 | Morgan |
| 3,971,952 A | 7/1976 | Inbar et al. |
| 4,122,348 A | 10/1978 | Bruck |
| 4,261,364 A | 4/1981 | Haddad et al. |
| 4,274,421 A | 6/1981 | Dory |
| 4,533,223 A | 8/1985 | Duparchy |
| 4,567,898 A | 2/1986 | Plugge et al. |
| 4,584,880 A | 4/1986 | Matzuk |
| 4,588,883 A * | 5/1986 | Abbas ................ G06K 15/1247 250/205 |
| 4,597,648 A | 7/1986 | Feldon et al. |
| 4,705,037 A | 11/1987 | Peyman et al. |
| 4,747,683 A | 5/1988 | Doane |
| 4,842,401 A | 6/1989 | Maurice |
| 4,885,352 A | 12/1989 | Erickson |
| 4,938,584 A | 7/1990 | Suematsu et al. |
| 5,110,200 A | 5/1992 | Snook |
| 5,137,355 A | 8/1992 | Barbour et al. |
| D330,769 S | 11/1992 | Blaha et al. |
| 5,216,456 A | 6/1993 | Volk |
| 5,258,791 A | 11/1993 | Penney et al. |
| 5,268,305 A | 12/1993 | Ribi et al. |
| 5,427,915 A | 6/1995 | Ribi et al. |
| 5,475,452 A | 12/1995 | Kuhn et al. |
| 5,491,097 A | 2/1996 | Ribi et al. |
| 5,494,829 A | 2/1996 | Sandstrom et al. |
| 5,557,351 A | 9/1996 | Kasahara et al. |
| 5,571,568 A | 11/1996 | Ribi et al. |
| 5,621,523 A | 4/1997 | Oobayashi et al. |
| 5,622,872 A | 4/1997 | Ribi |
| 5,625,428 A | 4/1997 | Isogai |
| 5,626,134 A | 5/1997 | Zuckerman |
| 5,642,137 A | 6/1997 | Kitazumi |
| 5,647,032 A | 7/1997 | Jutamulia |
| 5,712,721 A | 1/1998 | Large |
| 5,719,659 A | 2/1998 | Suzuki |
| D394,505 S | 5/1998 | Hayashi |
| 5,760,950 A | 6/1998 | Maly et al. |
| 5,886,767 A | 3/1999 | Snook |
| 5,958,912 A | 9/1999 | Sullivan et al. |
| 5,988,815 A | 11/1999 | Maus et al. |
| 5,993,391 A | 11/1999 | Kamiyama |
| 6,024,095 A | 2/2000 | Stanley, III |
| 6,059,773 A | 5/2000 | Maloney et al. |
| 6,072,180 A | 6/2000 | Kramer et al. |
| 6,088,470 A | 7/2000 | Camus et al. |
| 6,107,289 A | 8/2000 | Sullivan |
| 6,127,183 A | 10/2000 | Ivarsson et al. |
| 6,153,607 A | 11/2000 | Pflugfelder et al. |
| 6,198,540 B1 | 3/2001 | Ueda et al. |
| 6,213,605 B1 | 4/2001 | D'Souza et al. |
| 6,228,029 B1 | 5/2001 | Eccardt et al. |
| 6,236,459 B1 | 5/2001 | Negahdaripour |
| 6,299,305 B1 | 10/2001 | Miwa |
| 6,394,603 B2 | 5/2002 | Miwa et al. |
| 6,419,361 B2 | 7/2002 | Cabib et al. |
| 6,447,119 B1 | 9/2002 | Stewart et al. |
| 6,450,641 B2 | 9/2002 | D'Souza et al. |
| 6,455,583 B1 | 9/2002 | Pflugfelder et al. |
| D465,850 S | 11/2002 | Takizawa |
| 6,500,123 B1 | 12/2002 | Holloway et al. |
| D472,637 S | 4/2003 | Cooper et al. |
| 6,556,853 B1 | 4/2003 | Cabib et al. |
| 6,613,041 B1 | 9/2003 | Schründer |
| 6,659,613 B2 | 12/2003 | Applegate et al. |
| 6,685,320 B2 | 2/2004 | Hirohara et al. |
| 6,736,507 B2 | 5/2004 | Kudryashov et al. |
| 6,743,249 B1 | 6/2004 | Alden |
| 6,949,071 B1 | 9/2005 | Saied et al. |
| 6,964,814 B2 | 11/2005 | Fujii et al. |
| 7,060,061 B2 | 6/2006 | Altshuler et al. |
| 7,073,906 B1 | 7/2006 | Portney |
| 7,111,980 B2 | 9/2006 | Pavlidis et al. |
| 7,118,217 B2 | 10/2006 | Kardon et al. |
| 7,121,666 B2 | 10/2006 | Tseng et al. |
| 7,144,111 B1 | 12/2006 | Ross, III et al. |
| D552,736 S | 10/2007 | Yamaoka |
| 7,278,740 B1 | 10/2007 | Suzuki et al. |
| 7,281,801 B2 | 10/2007 | Wang |
| 7,431,458 B2 | 10/2008 | Jongsma et al. |
| D582,556 S | 12/2008 | Yamaoka |
| 7,611,245 B2 | 11/2009 | Carbonari |
| D607,562 S | 1/2010 | Heine et al. |
| 7,654,669 B2 | 2/2010 | Suzuki |
| 7,688,453 B2 | 3/2010 | Williby et al. |
| D614,774 S | 4/2010 | Gausmann et al. |
| 7,758,190 B2 | 7/2010 | Korb et al. |
| 7,771,353 B2 | 8/2010 | Luce |
| 7,982,881 B2 | 7/2011 | Fercher et al. |
| 7,988,294 B2 | 8/2011 | Korb et al. |
| 8,092,023 B2 | 1/2012 | Korb et al. |
| 8,192,026 B2 | 6/2012 | Gravely et al. |
| 8,215,774 B2 | 7/2012 | Korb et al. |
| 8,249,695 B2 | 8/2012 | Grenon et al. |
| 8,255,039 B2 | 8/2012 | Gravely et al. |
| 8,545,017 B2 | 10/2013 | Korb et al. |
| 8,585,204 B2 | 11/2013 | Gravely et al. |
| 8,591,033 B2 | 11/2013 | Korb et al. |
| 8,602,557 B2 | 12/2013 | Huth et al. |
| 8,610,976 B1 * | 12/2013 | Cook .................. G06T 5/50 358/463 |
| 8,617,229 B2 | 12/2013 | Korb et al. |
| 8,641,194 B2 | 2/2014 | Primeau et al. |
| 8,746,883 B2 | 6/2014 | Korb et al. |
| 8,888,286 B2 | 11/2014 | Grenon et al. |
| 8,915,592 B2 | 12/2014 | Korb et al. |
| 9,173,558 B2 | 11/2015 | Huth et al. |
| 9,456,741 B2 | 10/2016 | Huth et al. |
| 2001/0055095 A1 | 12/2001 | D'Souza et al. |
| 2002/0039234 A1 | 4/2002 | Iwamoto |
| 2002/0049374 A1 | 4/2002 | Abreu |
| 2002/0180929 A1 | 12/2002 | Tseng et al. |
| 2003/0018271 A1 | 1/2003 | Kimble |
| 2003/0056281 A1 | 3/2003 | Hasegawa |
| 2003/0067249 A1 | 4/2003 | Lockwood et al. |
| 2003/0069489 A1 | 4/2003 | Abreu |
| 2003/0114426 A1 | 6/2003 | Pflugfelder et al. |
| 2003/0195438 A1 | 10/2003 | Petillo |
| 2003/0211043 A1 | 11/2003 | Korb |
| 2003/0233135 A1 | 12/2003 | Yee |
| 2004/0001203 A1 | 1/2004 | Simpson |
| 2004/0212781 A1 | 10/2004 | Mihashi et al. |
| 2004/0238969 A1 | 12/2004 | Chen |
| 2005/0096431 A1 | 5/2005 | Fujii et al. |
| 2005/0119737 A1 | 6/2005 | Bene et al. |
| 2005/0159657 A1 | 7/2005 | Cappo et al. |
| 2005/0203421 A1 | 9/2005 | Zeng et al. |
| 2006/0055956 A1 | 3/2006 | Takahashi et al. |
| 2006/0103724 A1 | 5/2006 | Jongsma et al. |
| 2006/0106283 A1 | 5/2006 | Wallace et al. |
| 2006/0109423 A1 | 5/2006 | Wang |
| 2006/0140454 A1 | 6/2006 | Northcott et al. |
| 2006/0159722 A1 | 7/2006 | Braithwaite et al. |
| 2006/0173360 A1 | 8/2006 | Kalafut et al. |
| 2006/0187462 A1 | 8/2006 | Srinivasan et al. |
| 2006/0223032 A1 | 10/2006 | Fried et al. |
| 2006/0234071 A1 | 10/2006 | Friz et al. |
| 2006/0270802 A1 | 11/2006 | Washizu et al. |
| 2008/0002202 A1 | 1/2008 | Hall et al. |
| 2008/0081996 A1 * | 4/2008 | Grenon .................. A61B 3/10 600/443 |
| 2008/0081999 A1 * | 4/2008 | Gravely .................. A61B 3/10 600/473 |
| 2008/0161741 A1 | 7/2008 | Bene et al. |
| 2008/0273171 A1 | 11/2008 | Huth et al. |
| 2008/0285043 A1 | 11/2008 | Fercher et al. |
| 2008/0287808 A1 | 11/2008 | Tearney et al. |
| 2008/0309855 A1 | 12/2008 | Yan et al. |

(56) References Cited

U.S. PATENT DOCUMENTS

| | | |
|---|---|---|
| 2008/0316499 A1 | 12/2008 | Korb et al. |
| 2008/0319323 A1 | 12/2008 | Gravely et al. |
| 2009/0161090 A1 | 6/2009 | Campbell et al. |
| 2009/0201465 A1 | 8/2009 | Huth |
| 2009/0225276 A1 | 9/2009 | Suzuki |
| 2009/0275929 A1 | 11/2009 | Zickler |
| 2010/0026323 A1 | 2/2010 | Tiefenthaler |
| 2010/0085540 A1 | 4/2010 | Korb et al. |
| 2010/0102211 A1 | 4/2010 | Murooka et al. |
| 2010/0253907 A1 | 10/2010 | Korb et al. |
| 2010/0259721 A1 | 10/2010 | Korb et al. |
| 2010/0297193 A1 | 11/2010 | Archambeau et al. |
| 2010/0315591 A1 | 12/2010 | Gratton et al. |
| 2011/0007321 A1 | 1/2011 | Everett et al. |
| 2011/0043661 A1 | 2/2011 | Podoleanu |
| 2011/0053283 A1 | 3/2011 | Hood et al. |
| 2011/0096292 A1 | 4/2011 | Saito |
| 2011/0181836 A1 | 7/2011 | Rowe |
| 2011/0206291 A1 | 8/2011 | Kashani et al. |
| 2011/0237999 A1 | 9/2011 | Muller et al. |
| 2011/0273550 A1 | 11/2011 | Amano et al. |
| 2011/0292395 A1 | 12/2011 | Fercher et al. |
| 2012/0188508 A1 | 7/2012 | Kim et al. |
| 2012/0226156 A1 | 9/2012 | Grenon et al. |
| 2013/0010257 A1 | 1/2013 | Primeau et al. |
| 2013/0050647 A1 | 2/2013 | Steinmueller |
| 2013/0058550 A1* | 3/2013 | Tanimoto ............ G01N 21/9508 382/128 |
| 2013/0141698 A1 | 6/2013 | Huth et al. |
| 2013/0169933 A1 | 7/2013 | Wang |
| 2013/0172829 A1 | 7/2013 | Badawi |
| 2013/0208495 A1* | 8/2013 | Dau ...................... F21V 7/0008 362/551 |
| 2013/0293842 A1 | 11/2013 | Grenon et al. |
| 2013/0308095 A1 | 11/2013 | Korb et al. |
| 2014/0016093 A1 | 1/2014 | Korb et al. |
| 2014/0028979 A1 | 1/2014 | De Juan, Jr. et al. |
| 2014/0104574 A1 | 4/2014 | Grenon et al. |
| 2014/0118699 A1 | 5/2014 | Huth et al. |
| 2014/0363064 A1 | 12/2014 | Lee et al. |
| 2015/0141837 A1 | 5/2015 | Arita et al. |
| 2015/0351626 A1 | 12/2015 | Huth et al. |
| 2015/0351627 A1 | 12/2015 | Huth et al. |
| 2015/0351628 A1 | 12/2015 | Huth et al. |
| 2017/0265739 A1 | 9/2017 | Korb et al. |
| 2017/0280991 A1 | 10/2017 | Huth et al. |
| 2017/0280992 A1 | 10/2017 | Huth et al. |
| 2018/0001108 A1 | 1/2018 | Kelleher |

FOREIGN PATENT DOCUMENTS

| | | | |
|---|---|---|---|
| CN | 103799976 A | 5/2014 | |
| DE | 3108878 A1 | 9/1982 | |
| EP | 0943288 A1 | 9/1999 | |
| EP | 1900320 A1 | 3/2008 | |
| EP | 2189108 A1 | 5/2010 | |
| EP | 2695570 A1 | 2/2014 | |
| EP | 1900320 B1 | 4/2014 | |
| EP | 3015107 A1 | 5/2016 | |
| GB | 2407378 B | 9/2006 | |
| JP | 6269412 A | 9/1994 | |
| JP | 7002647 A | 1/1995 | |
| JP | 7136120 A | 5/1995 | |
| JP | H07136120 A | 5/1995 | |
| JP | 07313464 A | 12/1995 | |
| JP | 07313465 A | 12/1995 | |
| JP | 8052112 A | 2/1996 | |
| JP | 8098811 A | 4/1996 | |
| JP | H09201334 A | 8/1997 | |
| JP | 2000262468 A | 9/2000 | |
| JP | 2001309889 A | 11/2001 | |
| JP | 2002515593 A | 5/2002 | |
| JP | 2004236727 A | 8/2004 | |
| JP | 2004536653 A | 12/2004 | |
| JP | 2005211173 A | 8/2005 | |
| JP | 2005211633 A | 8/2005 | |
| JP | 2005230328 A | 9/2005 | |
| JP | 2006198249 A | 8/2006 | |
| JP | 2007068928 A | 3/2007 | |
| JP | 2007209370 A | 8/2007 | |
| JP | 2007523382 A | 8/2007 | |
| JP | 2008246004 A | 10/2008 | |
| JP | 2009134276 A | 6/2009 | |
| JP | 3168993 U | 7/2011 | |
| JP | 5748268 B2 | 7/2015 | |
| JP | 2016179098 A | 10/2016 | |
| JP | 2017012663 A | 1/2017 | |
| KR | 101259056 B1 | 4/2013 | |
| KR | 20160146220 A | 12/2016 | |
| KR | 101755630 B1 | 7/2017 | |
| WO | 9958131 A1 | 11/1999 | |
| WO | 9960331 A1 | 11/1999 | |
| WO | 0026614 A1 | 5/2000 | |
| WO | 03011135 A1 | 2/2003 | |
| WO | 2004041134 A1 | 5/2004 | |
| WO | 2005044099 A1 | 5/2005 | |
| WO | 2007004348 A1 | 1/2007 | |
| WO | 2008089327 A1 | 7/2008 | |
| WO | 2008137863 A2 | 11/2008 | |
| WO | 2008156883 A | 12/2008 | |
| WO | 2012137545 A1 | 10/2012 | |
| WO | 2013082356 A2 | 6/2013 | |
| WO | 2013082356 A3 | 6/2013 | |
| WO | 2013109193 A1 | 7/2013 | |
| WO | 2013166352 A2 | 11/2013 | |
| WO | 2013166477 A2 | 11/2013 | |
| WO | 2014018640 A1 | 1/2014 | |
| WO | 2015187315 A1 | 12/2015 | |
| WO | 2015187317 A1 | 12/2015 | |
| WO | 2016063130 A1 | 4/2016 | |
| WO | 2018004234 A1 | 1/2018 | |

OTHER PUBLICATIONS

Yokoi et al. 2007 Jpn.J.Ophtalmol. 51:53-56.*
Matsumoto et al. 2004 Jpn. J. Ophthalmol. 48:372-375.*
International Preliminary Report on Patentability for International Patent Application No. PCT/US2014/036636, dated Nov. 12, 2015, 8 pages.
International Preliminary Report on Patentability for International Patent Application No. PCT/US2014/036780, dated Nov. 12, 2015, 8 pages.
Notice of Rejection for Japanese Patent Application No. 2014-238420, dated Oct. 13, 2015, 4 pages.
Non-Final Office Action for U.S. Appl. No. 13/870,214, dated Nov. 10, 2015, 11 pages.
Hwang, Ho Sik et al., "Novel Tear Interferometer Made of Paper for Lipid Layer Evaluation," Cornea, vol. 33, Issue 8, Aug. 2014, pp. 826-831.
Third Office Action for Chinese Patent Application No. 201080024927.9, dated Nov. 26, 2014, 7 pages.
Examination Report for European Patent Application No. 08732520.5, dated Jul. 13, 2015, 6 pages.
International Preliminary Report on Patentability for International Patent Application No. PCT/US2013/077117, dated Jul. 2, 2015, 33 pages.
Third Office Action for Chinese Patent Application No. 201210500620.2, dated Jul. 27, 2015, 17 pages.
Non-Final Office Action for U.S. Appl. No. 14/299,504, dated Aug. 13, 2015, 14 pages.
Non-Final Office Action for U.S. Appl. No. 13/886,383, dated Jun. 25, 2015, 22 pages.
Oculus, "Oculus Keratograph 5M Der Revolutionär," Date Unknown, Oculus, 2 pages.
Non-Final Office Action for U.S. Appl. No. 14/543,583, dated Mar. 22, 2016, 17 pages.
Finis, D. et al., "Factors Influencing the Measurement of Tear Film Lipid Layer Thickness with Interferometry," Klin Monbl Augenheilkd, vol. 231, No. 6, Jun. 2014, pp. 603-610.

(56) References Cited

OTHER PUBLICATIONS

International Search Report and Written Opinion for PCT/US2014/065992, dated Mar. 3, 2015, 9 pages.
Second Office Action for Chinese Patent Application No. 201210500620.2, dated Mar. 30, 2015, 14 pages.
Micali, Jason D. et al., "Dynamic measurement of the corneal tear film with a Twyman-Green interferometer," Journal of Biomedical Optics, vol. 20, Issue 5, May 28, 2015, SPIE Digital Library, 6 pages.
Examination Report for European patent application 11183259.8 dated Mar. 23, 2015, 8 pages.
Examination Report for European patent application 10759411.1-1657 dated Mar. 23, 2015, 7 pages.
International Preliminary Report on Patentability for PCT/US2013/039395, dated Jun. 4, 2015, 10 pages.
Chan, Xiong, et al., "Influence of watching video display terminal on ocular surface and application of non-invasive ocular surface analyzer," Chinese Journal of Experimental Ophthalmology, vol. 34, Issue 5, May 2016, pp. 443-447 (Abstract).
Chan, Xiong, et al., "Influence of watching video display terminal on ocular surface and application of non-invasive ocular surface analyzer," Chinese Journal of Experimental Ophthalmology, vol. 34, Issue 5, May 2016, pp. 443-447 (Google Translation).
International Preliminary Report on Patentability for PCT/US2014/065992, dated May 26, 2016, 8 pages.
Decision to Grant for Japanese Patent Application No. 2014-238420, dated Jun. 7, 2016, 2 pages.
Notice of Preliminary Rejection for Korean Patent Application No. 10-2011-7026079, dated Apr. 28, 2016, 15 pages.
Corrected Notice of Allowance for U.S. Appl. No. 14/299,504, dated Jun. 30, 2016, 4 pages.
Non-Final Office Action for U.S. Appl. No. 13/325,586, dated Jun. 4, 2015, 11 pages.
Lam, Sin Man et al., "Longitudinal changes in tear fluid lipidome brought about by eyelid-warming treatment in a cohort of meibomian gland dysfunction," Journal of Lipid Research, vol. 55, No. 9, Sep. 2014, American Society for Biochemistry and Molecular Biology, Inc., pp. 1959-1969.
Szczesna, Dorota H. et al., "Application of interferometry for evaluation of the effect of contact lens material on tear film quality," Proceedings of SPIE, vol. 7064, Aug. 11, 2008, SPIE, 9 pages.
International Preliminary Report on Patentability for PCT/US2013/038116, dated Nov. 6, 2014, 11 pages.
International Preliminary Report on Patentability for PCT/US2013/038149, dated Nov. 6, 2014, 17 pages.
International Search Report and Written Opinion for PCT/US2014/036636, dated Oct. 2, 2014, 9 pages.
Office Action for Chinese Patent Application No. 201210500620.2, dated Sep. 3, 2014, 18 pages.
Corrected Notice of Allowability for U.S. Appl. No. 13/870,054 dated Nov. 14, 2014, 5 pages.
Corrected Notice of Allowability for U.S. Appl. No. 14/137,105, dated Sep. 25, 2014, 4 pages.
International Search Report and Written Opinion for PCT/US2014/036780, dated Nov. 13, 2014, 9 pages.
Fourth Office Action for Chinese Patent Application No. 201210500620.2, dated Dec. 31, 2015, 8 pages.
First Office Action and Examination Search Report for Canadian Patent Application No. 2,757,486, dated Dec. 22, 2015, 5 pages.
Notice of Allowance for U.S. Appl. No. 14/299,504, dated Feb. 3, 2016, 8 pages.
Notice of Allowance for U.S. Appl. No. 14/543,931, dated Jan. 11, 2016, 8 pages.
Extended European Search Report for European Patent Application No. 14792343.7, dated Nov. 16, 2016, 7 pages.
Second Office Action and Examination Search Report for Canadian Patent Application No. 2,757,486, dated Dec. 15, 2016, 7 pages.
Notice of Allowance for U.S. Appl. No. 15/143,834, dated Jan. 27, 2017, 8 pages.
Notice of Allowance for U.S. Appl. No. 15/152,624, dated Jan. 27, 2017, 7 pages.
Non-Final Office Action for U.S. Appl. No. 14/268,647, dated Dec. 12, 2016, 25 pages.
Arita, Reiko, et al., "Tear Interferometric Patterns Reflect Clinical Tear Dynamics in Dry Eye Patients," Investigative Ophthalmology & Visual Science, vol. 57, Issue 8, Jul. 2016, Association for Research in Vision and Ophthalmology Inc., pp. 3928-3934.
Micali, Jason D., et al., "Dual interferometer for dynamic measurement of corneal topography," Journal of Biomedical Optics, vol. 21, Issue 8, Aug. 31, 2016, SPIE, pp. 085007-1 to 085007-19.
Non-Final Office Action for U.S. Appl. No. 14/543,583, dated Sep. 13, 2016, 14 pages.
Notice of Allowance for U.S. Appl. No. 14/299,504, dated Sep. 16, 2016, 7 pages.
Non-Final Office Action for U.S. Appl. No. 15/143,834, dated Sep. 12, 2016, 5 pages.
Non-Final Office Action for U.S. Appl. No. 15/152,624, dated Sep. 27, 2016, 5 pages.
Notice of Allowance for U.S. Appl. No. 13/870,214, dated Dec. 2, 2016, 7 pages.
Extended European Search Report for European Patent Application No. 13864124.6, dated Jun. 24, 2016, 4 pages.
International Search Report and Written Opinion for International Patent Application No. PCT/US2008/057578, dated Aug. 26, 2008, 11 pages.
International Preliminary Report on Patentability for International Patent Application No. PCT/US2008/057578, dated Dec. 22, 2009, 11 pages.
International Search Report and Written Opinion for International Patent Application No. PCT/US2008/057581, dated Aug. 26, 2008, 11 pages.
International Preliminary Report on Patentability for International Patent Application No. PCT/US2008/057581, dated Dec. 22, 2009, 11 pages.
International Search Report and Written Opinion for International Patent Application No. PCT/US2010/029645, dated Jun. 4, 2010, 15 pages.
International Preliminary Report on Patentability for International Patent Application No. PCT/US2010/029645, dated Oct. 13, 2011, 12 pages.
Final Office Action for U.S. Appl. No. 13/870,214, dated Jul. 25, 2016, 12 pages.
Advisory Action for U.S. Appl. No. 14/543,583, dated May 11, 2017, 3 pages.
Notice of Allowance for U.S. Appl. No. 14/543,583, dated Jun. 12, 2017, 8 pages.
International Preliminary Report on Patentability for PCT/US2007/000505, dated Mar. 31, 2009, 5 pages.
First Office Action and Search Report for Chinese Patent Application No. 201480031610.6 dated May 2, 2017, 21 pages.
Karpecki, Paul M. et al., "Meibomian Gland Dysfunction (MGD) Treatment for the Relief of Evaporative Dry Eye Disease: A safety assessment of the iLux™ system on healthy volunteers," 8th International Conference on the Tear Film & Ocular Surface: Basic Science and Clinical Relevance, Conference Poster, Sep. 7-10, 2016, Montpellier, France, Tear Film Innovations, Inc., 1 page.
Examination Report for European Patent Application No. 14792343.7, dated Sep. 5, 2017, 5 pages.
Non-Final Office Action for U.S. Appl. No. 15/608,308, dated Sep. 5, 2017, 17 pages.
Non-Final Office Action for U.S. Appl. No. 15/615,244, dated Sep. 5, 2017, 6 pages.
Non-Final Office Action for U.S. Appl. No. 15/589,146, dated Sep. 18, 2017, 13 pages.
Notice of Allowance for U.S. Appl. No. 14/268,647, dated Aug. 28, 2017, 10 pages.
Notification of Reasons of Refusal for Japanese Patent Application No. 2016-512105, dated Apr. 10, 2018, 6 pages.
Notice of Allowance for U.S. Appl. No. 15/615,244, dated Feb. 6, 2018, 7 pages.
Notice of Allowance for U.S. Appl. No. 15/589,146, dated Feb. 12, 2018, 7 pages.

(56) References Cited

OTHER PUBLICATIONS

Notice of Allowance for U.S. Appl. No. 15/608,308, dated Feb. 16, 2018, 7 pages.
Hwang, Hyeonha et al., "Image-based quantitative analysis of tear film lipid layer thickness for meibomian gland evaluation," BioMedical Engineering Online, vol. 16, Dec. 2017, Springer, 15 pages.
Examination Report No. 1 for Standard Patent Application for Australian Patent Application No. 2014259619, dated Aug. 10, 2018, 4 pages.
Examination Report for European Patent Application No. 14792343.7, dated Aug. 21, 2018, 4 pages.
Examination Report Under Sections 12 & 13 of the Patents Act for Indian Patent Application No. 2026/MUMNP/2011, dated Oct. 5, 2018, 6 pages.
Author Unknown, "Tomey's RT-7000 is new and improved," Instruments—New Product Gallery, Vision Care Product News (VCPN), Jul. 2008, 1 page.
Author Unknown, "Tearscope Plus: Introduction and guided tour to the benefits of the Keeler Tearscope-plus," Keeler Instruments, bon Optic, created Jan. 24, 2006, www.bon.de/download/TearscopeE.pdf, 22 pages.
Australian Patent Examination Report No. 1 for Australian patent application 2011235961, dated Jan. 2, 2013, 3 pages.
Alonso-Caneiro, D. et al., "Context-Based Modelling of Interferometric Signals for the Assessment of Tear-Film Surface Quality," 2009 IEEE/SP 15th Workshop on Statistical Signal Processing (SSP), 2009, pp. 553-556.
An, Yang et al., "Contrast Sensitivity Measurement in Dry Eyes," Int J Ophthalmol, vol. 10, No. 3, Mar. 2010, pp. 488-491.
Arndt, G. Dickey et al., "Microwave Treatment of Prostate Cancer and Hyperplasia," NASA Tech Briefs, Jun. 2005, 1 page.
Author Unknown, "Blepharitis," The Eye Digest, The Dry Eye Research Center, University of Illinois at Chicago, 2003, 3 pages.
Author Unknown, "Introduction to the Report of the International Dry Eye WorkShop (2007)," The Ocular Surface, vol. 5, No. 2, Apr. 2007, pp. 69-70.
Author Unknown, "Keratoconjunctivitis Sicca" Wikipedia, http://en.wikipedia.org/wiki/keratoconjunctivitis_sicca, Nov. 2006, 4 pages.
Author Unknown, "Measurement of Intraocular Pressure" Biomedical Foundations of Ophthalmology, Intraocular Pressure, vol. 2, Chapter 7, Circa 1982, 6 pages (pp. 11-16).
Author Unknown, "Thermographic Camera" Wikipedia, http://en.wikipedia.org/wiki/thermographic_camera, Sep. 2006, 4 pages.
Bartlett, Hannah, et al. "New Perspectives on the Investigation and Treatment of Dry Eye Syndrome—Part 1" Optician, vol. 231, No. 6038, Feb. 2006, 9 pages (pp. 27-37).
Begley, Carolyn, G., et al., "Relationship Between Symptom Profile and Clinical Signs Among Dry Eye Patients" Circa 2003, 1 page.
Begley, Carolyn, G., et al., "The Relationship Between Habitual Patient-Reported Symptoms and Clinical Signs among Patients with Dry Eye of Varying Severity" Investigative Ophthalmology & Visual Science, vol. 44, No. 11, Nov. 2003, 9 pages (pp. 4753-4761).
Behrens, Ashley, MD, "Interferometry for the Detection of Dry Eye," Cataract & Refractive Surgery Today Europe, Nov./Dec. 2008. pp. 57-58.
Behrens, Ashley, MD, "Multiwave Interferometry is Creating a New Understanding of the Tear Film," Refractive Eyecare, Oct. 2009, from www.refractiveeyecare.com, 5 pages.
Berliner, M. L., M.D., "The Margins of the Eyelid" Chapter Eight, Biomicroscopy of the Eye, Slit Lamp Microscopy of the Living Eye, vol. 1, Medical Book Department of Harper & Brothers, NYC, Paul B. Hoeber, Inc., 1949, 5 pages (pp. 252-257).
Blackie, Caroline et al., "The Relationship Between Dry Eye Symptoms and Lipid Layer Thickness," Cornea, vol. 28, No. 7, Aug. 2009, pp. 789-794.
Borchman, Douglas, et al., "Temperature-Induced Conformational Changes in Human Tear Lipids Hydrocarbon Chains" Biopolymers, vol. 87, No. 2-3, Jun. 13, 2007, pp. 124-133 (10 pages).
Boyer, Kim L. et al., "Resilient Subclass Discriminant Analysis with Application to Prelens Tear Film Interferometry," Proceedings, Lecture Notes in Computer Science, vol. 6718/2011, MCPR, Cancun, Mexico, Jun. 29-Jul. 2, 2011, pp. 1-11.
Bron, A.J. et al., "Functional Aspects of the Tear Film Lipid Layer," Experimental Eye Research, vol. 78, 2004, pp. 347-360.
Bron, A.J. et al., "The Contribution of Meibomian Disease to Dry Eye," Ocul. Surf., vol. 2, 2004, pp. 149-164.
Bron, Anthony J., BSc, FRCS, FCOphth, et al., "The Ocular Appendages: Eyelids, Conjunctiva and Lacrimal Apparatus" Chapter 2, Wolff's Anatomy of the Eye and Orbit, Eighth Edition, Chapman & Hall Medical, Jan. 1997, 12 pages (pp. 30-42).
Carrington, S. D., et al., "Polarized Light Biomicroscopic Observations on the Pre-Corneal Tear Film" J. Small Anim. Pract., vol. 28, 1987, 20 pages (pp. 605-622).
Craig, J.P. et al., "Importance of the Lipid Layer in Human Tear Film Stability and Evaporation," Optometry and Visual Science, vol. 70, No. 1, 1997, pp. 8-14.
Cruz, Daniele, "Dry Eye Syndrome More Widespread than Predicted" Ocular Surgery News, U.S. Edition, May 2007, 1 page.
Cruz, Daniele, "Surgeon: Early Treatment Key to Avoiding Dry Eye Progression" Ocular Surgery News, U.S. Edition, May 2007, 1 page.
Danjo, Yukitaka, et al., "Measurement of the Precorneal Tear Film Thickness with a Non-Contact Optical Interferometry Film Thickness Measurement System" Jpn J Ophthal., vol. 38, 1994, 7 pages (pp. 260-266).
De Paiva, Cintia S., et al., "Diagnostic Approaches to Lacrimal Keratoconjunctivitis," Dry Eye and Ocular Surface Disorders, New York, NY: Marcel Dekker, 2004, pp. 269-270.
Di Pascuale, Mario A., M.D., et al., "Lipid Tear Deficiency in Persistent Dry Eye After Laser In Situ Keratomileusis and Treatment Results of New Eye-Warming Device" J Cataract Refract. Surg., vol. 31, ASCRS and ESCRS, Elsevier Inc., 2005, 9 pages (pp. 1741-1749).
Di Pascuale, Mario A., M.D., et al., "Sequential Changes of Lipid Tear Film after the Instillation of a Single Drop of a New Emulsion Eye Drop in Dry Eye Patients" American Academy of Ophthalmology, vol. 111, 2004, 9 pages (pp. 783-791).
Doane, Marshall G., "Abnormalities of the Structure of the Superficial Lipid Layer on the In Vivo Dry-Eye Tear Film" (and critique of same) Lacrimal Gland, Tear Film, and Dry Eye Syndromes, Plenum Press, New York, 1994, 11 pages (pp. 489-493).
Doane, Marshall G., "An Instrument for In Vivo Tear Film Interferometry" (and critique of same), Optometry and Vision Science, vol. 66, No. 6, 1989, 10 pages (pp. 383-388).
Doane, Marshall G., et al., "Tear Film Interferometry as a Diagnostic Tool for Evaluating Normal and Dry-Eye Tear Film" Lacrimal Gland, Tear Film, and Dry Eye Syndromes 2, Plenum Press, New York, 1998, 7 pages (pp. 397-303).
Dogru, M. et al., "New Insights into the Diagnosis and Treatment of Dry Eye," Ocular Surface, vol. 2, No. 2, 2004, pp. 59-74.
Dogru, M. et al., "Strip Meniscometry: A New and Simple Method of Tear Meniscus Evaluation," Invest. Ophthalmol. Vis. Sci., vol. 47, No. 5, May 2006, pp. 1895-1901.
Driver, Paul J., et al., "Meibomian Gland Dysfunction" Major Review, Survey of Ophthalmology, vol. 40, No. 5, Mar.-Apr. 1996, 25 pages (pp. 343-367).
Dubra, Alfredo, et al., "Double Lateral Shearing Interferometer for the Quantitative Measurement of Tear Film Topography" Applied Optics, vol. 44, No. 7, Mar. 2005, 9 pages (pp. 1191-1199).
Elizondo, A.E. et al., "Detection of Blink Related Microtrauma by Kinetic Analysis of Tear Interference Images in Patients with Steven Johnson Syndrome and Toxic Epidermal Necrolysis Syndrome," IOVS, vol. 46, Supp. S, 2005, E-Abstract 2654, 2 pages.
English translation of Japanese patent application announcement 2007-209370, 14 pages.
Eom et al., "Correlation Between Quantitative Measurements of Tear Film Lipid Layer Thickness and Meibomian Gland Loss in Patients with Obstructive Meibomian Gland Dysfunction and Normal Controls," American Journal of Ophthalmology, Jun. 2013, vol. 155, No. 6, Elsevier Inc., pp. 1104-1110.
Ernest, J. Terry, M.D. et al., "Ocular Massage Before Cataract Surgery" Tr. Am. Ophth. Soc., vol. LXXXIII, 1985, 13 pages (pp. 205-217).

(56) References Cited

OTHER PUBLICATIONS

European Search Report dated Jan. 20, 2012, for European Patent Application No. 11183259.8, 7 pages.
European Search Report for patent application 08732520.5 dated Feb. 24, 2012, 8 pages.
Extended European Search Report and Written Opinion for patent application 10759411.1-1657 dated May 14, 2013, 9 pages.
Examination Report for European patent application 11183259.8-1657 dated May 8, 2013, 7 pages.
Fanning, Gary L., M.D., "Ocular Compression: A Review," OASIS Newsletter, Ophthalmic Anesthesia Society, Summer 2006, http://www.eyeanesthesia.org/newsletter/pdf/oasis_summer06.pdf, 7 pages.
Fenimore, C.P., et al., "Assessment of Resolution and Dynamic Range for Digital Cinema" National Institute of Standards and Technology, Gaithersburg, MD, Circa 2002, 8 pages.
Finlayson, Graham, et al., "Hue that is Invariant to Brightness and Gamma" School of Information Systems, University of East Anglia, Norwich, United Kingdom, Circa 2002, 9 pages (pp. 303-312).
First Office Action for Chinese patent application 201080024927.9 dated May 13, 2013, 16 pages.
Fogt, Nick, et al., "Interferometric Measurement of Tear Film Thickness by use of Spectral Oscillations" J. Opt. Soc. Am. A., vol. 15, No. 1, Jan. 1998, 8 pages (pp. 268-275).
Foulks, G.N. et al., "Meibomian Gland Dysfunction: a Clinical Scheme for Description, Diagnosis, Classification, and Grading," The Ocular Surface, vol. 1, No. 3, Jul. 2003, pp. 107-126.
Foulks, G.N., "The Correlation Between the Tear Film Lipid Layer and Dry Eye Disease," Survey of Ophthalmology, vol. 52, No. 4, Jul.-Aug. 2007, pp. 369-374.
Foulks, G., "Ocular surface cell biology—from the light to the dark side," Ocular Surface, vol. 10, No. 4, Oct. 2012, 1 page.
Garcia, Julius, "Research Report; Tear Film Measurement" Report No. 09354231-1; Aug. 2006, 46 pages.
Garcia-Resua, C., et al., "Clinical Evaluation of the Tears Lipid Layer in a Young University Population" Rev. Esp. Contact, vol. 12, 2005, 6 pages.
Garncarz, B.E. et al., "Corneal Topography Measurement by Means of Radial Shearing Interference II—Experiment Results," Optik, vol. 113, No. 1, 2002, pp. 46-50.
Goto, E. et al., "Differentiation of Lipid Tear Deficiency Dry Eye by Kinetic Analysis of Tear Interference Images," Archives of Ophthalmology, vol. 121, No. 2 Feb. 2003, pp. 173-180.
Goto, E. et al., "Successful Tear Lipid Layer Treatment for Refractory Dry Eye in Office Workers by Low-Dose Lipid Application on the Full-Length Eyelid Margin," American Journal of Ophthalmology, vol. 142, No. 2, Aug. 2006, pp. 264-270.
Goto, E. et al., "Tear Evaporation Dynamics in Normal Subjects and Subjects with Obstructive Meibomian Gland Dysfunction," Investigative Ophthalmology abnd Visual Science, vol. 44, 2003, pp. 533-539.
Goto, E., et al. "Treatment of Non-Inflamed Obstructive Meibomian Gland Dysfunction by an Infrared Warm Compression Device" British Journal of Ophthalmology, BJO Online, http://www.bmjjournals.com/cgi/reprintform, vol. 26, 2002, 6 pages (pp. 1402-1407).
Goto, Eiki, et al. "Computer-Synthesis of an Interference Color Chart of Human Tear Lipid Layer, by a Colorimetric Approach" Investigative Ophthalmology & Visual Science, vol. 44, No. 11, Nov. 2003, 5 pages (pp. 4693-4697).
Goto, Eiki, et al., "Kinetic Analysis of Tear Interference Images in Aqueous Tear Deficiency Dry Eye Before and After Punctual Occlusion" Investigative Ophthalmology & Visual Science, vol. 44, No. 5, May 2003, 9 pages (pp. 1897-1905).
Goto, Eiki, M.D., "Quantification of Tear Interference Image; Tear Fluid Surface Nanotechnology" Cornea, vol. 23, Suppl. 1, Nov. 2004, 5 pages (pp. S20-S24).
Gravely, Ben, "Observations from TFA3" Aug. 2006, 4 pages.
Greiner, Jack V., et al., "Effect of Meibomian Gland Occlusion on Tear Film Lipid Layer Thickness" Lacrimal Gland, Tear Film, and Dry Eye Syndromes 2, Plenum Press, New York, 1998, 4 pages (pp. 345-348).
Greiner, Jack V., et al., "Meibomian Gland Phospholipids" Current Eye Research, Oxford University Press, 1995, 5 pages (pp. 371-375).
Greiner, Jack V., et al., "Volume of the Human and Rabbit Meibomian Gland System" Lacrimal Gland, Tear Film, and Dry Eye Syndromes 2, Plenum Pres, New York, 1998, 5 pages (pp. 339-343).
Guillon, J.P. et al., "Preocular Tear Film Characteristics of Nonwearers and Soft Contact Lens Wearers," Optometry and Vision Science, vol. 74, No. 5, 1997, pp. 273-279.
Guillon, J.P., "Tear Film Photography and Contact Lens Wear," Journal of the British Contact Lens Association, 1982, pp. 84-87.
Guillon, J.P., "The Tear Film Structure of the Contact Lens Wearer," Dept. of Optometry and Visual Science, City University, London, 1987, 398 pages.
Guillon, Jean-Pierre, "Non-Invasive Tearscope Plus Routine for Contact Lens Fitting," Contact Lens and Anterior Eye, (Supplement) 21, 1998, pp. S31-S40.
Guillon, Jean-Pierre, "Use of the Tearscope Plus and Attachments in the Routine Examination of the Marginal Dry Eye Contact Lens Patient," Lacrimal Gland, Tear Film, and Dry Eye Syndrome 2, 1998, pp. 859-867.
Hamilton, Dr. Roy C., "Ocular Explosion; a Dreaded Complication of Ophthalmic Regional Anaesthesia" Ophthalmic Anaesthesia News, Issue 4, Apr. 2001, 43 pages.
Hayreh, Sohan Singh, et al., "Parapapillary Chorioretinal Atrophy in Chronic High-Pressure Experimental Glaucoma in Rhesus Monkeys" Investigative Ophthalmology & Visual Science, vol. 39, No. 12, Nov. 1998, 8 pages (pp. 2296-1303).
Hellmuth, T. et al., "Non-Contact Measurement of the Optical Imaging Quality of an Eye," Proc. SPIE—Int. Soc. Opt. Eng. vol. 4431, 2001, pp. 52-58.
Hickson, Ian, "The Eye" Ian Hickson's Description of the Eye, http://academia.hixie.ch/bath/eye/home.html, 1998, 11 pages.
Author Unknown, Honan Balloon Intraocular Pressure Reducer with Valve—Complete, Ambler Surgical, Ambler Product No. HBC-120, Nov. 19, 2007, http://www.amblersurgical.com/store/product.cfm/pID:2456_5961E, 1 page.
Hosaka, Eri et al., "Interferometry in the Evaluation of Precorneal Tear Film Thickness in Dry Eye," American Journal of Opthalmology, vol. 151, No. 1, Jan. 2011, pp. 18-23.
International Search Report and Written Opinion for PCT/US2013/038116 dated Sep. 12, 2013, 13 pages.
International Search Report and Written Opinion for PCT/US2013/038149 dated Sep. 12, 2013, 18 pages.
International Search Report and Written Opinion for PCT/US2013/039395 dated Oct. 11, 2013, 11 pages.
Ishida, Reiko et al., "Tear Film with 'Orgahexa Eyemasks' in Patients with Meibomian Gland Dysfunction," Optometry and Visions Science, vol. 85, No. 8, Aug. 2008, pp. E684-E691.
Iskander, D. Robert, PhD., et al., "Applications of High-Speed Videokeratoscopy" Clinical and Experimental Optometry, vol. 88, vol. 4, Jul. 2005, 9 pages (pp. 223-231).
Isreb, M.A. et al., "Correlation of Lipid Layer Thickness Measurements with Fluorescein Tear Film Breakup Time and Schirmer's Test," Eye, vol. 17, 2003, pp. 79-83.
Kaisheva, M et al., "Thin Liquid Films from Water-Based Dispersions of Cellulose Acethophthalate in the Presence of Pilocarpine Hydrochloride," J. Dispersion Sci. Technol., 1997.
Khamene, Ali, et al., "A Spectral-Discrimination Method for Tear-Film Lipid-Layer Thickness Estimation from Fringe Pattern Images" IEEE Transactions on Biomedical Engineering, vol. 47, No. 2, Jan. 2000, 10 pages (pp. 249-258).
Kilp, H. et al., "Tear Film Observation by Reflecting Microscopy and Differential Interference Contrast Microscopy," The Dry Eye Institute, Inc., 1986, pp. 564-569.
Kimball, S., et al., "Evidence for the major contribution of evaporation to tear film thinning between blinks," Investigative Ophthalmology and Visual Science, vol. 51, No. 12, Dec. 2010, http://www.iovs.org/content/51/12/6294.full.pdf+html, pp. 6294-6297.
King-Smith, P. Ewen et al., "The Thickness of the Human Precorneal Tear Film: Evidence from Reflection Spectra," Investigative Ophthalmology & Visual Science, Oct. 2000, vol. 41, No. 11, pp. 3348-3359.

(56) References Cited

OTHER PUBLICATIONS

King-Smith, P. Ewen, et al., "Application of a novel interferometric method to investigate the relation between lipid layer thickness and tear film thinning," Investigative Ophthalmology and Visual Science, vol. 51, No. 5, May 2010, http://www.iovs.org/content/51/5/2418.full.pdf+html, pp. 2418-2423.

King-Smith, P. Ewen, et al., "Evaporation from the Human Tear Film Studied by Interferometry" Lacrimal Gland, Tear Film, and Dry Eye Syndromes 3, Kluwer Academic/Plenum Publishers, 2002, 5 pages (pp. 425-429).

King-Smith, P. Ewen, et al., "Interferometric Imaging of the Full Thickness of the Precorneal Tear Film" J. Opt. Soc. Am. A, vol. 23, No. 9, Sep. 2006, 8 pages (pp. 2097-2104).

King-Smith, P. Ewen, et al., "Three Interferometric Methods for Measuring the Thickness of Layers of the Tear Film" Optometry and Vision Science, vol. 76, No. 1, Jan. 1999, 14 pages (pp. 19-32).

King-Smith, P.E. et al., "Can the Mucus Layer of the Tear Film be Demonstrated by Interferometry?," IOVS, vol. 45, Supp. 2, Apr. 2004, E-Abstract 3882. 2 pages.

King-Smith, P.E. et al., "Human Tear Film Breakup Studied by a New Imaging Interferometer: Preliminary Observations," IOVS, vol. 46, Supp. S, 2005, E-Abstract 4400, 2 pages.

Kojima, Takashi et al.., "A New Noninvasive Tear Stability Analysis System for the Assessment of Dry Eyes," Investigative Ophthalmology & Visual Science, May 2004, vol. 45, No. 5, pp. 1369-1374.

Korb, D. et al., "Lipid Layer Thickness Changes Following the Instillation of Two Novel Lubricant Eye Drops," IOVS, vol. 46, Supp. S, 2005, E-Abstract 2036, 2 pages.

Korb, Donald R. et al., "Meibomian Gland Diagnostic Expressibility: Correlation With Dry Eye Symptoms and Gland Location," Cornea, vol. 27, No. 10, Dec. 2008, pp. 1142-1147.

Korb, Donald R. et al., "Effect of Periocular Humidity on the Tear Film Lipid Layer," Cornea, vol. 15, No. 2, 1996, pp. 129-134.

Korb, Donald R. et al., "Increase in Tear Film Lipid Layer Thickness Following Treatment of Meibomian Gland Dysfunction," Adv. Exp. Med. Biol., vol. 350, 1994, pp. 293-298.

Korb, Donald R. et al., "Tear Film Lipid Layer Thickness as a Function of Blinking," Cornea, vol. 13, No. 4, 1994, pp. 354-359.

Korb, Donald R. O.D., et al., "Comparison of Fluorescein Break-Up Time Measurement Reproducibility Using Standard Fluorescein Strips Versus the Dry Eye Test (DET) Method," Cornea, vol. 20(8), Philadelphia, 2001, 8 pages.

Korb, Donald R., "Alleviation of Computer-Induced Eye Discomfort Syndrome and Associated Lipid Layer Changes," Lacrimal Gland, Tear Film, and Dry Eye Syndrome 3, 2002, pp. 501-506.

Korb, Donald R., "The Tear Film—Its Role Today and in the Future," 2002, 52 pages.

Korb, Donald R., et al., "Human and Rabbit Lipid Layer and Interference Pattern Observations," Lacrimal Gland, Tear Film, and Dry Eye Syndromes 2, Plenum Press, New York, 1998, pp. 305-308.

Korb, Donald R., et al., "Tear Film Lipid Layer Formation: Implications for Contact Lens Wear," Review, Optometry and Vision Science, vol. 73, No. 3, 1996, pp. 189-192.

Korb, Donald R., et al., "The Effects of Anionic and Zwitterionic Phospholipids on the Tear Film Lipid Layer," Lacrimal Gland, Tear Film, and Dry Eye Syndromes 3, Kluwer Academic/Plenum Publishers, 2002, pp. 495-499.

Korb, Donald R., et al., "The Tear Film Structure, Function and Clinical Examination," British Contact Lens Association, Butterworth Heinemann, Circa 1999, pp. 154-179.

Korb, Donald R., O.D. et al., "The Phenomenon of Central Circular Clouding; the loss of corneal transparency unique to contact lens practice requiring specialized techniques for early recognition," Journal of American Optometric Association, vol. 39, No. 3, Mar. 1968, pp. 223-230.

Korb, Donald R., O.D., et al., "Lid Wiper Epitheliopathy and Dry Eye Syndrome," Eye & Contact Lens, vol. 31, No. 1, 2005, pp. 2-8.

Korb, Donald R., O.D., et al., "Meibomian Gland Dysfunction and Contact Lens Intolerance" Jnl American Optometric Association, vol. 51, No. 3, Mar. 1980, 9 pages (pp. 243-251).

Korb, Donald R., OD, et al., "A Device to Standardize and Quantify the Force Used to Diagnose Meibomian Gland Obstruction and Dysfunction" 2007, 1 page.

Korb, Donald R., OD, et al., "A New Device for the Diagnosis of Meibomian Gland Dysfunction and Obstruction" 2007, 1 page.

Korb, Donald, "Survey of Preferred tests for Diagnosis of the Tear Film and Dry Eye," Cornea, vol. 19, 2000, pp. 483-486.

Kowalik, W. et al., "Corneal Topography Measurement of the Eye by Means of Radial Shearing Interferometer," Proc. SPIE—Int. Soc. Opt. Eng. vol. 4356, 2001. pp. 375-380.

Kronemyer, Bob, "Dry Eye Experts Unveil New Treatment Guidelines, Terminology" Ocular Surgery News, U.S. Edition, May 2007, 1 page.

Leibovitch, Larry S., Ph.D., "The Shape of the Eye: Why the Eye is Round" Florida Atlantic University, Boca Raton, FL, Circa 1986, 28 pages (pp. 1-27).

Licznerski, T.J. et al., "Application of Twyman-Green Interferometer for Evaluation of In Vivio Breakup Characteristic of the Human Tear Film," Journal of Biomedical Optics, vol. 4, No. 1, Jan. 1999, pp. 176-182.

Licznerski, T.J. et al., "Interference and Model Study of the Human Tear Film," Politechnika Wroclawska, Source DAI-C 60/04, Winter 1999, p. 782 (Abstract only).

Licznerski, T.J. et al., "Novel Double Path Shearing Interferometer in Corneal Topography Measurements," Proceedings of the SPIE, vol. 5959, 2005, 6 pages.

Licznerski, Tomasz J., et al., "Analysis of Shearing Interferograms of Tear Film Using Fast Fourier Transforms" Journal of Biomedical Optics, vol. 3, No. 1, Jan. 1998, pp. 32-37.

Lopez Garcia, J.S. et al., "Measure of the Fatty Layer Thickness of Precorneal Tear Film by Interference Colours in Different Types of Dry Eye," Sociedad Espanola de Oftalmologia, vol. 78, Part 5, Jan. 2003, pp. 257-264.

Lorentz, Holly Irene, "Lipid Deposition on Hydrogel Contact Lenses" Master's Thesis, University of Waterloo, Ontario, Canada, 2006, 175 pages.

Loveridge, Ron, "Effective Management of Induced Dry Eye Syndrome with Soft CLs" www.optometry.co.uk, Apr. 2000,pp. 35-38.

Lui, Haixia, MD, et al., "Temporal Progression and Spatial Repeatability of Tear Breakup" Optometry and Vision Science, vol. 83, No. 10, Oct. 2006, pp. 723-730.

Mathers, W.D., "Assessment of the Tear Film with Tandem Scanning Confocal Microscopy," Cornea, vol. 16, No. 2, 1997, pp. 162-168.

Mathers, W.D., "Ocular Evaporation in Meibomian Gland Dysfunction and Dry Eye," Ophthalmology, vol. 100, No. 3, Mar. 1993, pp. 347-351.

Matsumoto, Yukihiro, et al., "Efficacy of a New Warm Moist Air Device on Tear Functions of Patients with Simple Meibomian Gland Dysfunction" Cornea, vol. 25, No. 6, Jul. 2006, 1 page.

McCarty, C.A. et al., "The Epidemiology of Dry Eye in Melbourne, Australia," Ophthalmology, vol. 105, No. 6, Jun. 1998, pp. 1114-1119.

McDonald, James E., "Surface Phenomena of the Tear Films," Tr. Am. Opth. Soc., vol. 66, 1968, pp. 905-939.

McGrath, Dermot, "Iris diaphragm IOLs safe and effective in treating aniridia," EuroTimes, European Society of Cataract & Refractive Surgeons, May 2007, http://www.escrs.org/PUBLICATIONS/EUROTIMES/07MAY/IRISDIAPHRAGMIOLS.PDF, p. 42.

Miano, Fausto, et al., "Interface Properties of Simplified Tear-Like Fluids in Relation to Lipid and Aqueous Layers Composition" Lacrimal Gland, Tear Film, and Dry Eye Syndromes 3, Kluwer Academic/Plenum Publishers, 2002, 13 pages (pp. 405-417).

Millar, et al., "Analysis of comparison of human meibomian lipid films and mixtures with cholestryl esters in vitro films using high resolution color microscopy," Cornea, vol. 53, No. 8, Jul. 2012, pp. 4710-4719.

Miller, David "Pressure of the Lid on the Eye" Arch. Opthalmology, vol. 78, 1967, 7 pages (pp. 382-330).

Mitra, M. et al., "Tear Film Lipid Layer Thickness and Ocular Comfort after Meibomian Therapy via Latent Heat with a Novel Device in Normal Subjects" Eye, vol. 19, 2005, 4 pages (pp. 657-660).

(56) References Cited

OTHER PUBLICATIONS

Mori, Asako, M.D., et al., "Efficacy and Safety of Infrared Warming of the Eyelids" Cornea, vol. 18(2), 1999, 6 pages (pp. 188-193).
Nichols, Jason J., et al., "The Impact of Hydrogel Lens Settling on the Thickness of the Tears and Contact Lens" Investigative Ophthalmology & Visual Science, vol. 45, No. 8, Aug. 2004, pp. 2549-2554.
Nichols, Jason J., et al., "The Thickness of the Post-Lens Tear Film Measured by Interferometry" Lacrimal Gland, Tear Film, and Dry Eye Syndromes 3, Kluwer Academic/Plenum Publishers, 2002, pp. 929-933.
Nichols, Jason J., et al., "Thickness of the Pre- and Post-Contact Lens Tear Film Measured In Vivo by Interferometry" Investigative Ophthalmology & Visual Science, vol. 44, No. 1, Jan. 2003, pp. 68-77.
Nichols, Jason J., OD, MS, Faao, et al., "Evaluation of Tear Film Interference Patterns and Measures of Tear Break-Up Time" Optometry and Vision Science, vol. 79, No. 6, Jun. 2002, pp. 363-369.
Nichols, Jason J., OD, MS, MPH, et al., "The Effect of Eye Closure on the Post-Lens Tear Film Thickness During Silicone Hydrogel Contact Lens Wear" Cornea, vol. 22, No. 6, 2003, pp. 539-544.
Nichols, K.K. et al., "The Lack of Association Between Signs and Symptoms in Patients with Dry Eye Disease," Cornea, vol. 23, No. 8, Nov. 2004, pp. 762-770.
Nichols, K.K. et al., "The Repeatability of Clinical Measurements of Dry Eye," Cornea, vol. 23, No. 3, Apr. 2004, pp. 272-285.
Norn, M.S., "Semiquantitative Interference Study of Fatty Layer of Precorneal Film," ACTA Ophthalmologica, vol. 57, 1979, pp. 766-774.
Corrected Notice of Acceptance for Australian patent application 2011235961 dated Sep. 19, 2013, 2 pages.
Notice of Acceptance for Australian patent application 2011235961 dated Sep. 11, 2013, 2 pages.
Ohashi, Yoshiki, et al., "Laboratory Findings in Tear Fluid Analysis," Clinica Chimica Acta 369, 2006, 12 pages (pp. 17-28).
Olson, Mary Catherine, B.A., et al., "Increase in Tear Film Lipid Layer Thickness Following Treatment with Warm Compresses in Patients with Meibomian Gland Dysfunction" Eye & Contact Lens, vol. 29(2), 2003, 6 pages.
Ong, B. L., et al., "Meibomian Gland Dysfunction: Some Clinical, Biochemical and Physical Observations" Ophthal. Physiol. Opt., vol. 10, Apr. 1990, 5 pages (pp. 144-148).
Patel, S. et al., "Corneal Sensitivity and Some Properties of the Tear Film After Laser In Situ Keratomileusis," Journal of Refractive Surgery, Vo. 17, No. 1, 2001, pp. 17-24.
Patel, Sudi, PhD, FCOptom, Faao, et al., "Tear Meniscus Height, Lower Punctum Lacrimale, and Tear Lipid Layer in Normal Aging" Optometry and Vision Science, vol. 83, No. 10, Oct. 2006, 9 pages (pp. 732-739).
Paugh, J.R. et al., "White Light Tear Film Interferometry in Dry Eye Sub-Types," IOVS, vol. 45, Supp. 1, Apr. 2004, E-Abstract 93, 2 pages.
Pflugfelder, S.C. et al., "Evaluation of Subjective Assessments and Objective Diagnostic Tests for Diagnosing Tear-Film Disorders Known to Cause Ocular Irritation," Cornea, vol. 17, No. 1, 1998, pp. 38-56.
Pimenidi, M.K., et al., "Meibomian Gland Disfunction in Computer Vision Syndrome (abstract)," Annals of Ophthalmology (Vestn Oftalmol.) (Russia), Nov.-Dec. 2010, 126(6), http://www.medlit.ru/medeng/vof/vof10e0649.htm, 3 pages.
Primeau et al., "Interferometer for measuring the dynamic surface topography of a human tear film," Design and Quality for Biomedical Technologies V, vol. 8215, Feb. 2012, 11 pages.
Prydal, J.I. et al., "In Vivo Confocal Microscopy of the Cornea and Tear Film," Scanning, vol. 17, 1995, pp. 133-135.
Prydal, J.I. et al., "Study of Precorneal Tear Film Thickness and Structure by Interferometry and Confocal Microscopy," Investigative Ophthalmology and Visual Science, vol. 33, No. 6, May 1992, pp. 1996-2005.

Prydal, Jeremy I. et al., "Study of Human Precorneal Tear Film Thickness and Structure Using Laser Interferometry," Investigative Ophthalmology & Visual Science, vol. 33, No. 6, May 1992, pp. 2006-2011.
Remeseiro et al., "Automatic classification of the interferential tear film lipid layer using colour texture analysis," Computer Methods and Programs in Biomedicine, vol. 111, No. 1, Elsevier Ireland Ltd., Jul. 2013, pp. 93-103.
Rolando, M. et al., "The Dynamic Lipid Interference Pattern (DLIP) Test in Normal and Dry Eyes," IOVS, vol. 46, Supp. S, 2005, E-Abstract 4422, 2 pages.
Rolando, Maurizio et al., "New Test to Quantify Lipid Layer Behavior in Healthy Subjects and Patients with Keratoconjunctivitis Sicca," Cornea, vol. 27, No. 8, Sep. 2008, pp. 866-870.
Scaffidi, R.C. et al., "Lipid Layer Thickness and Dry Eye Symptoms," IOVS, vol. 46, Supp. S, 2005, E-Abstract 4444, 2 pages.
Schaumberg, D.A. et al., "Development and Validation of a Short Global Dry Eye Symptom Index," The Ocular Surface, vol. 5, No. 1, Jan. 2007, pp. 50-57.
Shiel, William C., Jr., MD, FACP, FACR, "Sjogren's Syndrome" MedicineNet.com, http:www.medicinenet.com, Sep. 2006, 3 pages.
Sullivan, David A., et al., "Androgen Influence on the Meibomian Gland" Investigative Ophthalmology & Visual Science, vol. 41, No. 12, Nov. 2000, 11 pages (pp. 3732-3742).
Sullivan, David A., et al., "Androgen Regulation of the Meibomian Gland" Lacrimal Gland, Tear Film, and Dry Eye Syndromes 2, Plenum Press, New York, 1998, 5 pages (pp. 327-331).
Szczesna-Iskander, D. et al., "Future Directions in Non-Invasive Measurements of Tear Film Surface Kinetics," Optometry and Vision Science, vol. 89, No. 5, May 2012 pp. 749-759.
Szczesna, D. et al., "Numerical Analysis of Interferograms of Tear Film Build-Up Time," Ophthalmic and Physiological Optics, vol. 29, No. 3, May 2009, pp. 211-218.
Szczesna, D., et al., "Predicting dry eye using noninvasive techniques of tear film surface assessment," Investigative Ophthalmology and Vision Science, vol. 52, No. 2, Feb. 2011, http://www.iovs.org/content/52/2/751.full.pdf+html, pp. 751-756.
Szczesna, D.H. et al., "Interferometric Measurements of the Tear Film Irregularities on the Human Cornea," Proceedings of the SPIE, vol. 5959, 2005, 10 pages.
Szczesna, Dorota H., et al., "Assessing Tear Film on Soft Contact Lenses With Lateral Shearing Interferometry," Eye & Contact Lens: Science & Clinical Practices, vol. 37, Issue 6, Nov. 2011, pp. 342-347.
Szczesna, Dorota H., et al., "Lateral Shearing Interferometry for Analysis of Tear Film Surface Kinetics," Optom. Vis. Sci., vol. 87, No. 7, Jul. 2010, pp. 513-517.
Szczesna, Dorota H., et al., "Robust estimation of tear film surface quality in lateral shearing interferometry," Journal of Biomedical Optics, vol. 14, No. 6, Nov./Dec. 2009, 4 pages.
Thai, Lee Choon, BSc, MCOptom, et al., "Contact Lens Drying and Visual Performance: The Vision Cycle with Contact Lenses" Optometry and Vision Science, vol. 79, No. 6, Jun. 2002, 8 pages (pp. 381-388).
Thai, Lee Choon, BSc, MCOptom, et al., "Effect of Contact Lens Materials on Tear Physiology" Optometry and Vision Science, vol. 81, No. 3, Mar. 2004, 11 pages (pp. 194-204).
Tomlinson, Alan, et al., "Reliability of Measurements of Tear Physiology" Lacrimal Gland, Tear Film, and Dry Eye Syndromes 3, Kluwer Academic/Plenum Publishers, 2002, 9 pages (pp. 1097-1105).
Tomlinson, Alan, et al., "Tear Film Osmolarity: Determination of a Referent for Dry Eye Diagnosis" Investigative Ophthalmology & Visual Science, vol. 47, No. 10, Oct. 2006, 7 pages (pp. 4309-4315).
Tseng, S.C. et al., "Changes of Lipid Tear Film in Dry Eye Patients and Normal Subjects Following One Drop of a New Emulsion Eye Drop Using Kinetic Analysis of Tear Interference Images," ARVO, vol. 44, 2003, E-Abstract 2457, 2 pages.
Uchida, A. et al., "Nonivasive Interference Tear Meniscometry in Dry Eye Patients with Sjogren Syndrome," Am. J. Ophthalmol., vol. 144, No. 2, Aug. 2007, pp. 232-237.

(56) References Cited

OTHER PUBLICATIONS van Veen, R. L. P., et al., "Determination of VIS—NIR Absorption Coefficients of Mammalian Fat, with Time- and Spatially Resolved Diffuse Reflectance and Transmission Spectroscopy" CIRCA 2004, 3 pages.
Veres, A., et al., "Imaging lid-parallel conjunctival folds with OCT and comparing its grading with the slit lamp classification in dry eye patients and normal subjets," Investigative Ophthalmology and Visual Science, vol. 52, No. 6, May 2011, http://www.iovs.org/content/52/6/2945.full.pdf+html, pp. 2945-2951.
Wang, Jianhua et al., "Relationships between Central Tear Film Thickness and Tear Menisci of the Upper and Lower Eyelids" Investigative Ophthalmology & Visual Science, vol. 47, No. 10, Oct. 2006, 7 pages (pp. 4349-4355).
Wu, Dijia et al., "Sign Ambiguity Resolution for Phase Demodulation in Interferometry with Application to Prelens Tear Film Analysis," 2010 IEEE Computer Society Conference on Computer Visions and Pattern Recognition, CVPR 2010, 2010, pp. 2807-2814.
Wu, Dijia et al., "Texture Based Prelens Tear Film Segmentation in Interferometry Images," Machine Vision and Applications, vol. 21, No. 3, Apr. 2010, pp. 253-259.
Yokoi, N, et al., "Development of Automated Rheological Analysis for Tear Film Lipid Layer Spread Using the Cross-Correlation Method" Association for Research in Vision and Ophthalmology, 2007, 1 page.
Yokoi et al., "A Newly Developed Video-Meibography System Featuring a Newly Designed Probe," Japan Journal of Ophthalmology, vol. 51, Jan. 2007, pp. 53-56.
Yokoi, N. et al., "Assessment of Meibomian Gland Function in Dry Eye Using Meibometry," Arch. Ophthalmol., No. 117, Jun. 1999, pp. 723-729.
Yokoi, N. et al., "Correlation of Tear Lipid Layer Interference Patterns with the Diagnosis and Severity of Dry Eye," Amercian Journal of Ophthalmology, vol. 122, Dec. 1996, pp. 818-824.
Yokoi, N. et al., "New Instruments for Dry Eye Diagnosis," Seminars in Opthalmology, vol. 20, 2004, pp. 63-70.
Yokoi, Norihiko, et al., "Non-Invasive Methods of Assessing the Tear Film" Experimental Eye Research, vol. 78, Elsevier Ltd., 2003, 9 pages (pp. 399-407).
Young, G. et al., "Characteristics of the Pre-Lens Tear Films During Hydrogel Contact Lens Wear," Ophthal. Physiol. Opt., vol. 11, Jan. 1991, pp. 53-58.
Oculus, "Oculus Keratograph 5M Der Revolutionar," Oculus, 2 pages.
Bon, "Meibographie: mit der Phoenix Analyse-Software," bon Optic Vertriebsgesellschaft mbH, Nov. 2011, 4 pages.
Yokoi, N. et al., "Relationship between tear volume and tear meniscus curvature," Arch. Ophthalmology, vol. 122, Sep. 2004 ,pp. 1265-1269.
Notice of Allowance for U.S. Appl. No. 11/820,664 dated May 27, 2010, 10 pages.
Notice of Allowance for U.S. Appl. No. 11/820,664 dated Mar. 25, 2010, 10 pages.
Final Office Action for U.S. Appl. No. 11/820,664 dated Dec. 29, 2009, 7 pages.
Non-final Office Action for U.S. Appl. No. 11/820,664 dated Jun. 5, 2009, 9 pages.
Notice of Allowance for U.S. Appl. No. 12/633,057 dated Jun. 9, 2011, 8 pages.
Final Office Action for U.S. Appl. No. 12/633,057 dated Apr. 6, 2011, 6 pages.
Non-final Office Action for U.S. Appl. No. 12/633,057 dated Aug. 19, 2010, 8 pages.
Notice of Allowance for U.S. Appl. No. 11/900,314 dated Jan. 25, 2012, 7 pages.
Non-final Office Action for U.S. Appl. No. 11/900,314 dated Aug. 22, 2011, 26 pages.
Non-final Office Action for U.S. Appl. No. 12/798,325 dated Jan. 27, 2012, 15 pages.
Non-final Office Action for U.S. Appl. No. 12/798,325 dated Aug. 30, 2012, 16 pages.
Notice of Allowance for U.S. Appl. No. 12/798,325 dated Feb. 15, 2013, 9 pages.
Notice of Allowance for U.S. Appl. No. 12/798,325 dated May 29, 2013, 10 pages.
Notice of Allowance for U.S. Appl. No. 29/329,613 dated Feb. 4, 2010, 7 pages.
Notice of Allowance for U.S. Appl. No. 29/329,613 dated Nov. 13, 2009, 7 pages.
Non-Final Rejection dated Apr. 20, 2012, for U.S. Appl. No. 12/798,275, 15 pages.
Final Office Action for U.S. Appl. No. 12/798,275 dated Nov. 20, 2012, 16 pages.
Reply to Final Office Action for U.S. Appl. No. 12/798,275, filed Jan. 29, 2013, 6 pages.
Advisory Action for U.S. Appl. No. 12/798,275 dated Feb. 5, 2013, 9 pages.
Non-final Office Action for U.S. Appl. No. 12/798,275 dated Jul. 30, 2013, 15 pages.
Notice of Allowance for U.S. Appl. No. 12/798,326 dated Aug. 29, 2011, 9 pages.
Non-final Office Action for U.S. Appl. No. 12/798,326 dated Jun. 28, 2011, 19 pages.
Non-final Office Action for U.S. Appl. No. 12/798,326 dated Mar. 29, 2011, 23 pages.
Notice of Allowance for U.S. Appl. No. 12/798,324 dated Apr. 2, 2012, 9 pages.
Non-final Office Action for U.S. Appl. No. 12/798,324 dated Dec. 15, 2011, 27 pages.
Non-final Office Action for U.S. Appl. No. 13/455,628 dated Aug. 29, 2012, 18 pages.
Final Office Action for U.S. Appl. No. 13/455,628 dated May 10, 2013, 9 pages.
Notice of Allowance for U.S. Appl. No. 13/455,628 dated Jul. 12, 2013, 8 pages.
Translation of Notice of Rejection for Japanese patent application 2010-513285 dated Nov. 6, 2012, 4 pages.
Non-final Office Action for U.S. Appl. No. 13/195,353 dated May 3, 2013, 5 pages.
Notice of Allowance for U.S. Appl. No. 13/195,353 dated Jul. 26, 2013, 9 pages.
Fagehi, Raied et al., "Contact Lens in Vitro Wettability by Interferometry Measures of Drying Dynamics," Eye & Contact Lens, vol. 39, No. 6, Contact Lens Association of Ophthalmologists, Nov. 2013, pp. 365-375.
Finis et al., "Evaluation of lipid layer thickness measurement of the tear film as a diagnostic tool for Meibomian gland dysfunction," Cornea, vol. 32, No. 12, Dec. 2013, Lippincott Williams & Wilkins, 5 pages.
Lu, Hui et al., "Combination of Optical Coherence Tomography and Reflectometry Technique for Eye Measurement," Proceedings of SPIE, vol. 8567, Ophthalmic Technologies XXIII, 85672C, Mar. 26, 2013, 6 pages.
Lu, Hui et al., "Tear film measurement by optical reflectometry technique," Journal of Biomedical Optics, vol. 19, No. 2, Feb. 2014, 8 pages.
Primeau et al., "Interferometer and analysis methods for the in vitro characterization of dynamic fluid layers on contact lenses," Optical Engineering, vol. 51, No. 6, SPIE, Jun. 1, 2012, 9 pages.
Sweeney, Deborah F., et al., "Tear film stability: A review," Experimental Eye Research, vol. 117, Elsevier Ltd., Dec. 2013, pp. 28-38.
Szczesna, Dorota H. et al., "Interferometric measurements of dynamic changes of tear film," Journal of Biomedical Optics, vol. 11, No. 3, May 2006, 8 pages.
International Search Report and Written Opinion for PCT/US2013/077117 dated Mar. 18, 2014, 34 pages.
Second Office Action for Chinese patent application 201080024927.9 dated Mar. 21, 2014, 15 pages.
Translation of Notice of Rejection for Japanese patent application 2010-513285 dated Dec. 3, 2013, 8 pages.
Translation of Notice of Rejection for Japanese patent application 2012-503707 dated Dec. 3, 2013, 3 pages.

(56) References Cited

OTHER PUBLICATIONS

Notice of Allowance for U.S. Appl. No. 12/798,275 dated Jan. 2, 2014, 8 pages.
King-Smith, P.E. et al., "Tear film interferometry and corneal surface roughness," Investigative Ophthalmology & Visual Science, vol. 55, No. 4, Apr. 1, 2014, Association for Research in Vision and Ophthalmology Inc., pp. 2614-2618.
Qazi, Yureeda et al., "Image-guided evaluation and monitoring of treatment response in patients with dry eye disease," Graefe's Archive for Clinical and Experimental Ophthalmology, vol. 252, Issue 6, Jun. 2014, Springer Verlag, pp. 857-872.
Wu, Yuan et al., "Correlation between measurement of tear meniscus by anterior segment module of OCT with dry eye signs and symptoms," Chinese Journal of Experimental Ophthalmology, vol. 32, No. 6, Jun. 2014, Henan Institute of Ophthalmology, pp. 541-545.
Notice of Allowance for U.S. Appl. No. 13/870,054 dated Jul. 17, 2014, 9 pages.
Notice of Allowance for U.S. Appl. No. 14/137,105 dated Jul. 18, 2014, 9 pages.
Agnifili et al., "In vivo confocal microscopy of meibomian glands in glaucoma," British Journal of Ophthalmology, vol. 97, No. 3, Mar. 2013, pp. 343-349, United Kingdom.
Mansour, Ahmad M., "Meibomian Gland Secretion" Orbit: The International Journal on Orbital Disorders, Oculoplastic and Lacrimal Surgery, vol. 7 Iss. 3, Sep. 1988, pp. 201-209, (Abstract Only).
Komuro, A. et al., "Examination of the Meibomian Gland," New Ophthalmology, vol. 18, No. 3, Mar. 31, 2001, pp. 301-306 (Japanese version and partial translation).
Matsuoka, Tooru et al., "Value of Meibography of the Upper Eyelid in Meibomian Gland Dysfunction," Japanese Journal of Clinical Ophthalmology, vol. 53 No. 3, Oct. 1998, pp. 389-393, (Abstract Only).
Bucsko, J.K., "Imaging the Eye with Very-High-Frequency Ultrasound," Radiology Today, vol. 5 No. 19, Sep. 13, 2004, 4 pages.
Arcscan, "Product Description," ArcScan, Accessed Jan. 9, 2008, 5 pages, http://www.arcscan.com/products.html.
Visual Sonics, "Inflammation Quantified in Vivo," VisualSonics, Accessed Jan. 9, 2008, 2 pages, http://www.visualsonics.com/.
Paradigm, "P45," Paradigm Medical, Accessed Jan. 9, 2008, 2 pages, http://web.archive.org/web/20060207051154/http://paradigm-medical.com/products/P45.htm.
OTI Ophthalmic Technologies, Inc., "OCT/SLO Technical Specifications," OTI Ophthalmic Technologies Inc., Accessed Jan. 9, 2008, 2 pages, http://web.archive.org/web/20051108020036/http://www.oti-canada.com/octspecs.htm.
Quantel Medical, "New Ophthalmic Products," Quantel Medical Ophthalmic Products, Accessed Jan. 9, 2008, 4 pages, http://web.archive.org/web/20060221081738/http://quantelmedical.com/index.htm.
Van Velthoven, M. et al., "Overlay of Conventional Angiographic and en-face OCT Images Enhances their Interpretation," BMC Ophthalmology, vol. 5 No. 12, Jun. 2005, 13 pages.
Stratus OCT, "Vision of Technology," Stratus OCT, 2002, 6 pages.
Matsumoto, Yukihiro et al., "The Evaluation of the Treatment Response in Obstructive Meibomian Gland Disease by In Vivo Laser Confocal Microscopy," Graefes Arch Clin Exp Ophthalmol, vol. 247, No. 6, Jun. 2009, pp. 821-829.
Knop, E. et al., "Meibomian Glands: Part III—Dysfunction—Argument for a Discrete Disease Entity and as an Important Cause of Dry Eye," Ophthalmologe, vol. 106, No. 11, Nov. 2009, pp. 966-979. (Abstract Only).
Knop, E. et al., "Meibomian Glands: Part IV—Functional Interactions in the Pathogenesis of Meibomian Gland Dysfunction (MGD)," Ophthalmologe, vol. 106, No. 11, Nov. 2009, pp. 980-987. (Abstract Only).
Alsuhaibani, Adel et al. "Utility of Meibography in the Evaluation of Meibomian Glands Morphology in Normal and Diseased Eyelids," Saudi Journal of Ophthalmology, vol. 25, No. 1, Jan.-Mar. 2011, pp. 61-66.
Messmer et al., "Konfokale in-vivo-mikroscopie bei Blepharitis," Klin. Monatsbl. Augenheilkund., vol. 222, 2005, pp. 894-900.
Robin et al., "In vivo transillumination biomicroscopy and photography of meibomian gland dysfunction," Ophthalmology, vol. 92, No. 10, Oct. 1985, pp. 1423-1426.
Yamaguchi et al., "Marx line: fluorescein staining line on the inner lid as indicator of meibomian gland function," American Journal of Ophthalmology, vol. 141, No. 4, Apr. 1, 2006, pp. 669-669.
Notice of Allowance for U.S. Appl. No. 11/540,422 dated Jun. 21, 2012, 9 pages.
Non-final Office Action for U.S. Appl. No. 11/540,422 dated Aug. 31, 2011, 14 pages.
Final Office Action for U.S. Appl. No. 11/540,422 dated Jul. 20, 2010, 11 pages.
Non-final Office Action for U.S. Appl. No. 11/540,422 dated Dec. 30, 2009, 11 pages.
Non-final Office Action for U.S. Appl. No. 11/540,422 dated Apr. 15, 2009, 10 pages.
Notice of Allowance for U.S. Appl. No. 11/893,669 dated Apr. 26, 2012, 7 pages.
Final Office Action for U.S. Appl. No. 11/893,669 dated Feb. 15, 2012, 21 pages.
Non-final Office Action for U.S. Appl. No. 11/893,669 dated Jun. 9, 2011, 21 pages.
Non-final Office Action for U.S. Appl. No. 13/325,586 dated Jul. 5, 2012, 8 pages.
Non-final Office Action for U.S. Appl. No. 13/472,654 dated Jun. 20, 2012, 14 pages.
International Search Report for PCT/US07/00505 dated Nov. 20, 2007, 10 pages.
Office Action for Japanese patent application 2009-530326 dated Apr. 3, 2012, 6 pages.
Translation of the 2nd Official Action for Japanese patent application 2009-530326 dated Mar. 26, 2013, 6 pages.
Supplementary European Search Report for application 07716444 dated Oct. 4, 2012, 4 pages.
Final Office Action for U.S. Appl. No. 13/472,654 dated Jan. 22, 2013, 14 pages.
Final Office Action for U.S. Appl. No. 13/325,586 dated Feb. 12, 2013, 11 pages.
Advisory Action for U.S. Appl. No. 13/472,654 dated Apr. 8, 2013, 3 pages.
Non-final Office Action for U.S. Appl. No. 13/325,586 dated Jun. 25, 2013, 12 pages.
Final Office Action for U.S. Appl. No. 13/325,586 dated Feb. 10, 2014, 14 pages.
Notice of Allowance and Interview Summary for U.S. Appl. No. 13/472,654 dated Jul. 30, 2013, 12 pages.
Hrynchak et al., "Optical Coherence Tomography: An Introduction to the Technique and its Use," Optometry and Vision Science, vol. 77, No. 7, Jul. 2000, pp. 347-356.
Arita, Reiko et al., "Objective image analysis of the meibomian gland area," British Journal of Ophthalmology, vol. 98, No. 6, 2014, BMJ Publishing Group, pp. 746-755.
Translation of Examiner's Decision of Rejection for Japanese patent application 2009-530326 dated May 20, 2014, 3 pages.
Notice of Allowance for Korean Patent Application No. 10-2011-7026079, dated Jan. 16, 2017, 4 pages.
Ji, Yong Woo et al., "Automated Measurement of Tear Film Dynamics and Lipid Layer Thickness for Assessment of Non-Sjögren Dry Eye Syndrome With Meibomian Gland Dysfunction," Cornea, vol. 36, Issue 2, Feb. 2017, Wolters Kluwer Health, Inc., pp. 176-182.
Final Office Action for U.S. Appl. No. 14/543,583, dated Mar. 1, 2017, 14 pages.
Corrected Notice of Allowance for U.S. Appl. No. 14/299,504, dated Feb. 21, 2017, 4 pages.
Corrected Notice of Allowance for U.S. Appl. No. 14/299,504, dated Mar. 17, 2017, 4 pages.
Notice of Allowance for U.S. Appl. No. 14/299,504, dated Apr. 5, 2017, 7 pages.
Examination Report for European Patent Application No. 11183259.8, dated Feb. 14, 2017, 11 pages.

(56) References Cited

OTHER PUBLICATIONS

Examination Report for European Patent Application No. 10759411.1, dated Feb. 14, 2017, 10 pages.
Notice of Allowance for U.S. Appl. No. 15/995,612, dated Nov. 15, 2018, 8 pages.
Summons to attend oral proceedings for European Patent Application No. 10759411.1, dated Dec. 3, 2018, 8 pages.
Examination Report for European Patent Application No. 14792343.7, dated Dec. 11, 2018, 4 pages.
Non-Final Office Action for U.S. Appl. No. 15/791,615, dated Feb. 5, 2019, 15 pages.
Examination Report No. 2 for Australian Patent Application No. 2014259619, dated Jan. 17, 2019, 3 pages.
Final Office Action for Japanese Patent Application No. 2016-512105, dated Dec. 5, 2018, 3 pages.

\* cited by examiner

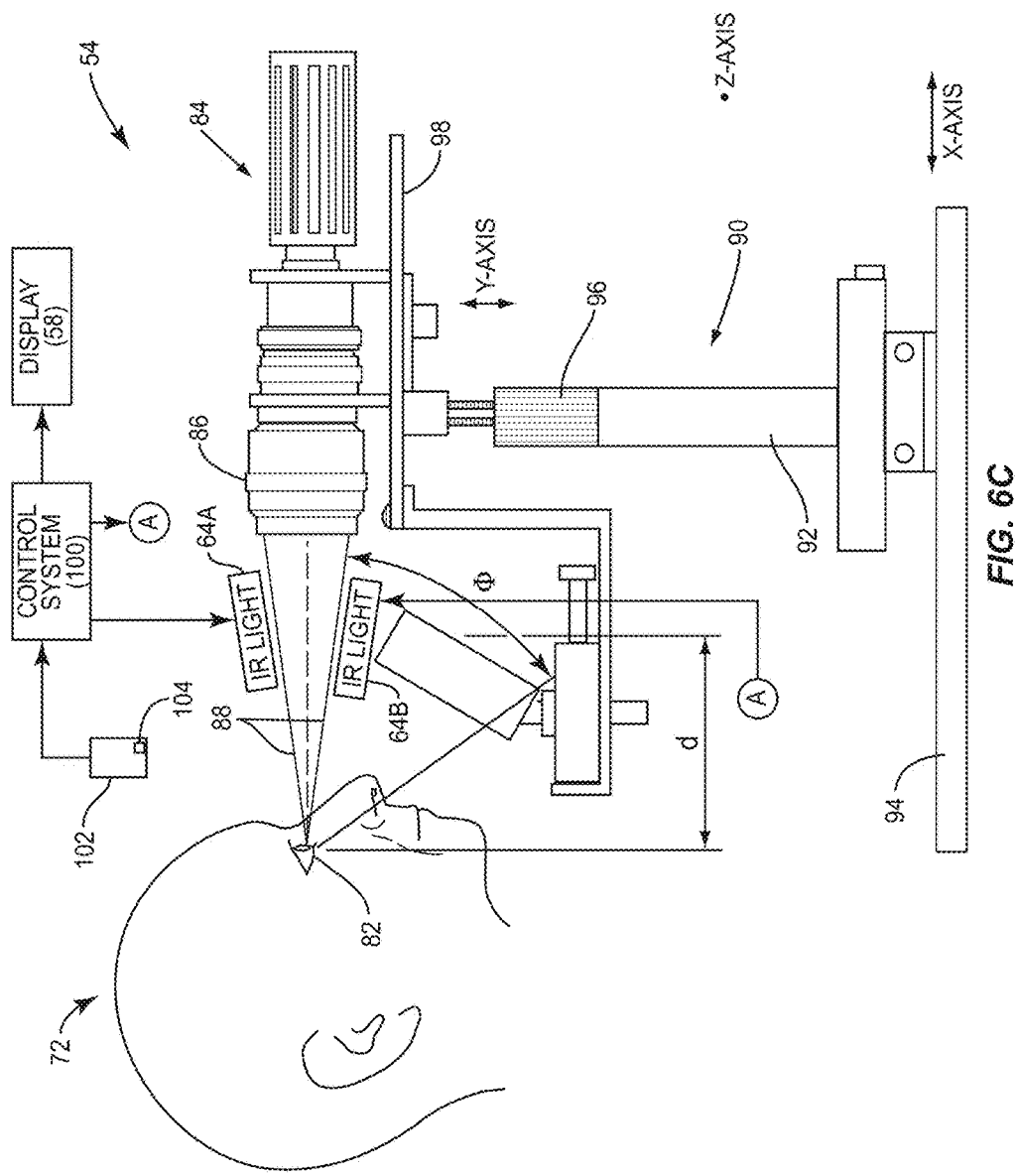

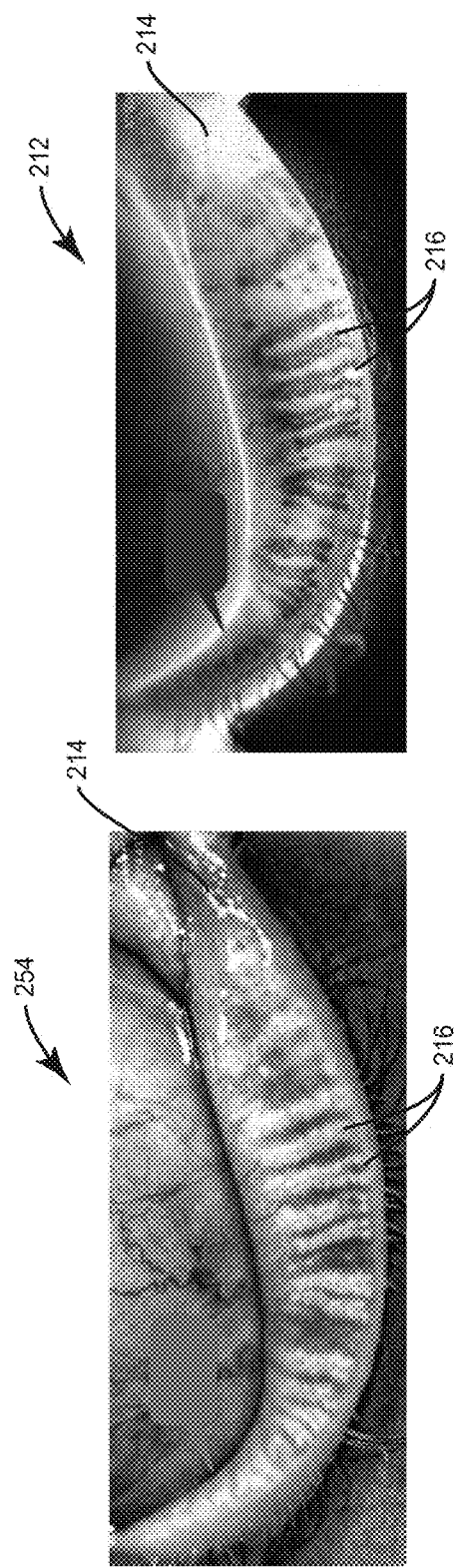
FIG. 16A
FIG. 16B
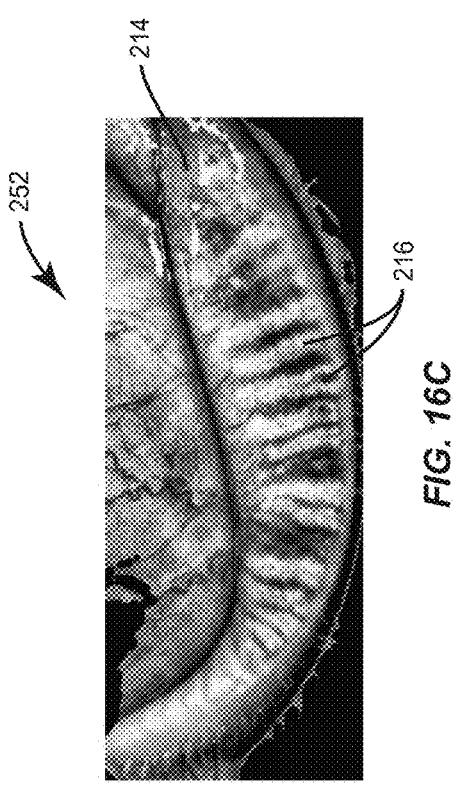
FIG. 16C

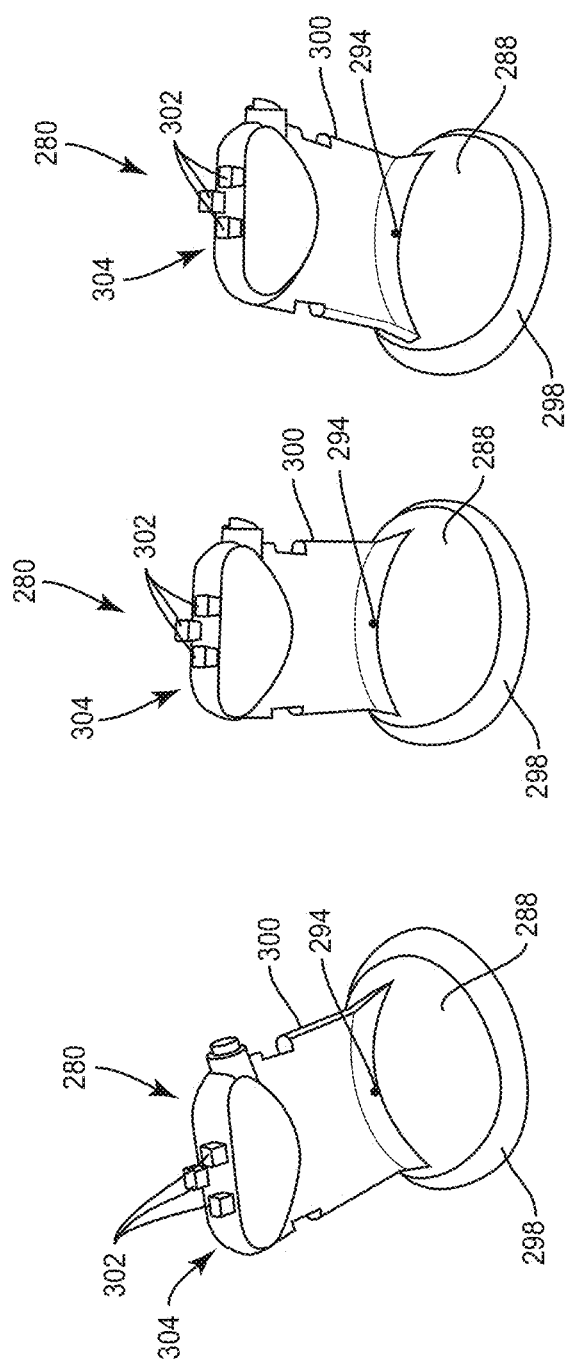

EYELID ILLUMINATION SYSTEMS AND METHOD FOR IMAGING MEIBOMIAN GLANDS FOR MEIBOMIAN GLAND ANALYSIS

PRIORITY APPLICATIONS

The present application claims priority to U.S. Provisional Patent Application Ser. No. 61/987,982 entitled "EYELID ILLUMINATION SYSTEMS AND METHODS FOR IMAGING MEIBOMIAN GLANDS FOR MEIBOMIAN GLAND ANALYSIS," filed on May 2, 2014, incorporated herein by reference in its entirety.

The present application claims priority to U.S. Provisional Patent Application Ser. No. 61/819,143 entitled "COMBINATION TEAR FILM INTERFEROMETRY AND MEIBOGRAPHY SYSTEM FOR SIMULTANEOUS DATA ACQUISITION," filed on May 3, 2013, incorporated herein by reference in its entirety.

The present application also claims priority to U.S. Provisional Patent Application Ser. No. 61/819,201 entitled "LID FLIPPING TRANS-ILLUMINATOR," filed on May 3, 2013, incorporated herein by reference in its entirety.

The present application also claims priority to U.S. Provisional Patent Application Ser. No. 61/904,562 entitled "OCULAR SURFACE INTERFEROMETRY (OSI) SYSTEM AND METHODS FOR IMAGING, PROCESSING, AND/OR DISPLAYING AN OCULAR TEAR FILM AND MEIBOMIAN GLAND FEATURES," filed on Nov. 15, 2013, incorporated herein by reference in its entirety.

RELATED APPLICATIONS

The present application is related to U.S. patent application Ser. No. 12/798,275 entitled "OCULAR SURFACE INTERFEROMETRY (OSI) DEVICES AND SYSTEMS FOR IMAGING, PROCESSING, AND/OR DISPLAYING AN OCULAR TEAR FILM," filed on Apr. 1, 2010, issued as U.S. Pat. No. 8,746,883, which claims priority to U.S. Provisional Patent Application Ser. No. 61/211,596 entitled "OCULAR SURFACE INTERFEROMETRY (OSI) METHODS FOR IMAGING, PROCESSING, AND/OR DISPLAYING AN OCULAR TEAR FILM," filed on Apr. 1, 2009, which are both incorporated herein by reference in their entireties.

The present application is also related to U.S. patent application Ser. No. 12/798,275 entitled "OCULAR SURFACE INTERFEROMETRY (OSI) DEVICES AND SYSTEMS FOR IMAGING, PROCESSING, AND/OR DISPLAYING AN OCULAR TEAR FILM," filed on Apr. 1, 2010, which claims priority to U.S. Provisional Patent Application Ser. No. 60/211,596 entitled "OCULAR SURFACE INTERFEROMETRY (OSI) METHODS FOR IMAGING, PROCESSING, AND/OR DISPLAYING AN OCULAR TEAR FILM," filed on Apr. 1, 2009, which are both incorporated herein by reference in their entireties.

The present application is also related to U.S. patent application Ser. No. 12/798,326 entitled "OCULAR SURFACE INTERFEROMETRY (OSI) METHODS FOR IMAGING AND MEASURING OCULAR TEAR FILM LAYER THICKNESS(ES)," filed on Apr. 1, 2010, issued as U.S. Pat. No. 8,092,023, which claims priority to U.S. Provisional Patent Application Ser. No. 60/211,596 entitled "OCULAR SURFACE INTERFEROMETRY (OSI) METHODS FOR IMAGING, PROCESSING, AND/OR DISPLAYING AN OCULAR TEAR FILM," filed on Apr. 1, 2009, which are both incorporated herein by reference in their entireties.

The present application is also related to U.S. patent application Ser. No. 12/798,324 entitled "OCULAR SURFACE INTERFEROMETRY (OSI) DEVICES AND SYSTEMS FOR IMAGING AND MEASURING OCULAR TEAR FILM LAYER THICKNESS(ES)," filed on Apr. 1, 2010, issued as U.S. Pat. No. 8,215,774, which claims priority to U.S. Provisional Patent Application Ser. No. 60/211,596 entitled "OCULAR SURFACE INTERFEROMETRY (OSI) METHODS FOR IMAGING, PROCESSING, AND/OR DISPLAYING AN OCULAR TEAR FILM," filed on Apr. 1, 2009, which are both incorporated herein by reference in their entireties.

The present application is also related to U.S. patent application Ser. No. 11/540,422 entitled "MEIBOMIAN GLAND IMAGING," filed on Sep. 9, 2006, issued as U.S. Pat. No. 8,249,695, which is incorporated herein by reference in its entirety.

The present application is also related to U.S. patent application Ser. No. 11/893,669 entitled "MEIBOMIAN GLAND ILLUMINATING AND IMAGING," filed on Aug. 17, 2007, issued as U.S. Pat. No. 8,255,039, which is a continuation-in-part of U.S. patent application Ser. No. 11/540,422 entitled "MEIBOMIAN GLAND IMAGING," filed on Sep. 9, 2006, issued as U.S. Pat. No. 8,249,695, which are both incorporated herein by reference in their entireties.

The present application is being filed with color versions (3 sets) of the drawings discussed and referenced in this disclosure. Color drawings more fully disclose the subject matter disclosed herein.

FIELD OF THE DISCLOSURE

The technology of the disclosure relates to imaging of meibomian glands for performing meibomian gland analysis to diagnose meibomian gland dysfunction (MGD).

BACKGROUND

In the human eye, the precorneal tear film covering ocular surfaces is composed of three primary layers: the mucin layer, the aqueous layer, and the lipid layer. Each layer plays a role in the protection and lubrication of the eye and thus affects dryness of the eye or lack thereof. Dryness of the eye is a recognized ocular disease, which is generally referred to as "dry eye," "dry eye syndrome" (DES), or "keratoconjunctivitis sicca" (KCS). Dry eye can cause symptoms, such as itchiness, burning, and irritation, which can result in discomfort. There is a correlation between the ocular tear film layer thicknesses and dry eye disease. The various different medical conditions and damage to the eye as well as the relationship of the aqueous and lipid layers to those conditions are reviewed in Surv Opthalmol 52:369-374, 2007 and additionally briefly discussed below.

As illustrated in FIG. 1, the precorneal tear film includes an innermost layer of the tear film in contact with a cornea 10 of an eye 11 known as the mucus layer 12. The mucus layer 12 is comprised of many mucins. The mucins serve to retain aqueous in the middle layer of the tear film known as the aqueous layer. Thus, the mucus layer 12 is important in that it assists in the retention of aqueous on the cornea 10 to provide a protective layer and lubrication, which prevents dryness of the eye 11.

A middle or aqueous layer 14 comprises the bulk of the tear film. The aqueous layer 14 is formed by secretion of aqueous by lacrimal glands 16 and accessory tear glands 17 surrounding the eye 11, as illustrated in FIG. 2A. FIG. 2B illustrates the eye 11 in FIG. 2A during a blink. The aqueous, secreted by the lacrimal glands 16 and accessory tear glands 17, is also commonly referred to as "tears." One function of the aqueous layer 14 is to help flush out any dust, debris, or foreign objects that may get into the eye 11. Another important function of the aqueous layer 14 is to provide a protective layer and lubrication to the eye 11 to keep it moist and comfortable. Defects that cause a lack of sufficient aqueous in the aqueous layer 14, also known as "aqueous deficiency," are a common cause of dry eye. Contact lens wear can also contribute to dry eye. A contact lens can disrupt the natural tear film and can reduce corneal sensitivity over time, which can cause a reduction in tear production.

The outermost layer of the tear film, known as the "lipid layer" 18 and also illustrated in FIG. 1, also aids to prevent dryness of the eye. The lipid layer 18 is comprised of many lipids known as "meibum" or "sebum" that is produced by meibomian glands 20 in upper and lower eyelids 22, 24, as illustrated in FIG. 3. This outermost lipid layer is very thin, typically less than 250 nanometers (nm) in thickness. The lipid layer 18 provides a protective coating over the aqueous layer 14 to limit the rate at which the aqueous layer 14 evaporates. Blinking causes the upper eyelid 22 to mall up aqueous and lipids as a tear film, thus forming a protective coating over the eye 11. A higher rate of evaporation of the aqueous layer 14 can cause dryness of the eye. Thus, if the lipid layer 18 is not sufficient to limit the rate of evaporation of the aqueous layer 14, dryness of the eye may result.

Thus, because the meibomian glands 20 are responsible for secretion of lipids that reduce the evaporation rate of the aqueous layer 14, it may be desirable to evaluate the meibomian glands as part a dry eye diagnosis. For example, some meibomian glands 20 may be missing in either the upper eyelid 22 or the lower eyelid 24, thus contributing to the reduction in lipid layer production. Other meibomian glands 20 may be damaged and not able to produce lipids. In this regard, surface meibography has been employed to visualize the meibomian glands in a patient's eyelids. Surface meibography involves imaging (i.e., a photograph) the inside surface of a patient's eyelid to image individual meibomian glands within a patient's eyelid. In this regard, as shown in FIG. 4 for example, a meibography image 26 of a patient's lower eyelid 28 is shown. To capture the meibography image 26, the patient's lower eyelid 28 is inverted to expose the interior surface 30 of the lower eyelid 28. An infrared (IR) light source is employed to illuminate the interior surface 30 of the lower eyelid 28. Meibomian glands reflect IR light. Thus, the meibomian glands 32 can be visualized as typically white structures as seen in the two photographs in FIG. 4. The meibomian glands 32 can include a quantification of amount of meibomian glands 32 by color contrast to the non-gland areas, whether the meibomian glands 32 are continuous or blunted in shape, the relative space between the meibomian glands 32 or density of glands, and whether the meibomian glands 32 extend to the surface of the lower eyelid 28.

Surface meibography has limitations. For example, meibomian glands that are not near the interior surface of the eyelid may not appear in a meibography image, because overlaying tissue may block the reflection of IR light or reduce the signal to noise ratio of the reflected IR light. Thus, it is desired to find additional methods of imaging the meibomian glands that can provided enhanced imaging and improve the signal-to-noise ratio of meibomian glands in images.

SUMMARY

Embodiments disclosed herein include eyelid illumination systems and methods for imaging meibomian glands for meibomian gland analysis. Similarly, the embodiments described herein can be applied to the lacrimal gland and Gland of Wolfring, which are also contained within the eyelid and tissue surrounding the eye.

In one embodiment, a meibomian gland imaging (MGI) device is provided. The MGI device is configured to infrared (IR) trans-illuminate of a patient's eyelid and capture an image of the patient's eyelid when being IR trans-illuminated to capture a lid trans-illumination image to show the meibomian glands in the patient's eyelid. An IR light source is disposed on the outer surface of the patient's eyelid as the patient's eyelid is flipped downward to image the interior surface of the patient's eyelid. In this manner, the IR light trans-illuminates the patient's eyelid such that the IR light disposed on the outer surface of the patient's eyelid is reflected back towards the outer surface. Thus, the image of the interior surface of the patient's eyelid shows the meibomian gland in dark outlined areas whereas non-gland material is shown in light areas where the IR light passes. This provides a high contrast lid trans-illumination image of the meibomian glands in the patient's eyelid that is X-ray like. Meibomian glands that are not located near the interior surface of the eyelid, that would otherwise be more difficult to image using surface meibography, are trans-illuminated as dark areas in the image. The lid trans-illumination image of the meibomian glands can then be analyzed to determine if all meibomian glands are present and/or if any meibomian glands are damaged as part of a diagnosis of the patient, including dry eye diagnoses or other disease states such as those present with infection.

In this regard, in one embodiment, a method of trans-illuminating a meibomian gland in an eyelid of a patient to image the meibomian gland is provided. The method comprises directing an infrared (IR) light from an IR light source to the eyelid to IR trans-illuminate meibomian glands in the eyelid. The method also comprises imaging the eyelid with an imaging device during IR trans-illumination to produce an IR trans-illumination image of meibomian glands in the eyelid.

In another embodiment, a meibomian gland imaging system for lid trans-illumination imaging of meibomian glands in an eyelid of a patient is provided. The meibomian gland imaging system comprises an infrared (IR) light source configured to direct an IR light to the eyelid to IR trans-illuminate meibomian glands in the eyelid. The meibomian gland imaging system also comprises an imaging device configured to image the eyelid during IR trans-illumination. The meibomian gland imaging system also comprises a computer control system. The computer control system is configured to control the IR light source to direct the IR light to the eyelid to IR trans-illuminate meibomian glands in the eyelid. The computer control system is also configured to control the imaging device to image the eyelid during IR trans-illumination. The computer control system is also configured to receive the image of the eyelid during IR trans-illumination. The computer control system is also configured to store an IR trans-illumination image of meibomian glands in the eyelid from the received image of the eyelid during IR trans-illumination.

In another embodiment, a lid flipping device is provided. The lip flipping device can be provided as part of the MGI device or a standalone device. The lid flipping device comprises a lid flipping end anatomically shaped to fit the curvature of the eyelids in one embodiment, to assist in the grasping and flipping of the eyelid during imaging. The lid flipping device also contains a light source disposed on the lip flipping end that is configured to engage with the patient's eyelid for lid flipping such that the light source trans-illuminates the patient's eyelid. The light source may be an IR or visible spectrum light source. The light source can be disposed at the lid flipping end to form a light pipe. The light source disposed in the lid flipping device may be comprised of individual light sources, such as light emitting diodes (LEDs) for example, that are individually controllable by the MGI device. For example, the MGI device may individually control the intensity of each of the IR light sources to compensate for the nature curvature of the eyelid, since outer portions of a flipped eyelid will be located closer to the imaging device that central portions. In this manner, the eyelid can be trans-illuminated along its outer surface such that the trans-illuminated IR light is captured with equal intensity or substantially equal intensity by the imaging device in the MGI device. Alternatively, the focus of the light intensity can be directed by the operator to portions and segments of the meibomian glands for greater clarity in the diagnosis.

In this regard, in one embodiment, an eyelid flipping device is provided. The eyelid flipping device comprises a body having a first end and a second end. The eyelid flipping device also comprises a curved lid flipping end surface disposed on the first end, the curved lid flipping end surface configured to grasp and flip an eyelid. The eyelid flipping device also comprises a light source disposed in the body, the light source configured to generate a light. The eyelid flipping device also comprises an elongated slot disposed in the curved lid flipping end surface of the body to receive IR light from the light source to form an IR light pipe. The IR light pipe is configured to IR trans-illuminate the eyelid when the curved lid flipping end surface of the body is positioned to grasp and flip the eyelid.

In another embodiment, the MGI device is also configured to direct IR light to illuminate the interior surface of the patient's eyelid. The MGI device images the interior surface of the patient's eyelid while the interior surface is illuminated to obtain a surface meibography image of the patient's meibomian glands. The IR light reflects off the meibomian glands such that the meibomian glands are shown in lighter outlined areas whereas non-gland material is shown in darker areas, opposite of a lid trans-illumination image of the meibomian glands. The surface meibography image of the meibomian glands can then be analyzed to determine if all meibomian glands are present and/or if any meibomian glands are damaged as part of the diagnosis. Further, the surface meibography image of the meibomian glands can be combined with the lid trans-illumination image of the meibomian glands to provide an even higher contrast image of the meibomian glands for analysis.

In another embodiment, the MGI device may be configured to capture a lid-trans-illumination image of the patient's meibomian glands and a surface meibography image of the patient's meibomian glands. The patient's eyelid is flipped before being imaged by the MGI device. Alternatively, the meibomian glands can be imaged during the process of flipping or rolling the eyelids to image and review portions and segments of the meibomian glands in the locations where the curvature of the inside-out eyelid is being created by the lid flipping device. When capturing a lid-trans-illumination image of the patient's meibomian glands, the light source in the lid flipping device is activated to trans-illuminate the patient's eyelid from the outer surface of the patient's eyelid. When capturing a surface meibography image of the patient's meibomian glands, the light source in the lid flipping device is de-activated and IR illuminators on the MGI device are activated to IR illuminate the interior surface of the patient's eyelid flipped back or in the process of being flipped back. In this manner, one orientation of the patient in the MGI device with their eyelid to be imaged lid flipped can allow the MGI device to capture both a lid trans-illumination and surface meibography image of the patient's meibomian glands. This may also be desirable so that the eyelid is in the same or substantially same orientation with regard to the imaging device in the MGI device when capturing lid trans-illumination and surface meibography image of the patient's meibomian glands to more easily allow both images to be registered to each other for comparison and/or combining purposes. In addition, both images can be displayed on the same screen or split screen for the end user to review.

Further, because the surface meibography image of the meibomian glands may include glare from reflected light from the light source, in another embodiment, the MGI device may also be configured to capture two or more surface meibography images of the meibomian glands while illuminated from different angles such that any glare appears in different areas in each of two or more surface meibography images. The two or more surface meibography images can then be spliced together to provide a resulting surface meibography image with reduced glare.

In this regard, in another embodiment, a method of surface imaging meibomian glands in an eyelid of a patient is provided. The method comprises directing a first infrared (IR) light from a first IR light source at a first angle to a first angle end of an interior portion of an eyelid while not directing a second IR light from a second IR light source at a second angle, opposite the first angle, to the interior portion of the eyelid. The method also comprises directing the second IR light from the second IR light source at a second angle, opposite the first angle, to a second angle end of the interior portion of the eyelid while not directing the second IR light at the first angle to the interior portion of the eyelid. The method also comprises imaging the interior portion of an interior surface of the eyelid with an imaging device when the interior portion is illuminated with the first IR light at the first angle to produce a first surface meibography image of meibomian glands in the eyelid. The method also comprises imaging the interior portion of the interior surface of the eyelid with the imaging device when the interior portion is illuminated with the second IR light at the second angle to produce a second surface meibography image of meibomian glands in the eyelid. The method also comprises combining the second angle end of the first surface meibography image with the first angle end of the second surface meibography image to produce a surface meibography image having reduced glare resulting from imaged reflections of the second IR light from the interior portion of the interior surface of the eyelid.

Alternatively, more than two (2) IR light sources with resultant angles on the interior portion of the eyelid can be employed.

In another embodiment, a meibomian gland imaging system for surface imaging of meibomian glands in an eyelid of a patient is provided. The meibomian gland imaging system comprises a first infrared (IR) light source configured to direct a first IR light at a first angle to a first angle end of an interior portion of an eyelid. The meibomian gland imaging system also comprises a second IR light source configured to direct a second IR light at a second angle, opposite the first angle, to a second angle end of the interior portion of the eyelid while not directing the second IR light at the first angle to the interior portion of the eyelid. The meibomian gland imaging system also comprises an imaging device configured to image the interior portion of an interior surface of the eyelid. The meibomian gland imaging system also comprises a computer control system. The computer control system is configured to control the first IR light source to direct the first IR light at the first angle to the first angle end of the interior portion of the eyelid while not directing the second IR light from the second IR light source at the second angle, opposite the first angle, to the interior portion of the eyelid. The computer control system is also configured to control the second IR light source to direct the second IR light at the second angle to the second angle end of the interior portion of the eyelid while not directing the first IR light from the first IR light source at the first angle, opposite the second angle, to the interior portion of the eyelid. The computer control system is also configured to control the imaging device to image the interior portion of the interior surface of the eyelid in a first surface meibography image when the interior portion is illuminated with the second IR light at the first angle to produce a first surface meibography image of meibomian glands in the eyelid. The computer control system is also configured to control the imaging device to image the interior portion of the interior surface of the eyelid in a second surface meibography image when the interior portion is illuminated with the second IR light at the second angle to produce a second surface meibography image of meibomian glands in the eyelid. The computer control system is also configured to combine the second angle end of the first surface meibography image with the first angle end of the second surface meibography image to produce a resulting surface meibography image having reduced glare resulting from imaged reflections of the second IR light from the interior portion of the interior surface of the eyelid. The computer control system is also configured to store the resulting surface meibography image of meibomian glands in the eyelid.

In yet another embodiment, a mirrored scleral lens can be provided to facilitate providing lid trans-illumination of a patient's eyelid for lid trans-illumination imaging of meibomian glands without requiring eyelid flipping, rolling of the eyelid, or kinking the eyelid tissue in the process of flipping the eyelid. The mirrored scleral lens has an eyecup that is configured to be disposed on top of a patient's cornea. A mirrored outer surface is disposed on the exterior surface of the eyecup, such that the mirror surface is disposed towards the interior surface of a patient's eyelid when the eyecup is disposed on the patient's cornea. An external light source is used to direct light to the exterior surface of the patient's eyelid with the mirrored scleral lens disposed in the patient's eye and the eyelids closed over the mirrored surface to trans-illuminate the patient's eyelid. Alternatively, the mirrored scleral lens can be a self-contained unit without any external connection such that the LED lights and battery for providing the trans-illuminating light are provided within the scleral lens body. Due to size limitations, the battery for the LED lights would be limited in duration and LEDs would be low profile and printed into the body of the scleral lens. In either case, the trans-illuminated light is reflected from the mirrored surface back to one or more cameras installed in the eyecup to receive the reflected light and provide a trans-illumination image thereof to a control system.

In another embodiment, a mirrored scleral lens for trans-illuminating meibomian glands in a patient's eyelid is provided. The mirrored scleral lens comprises an eyecup having an interior surface and an exterior surface, the interior surface configured to be disposed on a cornea of a patient's eye. The mirrored scleral lens also comprises a platform attached to the eyecup such that the platform extends away from the patient's eye when the eyecup is disposed on the cornea. The mirrored scleral lens also comprises a mirrored surface disposed on at least a portion of the exterior surface of the eyecup such that the mirrored surface is disposed adjacent to the interior surface of the patient's eyelid when the eyelid is closed over the eyecup. The mirrored scleral lens also comprises a camera disposed in the platform, the camera configured to receive reflected light from the mirrored surface. The mirrored surface is configured to reflect received light trans-illuminating the patient's eyelid to the mirrored surface. The camera is configured to receive the trans-illumination light reflected from the mirrored surface to capture a trans-illumination image of the patient's eyelid.

Those skilled in the art will appreciate the scope of the present disclosure and realize additional aspects thereof after reading the following detailed description of the preferred embodiments in association with the accompanying drawing figures.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The accompanying drawing figures incorporated in and forming a part of this specification illustrate several aspects of the invention, and together with the description serve to explain the principles of the invention.

FIG. 6C is a side view of a patient positioned to the MGI device through the assistance of a chin rest to prepare the patient's eyelid and meibomian glands therein to be imaged;

FIGS. 16A-16C illustrate the surface meibography and lid trans-illumination images of FIGS. 14A and 14B, and a combined surface meibography/lid trans-illumination image of the images in FIGS. 14A and 14B, respectively, to illustrate the higher contrast image of the meibomian glands in the combined image;

FIGS. 25A-25C are schematic diagrams of mirrored scleral lens devices illustrated from different angles.

DETAILED DESCRIPTION

The embodiments set forth below represent the necessary information to enable those skilled in the art to practice the disclosure and illustrate the best mode of practicing the disclosure. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It is to be understood that the disclosure is not to be limited to the specific embodiments disclosed and that modifications and other embodiments are intended to be included within the scope of the appended claims. It is intended that the present disclosure cover the modifications and variations of this disclosure provided they come within the scope of the appended claims and their equivalents. Although specific terms are employed herein, they are used in a generic and descriptive sense only and not for purposes of limitation.

Embodiments disclosed herein include eyelid illumination systems and methods for imaging meibomian glands for meibomian gland analysis. In one embodiment, a meibomian gland imaging (MGI) device is provided. The MGI device is configured to infrared (IR) trans-illuminate of a patient's eyelid and capture an image of the patient's eyelid when being IR trans-illuminated to capture a lid trans-illumination image to show the meibomian glands in the patient's eyelid. An IR light source is disposed on the outer surface of the patient's eyelid as the patient's eyelid is flipped downward to image the interior surface of the patient's eyelid. In this manner, the IR light trans-illuminates the patient's eyelid such that the IR light disposed on the outer surface of the patient's eyelid is reflected back towards the outer surface. Thus, the image of the interior surface of the patient's eyelid shows the meibomian gland in dark outlined areas whereas non-gland material is shown in light areas where the IR light passes. This provides a high contrast lid trans-illumination image of the meibomian glands in the patient's eyelid that is X-ray like. Meibomian glands that are not located near the interior surface of the eyelid, that would otherwise be more difficult to image using surface meibography, are trans-illuminated as dark areas in the image. The lid trans-illumination image of the meibomian glands can then be analyzed to determine if all meibomian glands are present and/or if any meibomian glands are damaged as part of a diagnosis of the patient, including dry eye diagnoses and other disease states such as infection.

Figure 1:
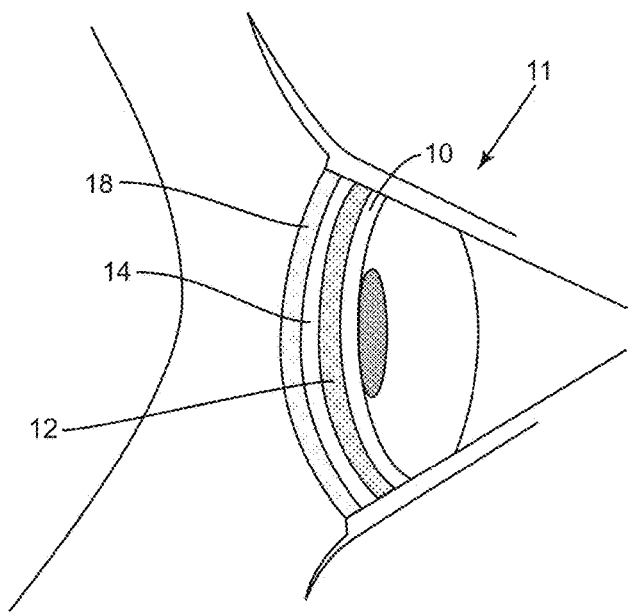
FIG. 1 is a side view of an exemplary eye showing the three layers of the tear film in exaggerated form.
Figure 2A:
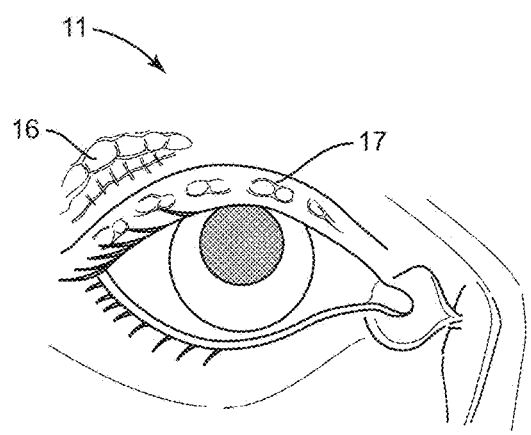
FIG. 2A is a front view of an exemplary eye showing the lacrimal and accessory tear glands that produce aqueous in the eye.
Figure 2B:
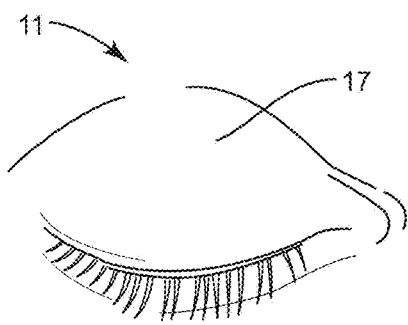
FIG. 2B is a front view of an exemplary eye in FIG. 2A during a blink.
Figure 3:
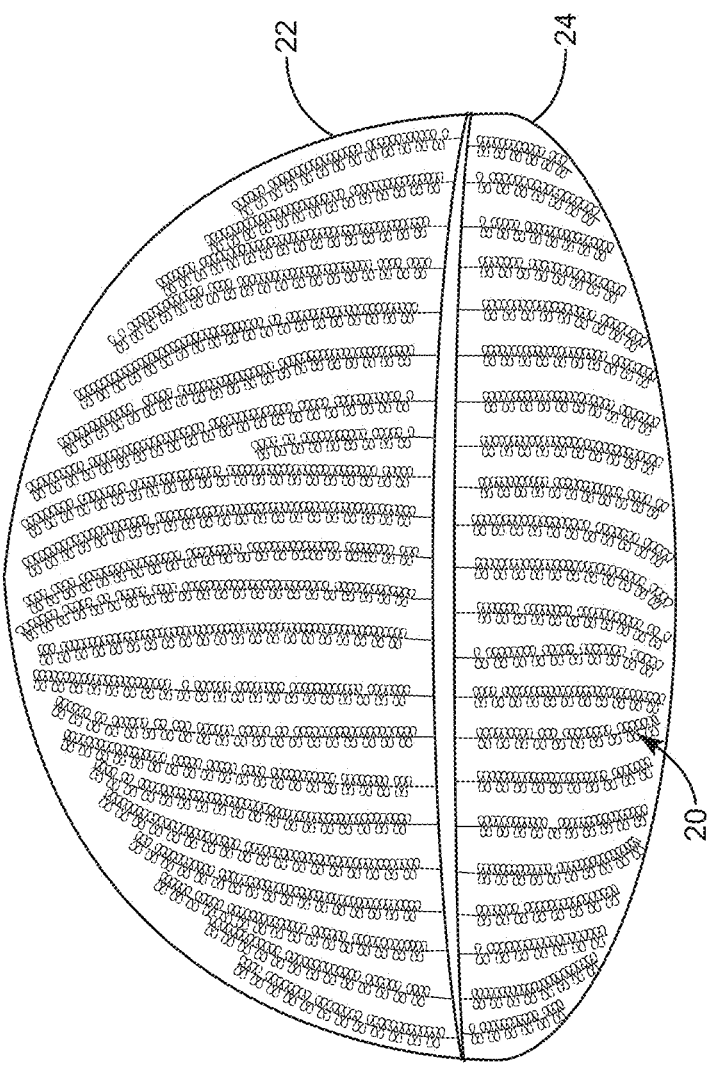
FIG. 3 illustrates exemplary upper and lower eyelids showing the meibomian glands contained therein.
Figure 4:
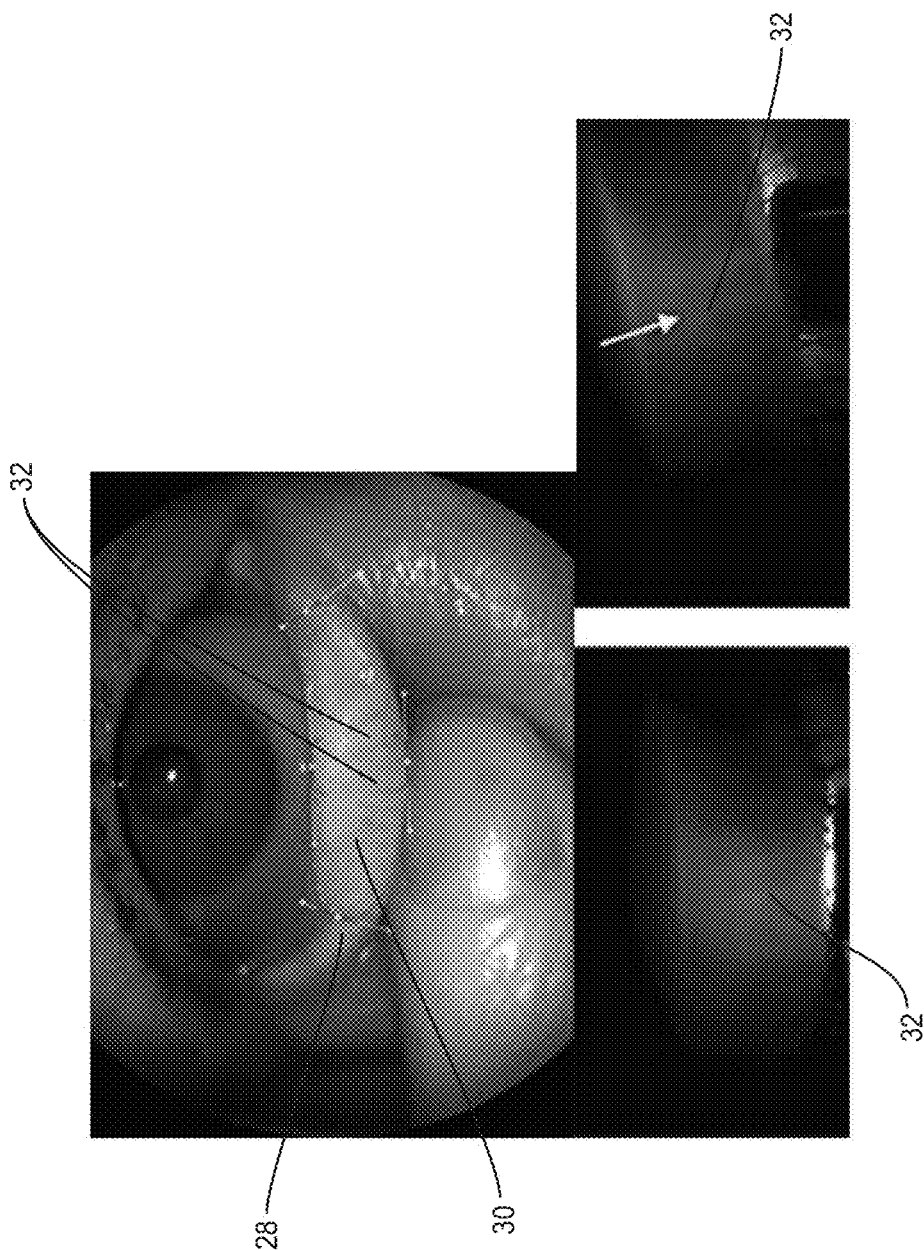
FIG. 4 illustrates a patient's lower eyelid flipped and illuminated with an infrared (IR) light for surface meibography and photographs of the interior surface of the eyelid to show the meibomian glands in the eyelid.
Figure 5A:
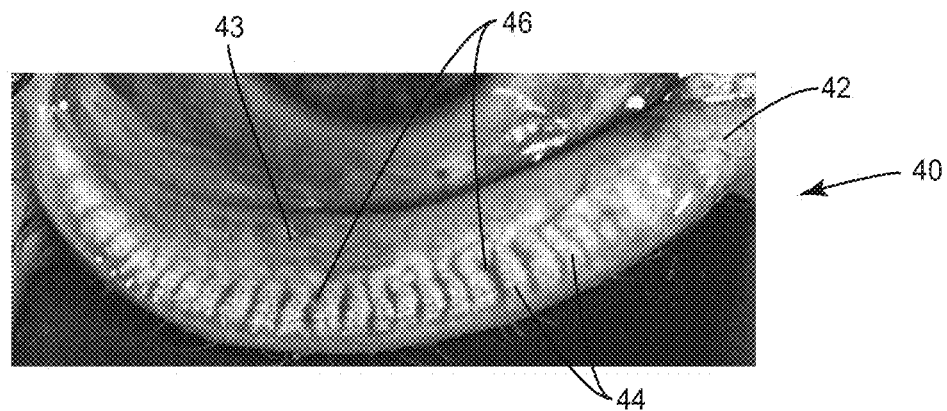
FIG. 5A is a surface meibography image of a patient's eyelid illustrating improved contrast between the meibomian glands and the non-gland area in the patient's eyelid.

In this regard, FIG. 5A is a surface meibography image 40 of a patient's lower eyelid 42 when the interior surface 43 of the lower eyelid 42 is illuminated by infrared (IR) light as the lower eyelid 42 is flipped backwards. As shown, the IR light is reflected by the meibomian glands 44 contained in the lower eyelid 42, such that the meiboiman glands 44 appear as light or white colored areas in the surface meibography image 40. Non-gland area 46 in the lower eyelid 42 appear as darker or black areas in the surface meibography image 40, because these areas do not tend to reflect the IR light. The surface meibography image 40 can be analyzed by a doctor or technician to understand the nature of the patient's meibomian glands 44. Similarly, this approach can be employed for lacrimal glands and the Gland of Wolfring diagnosis. For example, the surface meibography image 40 can be analyzed to determine if any meibomian glands 44 are missing, or truncated, or have "dropped out" or disappeared from atrophy. Thus, as an example, this may be the underlying cause for reduced lipids present in the patient's eye, as opposed to the meibomian glands 44 being present, but possibly obstructed to explain the lack of lipid production contributing to a dry eye condition. The surface meibography image 40 can also be analyzed to understand information about the shape, quantity, and quality of the meibomian glands 44. However, surface meibography has limitations. For example, if any meibomian glands in the lower eyelid 42 are not near the interior surface of the lower eyelid 42, those meibomian glands may not appear in the surface meibography image 40. For example, overlaying tissue in the lower eyelid 42 may block the reflection of IR light or reduce the signal to noise ratio of reflected IR light from certain meibomian glands in the patient's lower eyelid 42. Thus, it is desired to find additional methods of imaging the meibomian glands that can provided enhanced imaging and improve the signal-to-noise ratio of meibomian glands in images.

Figure 5B:
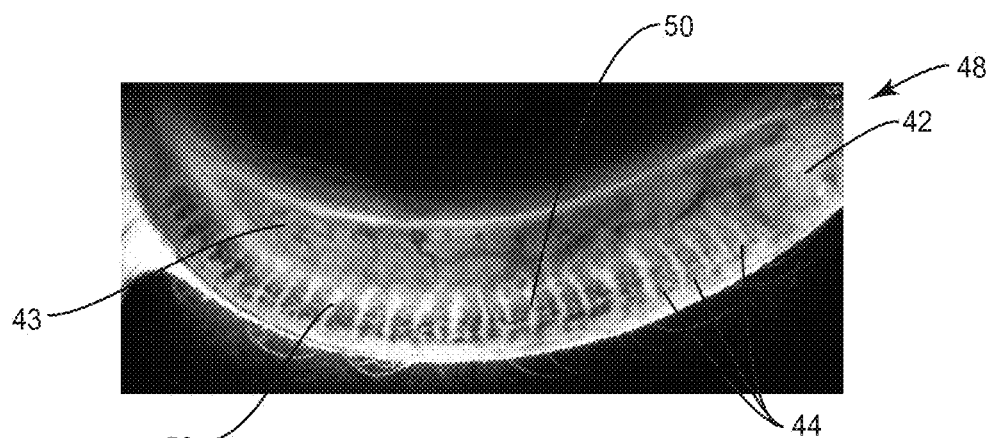
FIG. 5B is a lid IR trans-illumination image of meibomian glands in an eyelid, where IR light was disposed on an outer surface of the eyelid and directed towards the interior surface of the eyelid with the eyelid flipped, to trans-illuminate the eyelid such that the meibomian glands are shown as dark areas due to the reflection of IR light back towards the outer surface of the eyelid.

In this regard, FIG. 5B is an IR trans-illumination image 48 of the same patient's lower eyelid 42 in FIG. 5A when the eyelid is flipped downward and trans-illuminated from an exterior surface of the patient's lower eyelid 42. Exemplary illumination systems and methods that can capture and analyze a lid IR trans-illumination image, like the lid IR trans-illumination image 48 in FIG. 5B, are discussed in more detail below in this disclosure. With regard to FIG. 5B, when the lower eyelid 42 is IR trans-illuminated, the IR light is directed through the exterior surface of the lower eyelid 42 to the interior surface 43 of the eyelid. The IR light reflects off of the meibomian glands 44 back towards the exterior surface of the lower eyelid 42, such that the darker or black area in the IR trans-illumination image 48 indicates the presence of the meibomian glands 44 in the lower eyelid 42. The lighter or white areas in the IR trans-illumination image 48 indicate non-gland material 50 in the lower eyelid 42. Thus, the IR trans-illumination image 48 is an X-ray like image that causes the meibomian glands 44 to show up in reverse light from the surface meibography image 40 in FIG. 5A. The IR trans-illumination image 48 may include a higher contrast image of the meibomian glands 44 than the surface meibography image 40 in FIG. 5A, thus further and better assisting a doctor or technician in the viewing and analysis of the patient's meibomian glands 44.

Figure 5C:
FIG. 5C is a resulting image of the surface meibography image in FIG. 5A with the lid IR trans-illumination image in FIG. 5B to further improve the contrast between meibomian glands and the non-gland areas in an image of the patient's eyelid.

Also, as will be discussed in more detail below, an even higher contrast image of the meibomian glands 44 in the patient's lower eyelid 42 in FIGS. 5A and 5B may be achieved by combining or subtracting the IR trans-illumination image 48 in FIG. 5B with the surface meibography image 40 in FIG. 5A. Eyelid illumination systems and methods for performing this function are discussed in more detail below, but such is shown in FIG. 5C. FIG. 5C is a resulting image 52 of the surface meibography image 40 in FIG. 5A with the IR trans-illumination image 48 in FIG. 5B ("resulting combined surface meibography and IR trans-illumination image 52") to further improve the contrast between meibomian glands 44 and the non-gland areas 46, 50 in the resulting image 52. As shown in FIG. 5C, the meibomian glands 44 appear in lighter or white areas, but with higher contrast than the meibomian glands 44 appear in the surface meibography image 40 in FIG. 5A. Thus, the resulting combined surface meibography and IR trans-illumination image 52 may further assist a doctor or technician in analyzing the meibomian glands and diagnosing possible conditions as a result, such as dry eye.

Figure 6A:
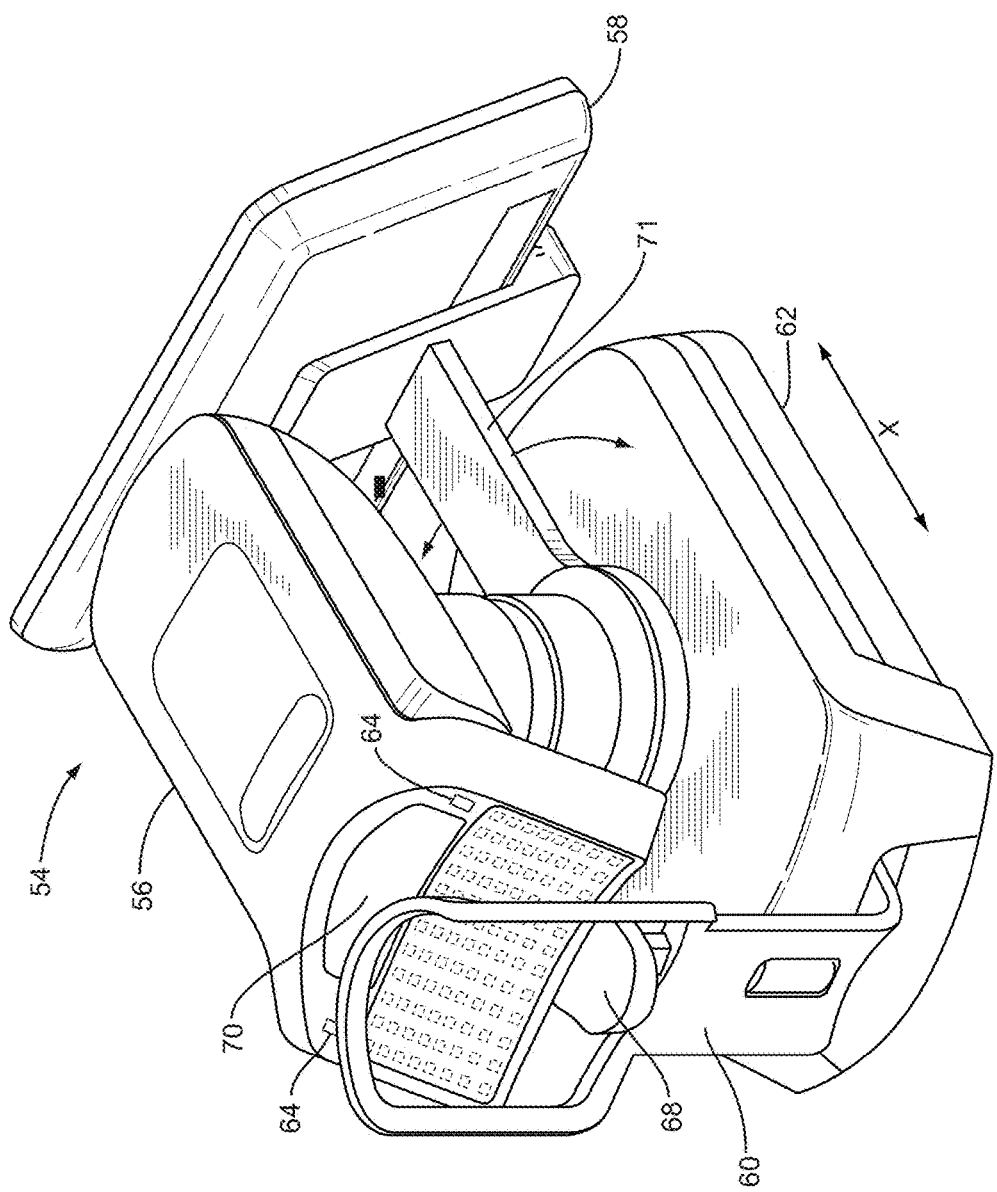
FIG. 6A is a perspective view of an exemplary meibomian gland imaging (MGI) device capable of performing both surface meibography and lid trans-illumination imaging of a patient's eyelids and meibomian glands therein, such as illustrated in FIGS. 5A and 5B, respectively, and a resulting surface meibography/lid trans-illumination image, such as illustrated in FIG. 5C.
Figure 6B:
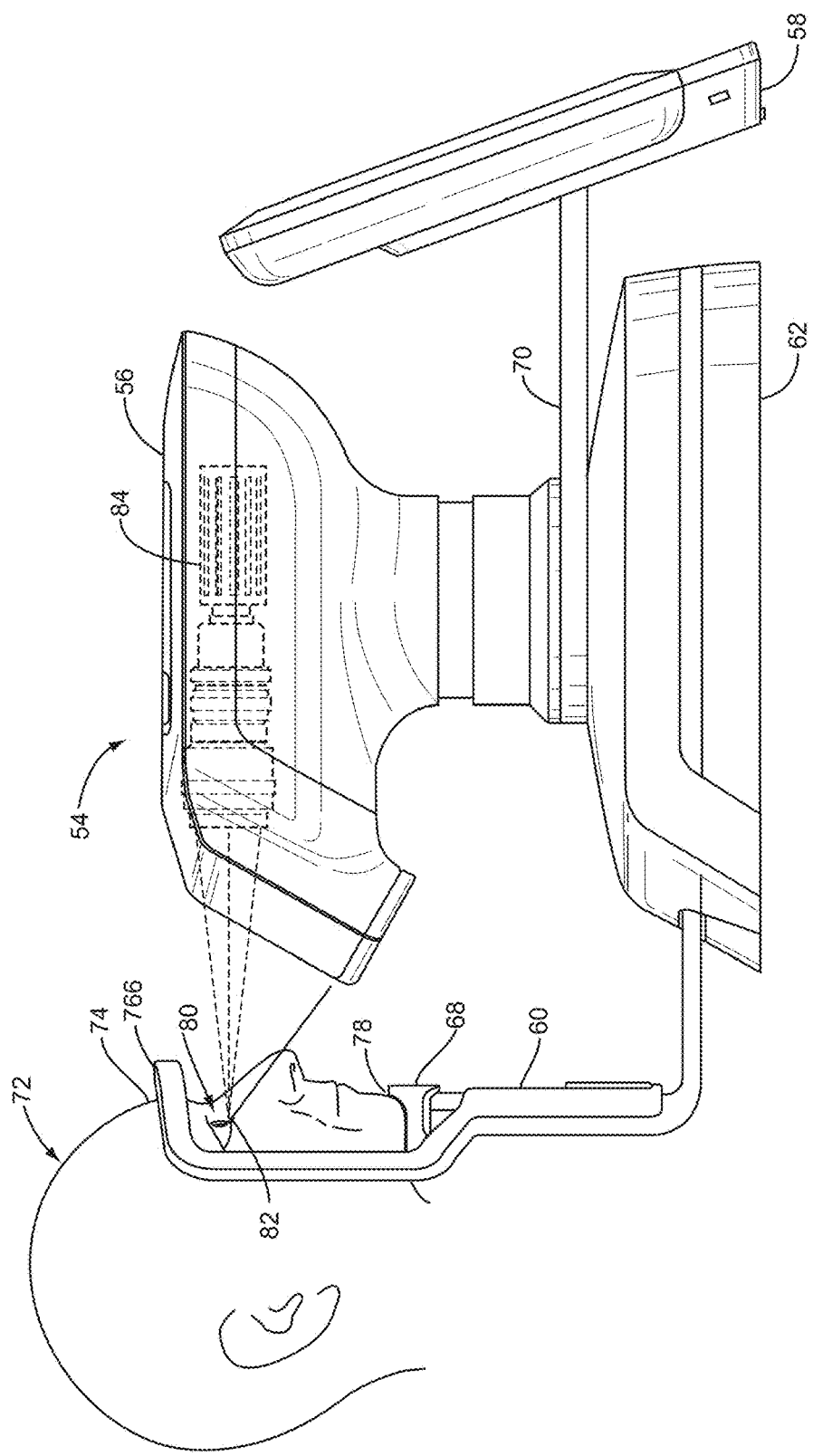
FIG. 6B is a side view of exemplary internal components of the MGI device in FIG. 6A, further illustrating an IR light source for illuminating a patient's eyelids and a camera device for performing both surface meibography and lid trans-illumination imaging of the patient's meibomian glands.

FIGS. 6A-6C illustrate an example meibomian gland imaging (MGI) device 54 capable of performing both surface meibography and IR trans-illumination imaging of a patient's eyelids and meibomian glands therein to capture surface meibography images and IR trans-illumination images of the patient's eyelid, such as those illustrated in FIGS. 5A-5C above. This MGI device 54 will now be described in more detail.

FIG. 6A illustrates a perspective view of the MGI device 54. The MGI device 54 is designed to facilitate imaging of a patient's eyelid and the meibomian glands disposed therein, and processing and analyzing the images to determine characteristics of the patient's meibomian glands. In this regard, the MGI device 54 includes an imaging device and light source as will be described in more detail below. As illustrated in FIG. 6A, the MGI device 54 is comprised generally of a housing 56, a display monitor ("display") 58, and a patient head support 60. The housing 56 may be designed for table top placement. The housing 56 rests on a base 62 in a fixed relationship. As will be discussed in more detail below, the housing 56 houses an imaging device and other electronics, hardware, and software to allow a clinician to surface illuminate and trans-illuminate a patient's eyelid to capture surface meibography and IR trans-illumination images of meibomian glands. An IR light source 64 (also referred to herein as "IR illuminator 64") is also provided in the housing 56 to allow for IR surface illumination and/or IR trans-illumination of a patient's eyelid.

To image a patient's eyelid, the patient places his or her head in the patient head support 60 and rests his or her chin on a chin rest 68. The chin rest 68 can be adjusted to align the patient's eye and tear film with the IR light source 64 inside the housing 56, as will be discussed in more detail below. The chin rest 68 may be designed to support up to two (2) pounds of weight, but such is not a limiting factor. A transparent window 70 allows the imaging device inside the housing 56 to have a clear line of sight to a patient's eyelid when the patient's head is placed in the patient head support 60. The MGI device 54 is designed to image one eyelid at a time, but can be configured to image more than one eyelid of a patient at a time, if desired.

In general, the display 58 can provide an input and output device for the MGI device 54. For example, a user interface can be provided on the display 58 for the clinician to interact with a control system provided in the housing 56 that controls the operation of the MGI device 54, to operate the MGI device 54. For example, the user interface can allow a clinician to control imaging positioning, focus of the imaging device, and other settings of the imaging device for capturing images of a patient's eyelid. As will be discussed in more detail below, the control system may include a general purpose microprocessor or computer with memory for storage of data, including images of the patient's eye and tear film. The microprocessor should be selected to provide sufficient processing speed to process images of the patient's tear film and generate output characteristic information about the tear film (e.g., one minute per twenty second image acquisitions). The control system may control synchronization of activation of the light source and the imaging device to capture images of the patient's eyelid when properly illuminated. Various input and output ports and other devices can be provided, including but not limited to a joystick for control of the imaging device, USB ports, wired and wireless communication including Ethernet communication, a keyboard, a mouse, speaker(s), computer memory for storing or transmitting patient data, foot pedals, voice activated controls, etc. A power supply is provided inside the housing 56 to provide power to the components therein requiring power. A cooling system, such as a fan, may also be provided to cool the MGI device 54 from heat generating components therein.

To allow for human diagnosis of the patient's eyelid and meibomian glands disposed therein, images of the patient's eyelid can be taken by the imaging device in the housing 56 of the MGI device 54 and displayed on the display 58 for review by a clinician, as will be illustrated and described in more detail below. The images displayed on the display 58 may be real-time images being taken by the imaging device, or may be previously recorded images stored in memory. To allow for different orientations of the MGI device 54 to provide a universal configuration for manufacturing, the display 58 can be rotated about the base 62. The display 58 is attached to a monitor arm 71 shown that is rotatable about the base 62, as illustrated in FIGS. 6A and 6B. The display 58 can be placed opposite of the patient head support 60, as illustrated in FIG. 6B, if the clinician desires to sit directly across from the patient. Alternatively, display 58 can be rotated either left or right about the X-axis to be placed adjacent to the patient head support 60. The display 58 may be a touch screen monitor to allow a clinician or other user to provide input and control to the control system inside the housing 56 directly via touch of the display 58 for control of the MGI device 54. The display 58 illustrated in FIGS. 6A and 6B is a fifteen inch (15") flat panel liquid crystal display (LCD). However, the display 58 may be provided of any type or size, including but not limited to a cathode ray tube (CRT), plasma, LED, OLED, projection system, etc.

FIG. 6B illustrates a side view of the MGI device 54 of FIG. 6A to further illustrate imaging of an eyelid of a patient's eye 80. As illustrated therein, a patient places their head 72 in the patient head support 60. More particularly, the patient places their forehead 74 against a headrest 76 provided as part of the patient head support 60. The patient places their chin 78 in the chin rest 68. The patient head support 60 is designed to facilitate alignment of a patient's eyelid 82 with the MGI device 54, and in particular, an imaging device 84 (and illuminator) shown as being provided inside the housing 56. The chin rest 68 can be adjusted higher or lower to move the patient's eyelid 82 with respect to the MGI device 54.

Figure 7:
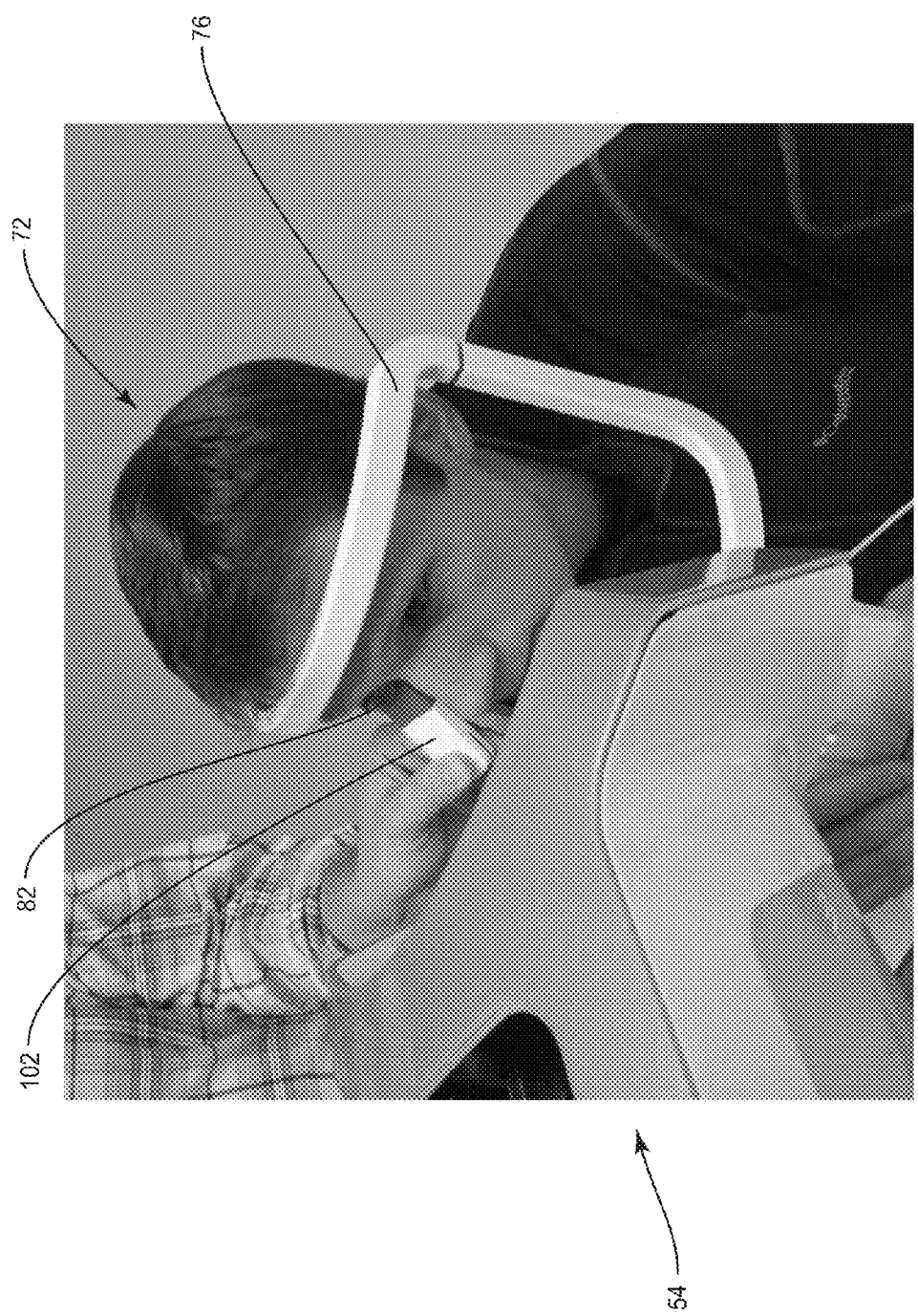
FIG. 7 illustrates a patient's lower eyelid being imaged by the MGI device in FIG. 6A while the lower eyelid is flipped downward through use of a lid flipping device as part of the MGI device.
Figure 8:
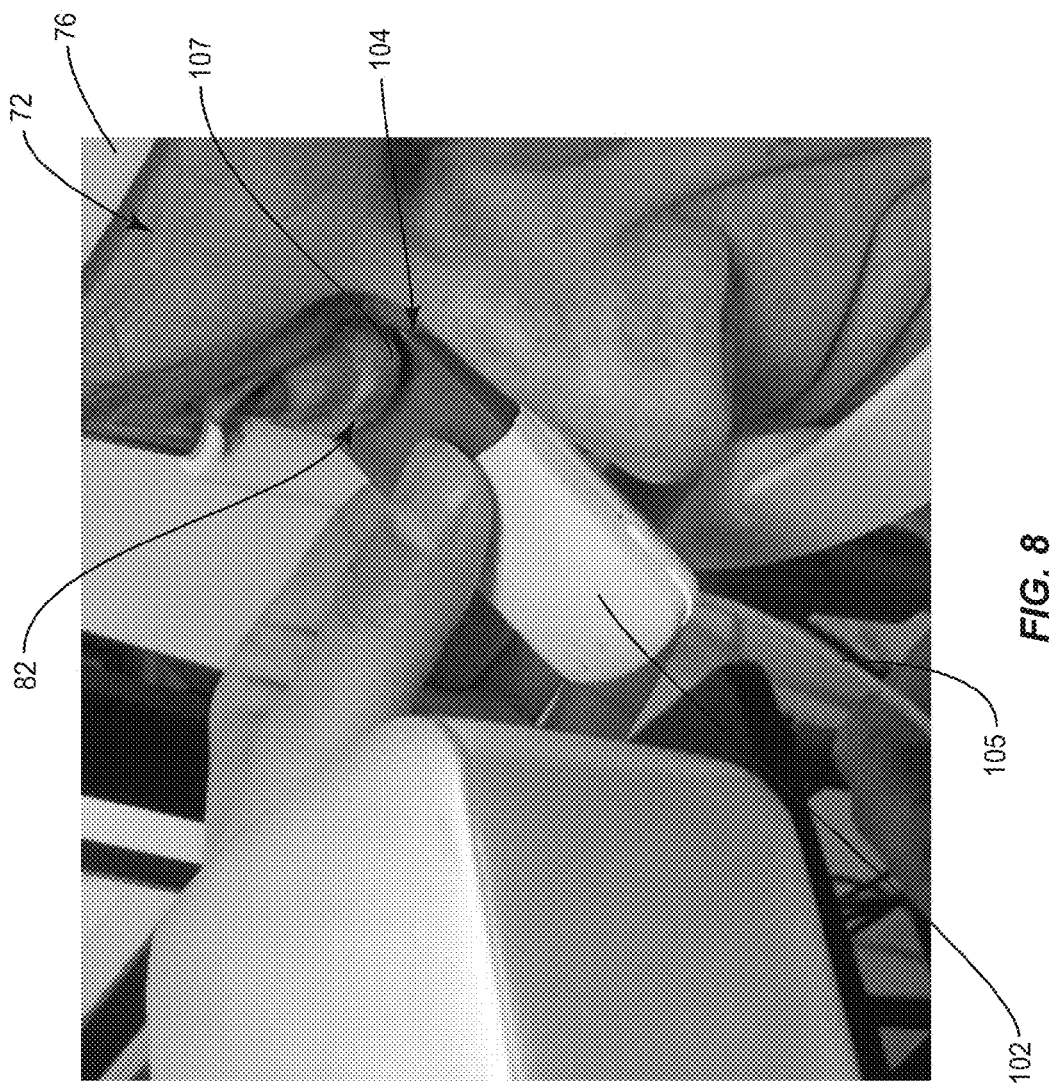
FIG. 8 illustrates a close-up view of a patient's lower eyelid being imaged by the MGI device in FIG. 6A while the lower eyelid is flipped downward through use of the lid flipping device.

As shown in FIG. 6C, the imaging device 84 is used to image the patient's eyelid 82 to determine characteristics of the patient's meibomian glands. If IR imaging is performed, the imaging device 84 includes the ability to capture IR light and/or IR filters are removed from the imaging device 84 to allow receipt of IR light. In particular, the imaging device 84 is used to capture reflected and other light from the patient's eyelid 82 when flipped downward by a handheld lid flipping device 102, as shown in FIG. 7, and illuminated by the IR light sources 64A, 64B to capture a surface meibography image, such as shown in FIG. 5A discussed above as an example. As shown in FIG. 7 and as will be discussed in more detail below, the lip flipping device 102 is configured and shaped to allow a clinician to grasp and flip the patient's eyelid 82 down (if a lower eyelid) or up (if an upper eyelid) to expose the interior surface of the eyelid 82 for surface meibography imaging. However, as shown in FIG. 8, as well also be discussed in more detail below, the lid flipping device 102 also has a dual purpose. The handheld lid flipping device 102 also contains an IR light source 104 that can be controlled to be activated by the MGI device 54 through an interface cable 105, when desired, to trans-illuminate the patient's flipped eyelid 82 from the exterior surface of the eyelid 82 to the interior surface 107 of the eyelid 82. In this manner, the imaging device 84 can also capture an IR trans-illumination image of the eyelid 82, such as shown in FIG. 5B discussed above, as an example. Alternatively, the IR light source 104 can be controlled to be through wireless communications (e.g. control circuit) to the lid flipping device 102. Thus, the MGI device 54 is configured to facilitate both surface IR illumination of the interior surface 107 of the eyelid 82 with IR illuminators 64A, 64B and IR trans-illumination of the eyelid 82 with the IR light source 104 built-in to the lid flipping device 102 to facilitate the imaging device 84 capturing both surface meibography and IR trans-illumination images of the eyelid 82 and the meibomian glands disposed therein.

In the MGI device 54, the imaging device 84 is a charge coupling device (CCD) digital video camera 86, but many types of metrological grade cameras or imaging devices can be provided. A CCD camera enjoys characteristics of efficient light gathering, linear behavior, cooled operation, and immediate image availability. A linear imaging device is one that provides an output signal representing a captured image which is precisely proportional to the input signal from the captured image. Thus, use of a linear imaging device (e.g., gamma correction set to 1.0, or no gamma correction) provides undistorted images of the meibomian glands, which can then be analyzed. In this manner, the resulting images of the eyelid do not have to be linearized before analysis, thus saving processing time. Gamma correction can then be added to the captured linear images for human-perceptible display on a non-linear display 58 in the MGI device 54.

The video camera 86 is capable of producing lossless photograph images of the patient's eyelid 82. As illustrated in FIG. 6C, the video camera 86 has a depth of field defined by the angle between rays 88 and the lens focal length that allows the patient's eyelid 82 to be in focus. The video camera 86 has an external trigger support so that the video camera 86 can be controlled by a control system to image the patient's eyelid 82. The video camera 86 includes a lens that fits within the housing 56. The video camera 86 in this embodiment has a resolution of 640×480 pixels and is capable of frame rates up to sixty (60) frames per second (fps). The lens system employed in the video camera 86 images a 16×12 mm dimension in a sample plane onto an active area of a CCD detector within the video camera 86.

With continuing reference to FIG. 6C, a camera positioning system 90 is also provided in the housing 56 of the MGI device 54 to position the video camera 86 for imaging of the patient's eyelid 82. The camera positioning system 90 is under the control of a control system 100. In this manner, a clinician can manipulate the position of the video camera 86 to prepare the MGI device 54 to image the patient's eyelid 82. The camera positioning system 90 allows a clinician and/or control system to move the video camera 86 between different patients' eyelids 82, but can also be designed to limit the range of motion within designed tolerances. The camera positioning system 90 also allows for fine tuning of the video camera 86 position. The camera positioning system 90 includes a stand 92 attached to a base 94. A linear servo or actuator 96 is provided in the camera positioning system 90 and connected between the stand 92 and a camera platform 98 supporting the video camera 86 to allow the video camera 86 to be moved in the vertical (i.e., Y-axis) direction.

In this embodiment of the MGI device 54, the camera positioning system 90 may not allow the video camera 86 to be moved in the X-axis or the Z-axis (in and out of FIG. 6C), but the invention is not so limited. The IR illuminators 64A, 64B are also fixed with regard to the camera platform 98 such that the IR illuminators 64A, 64B maintain a fixed geometric relationship to the video camera 86. Thus, when the video camera 86 is adjusted to the patient's eyelid 82, the IR illuminators 64A, 64B are automatically adjusted to the patient's eyelid 82 in the same regard as well. This may be important to enforce a desired distance (d) and angle of illumination (Φ) of the patient's eyelid 82, as illustrated in FIG. 6C, to properly capture surface meibography and IR trans-illumination images of the patient's eyelid 82 at the proper angle of incidence, since the MGI device 54 may be programmed to assume a certain distance and certain angles of incidence.

Figure 9:
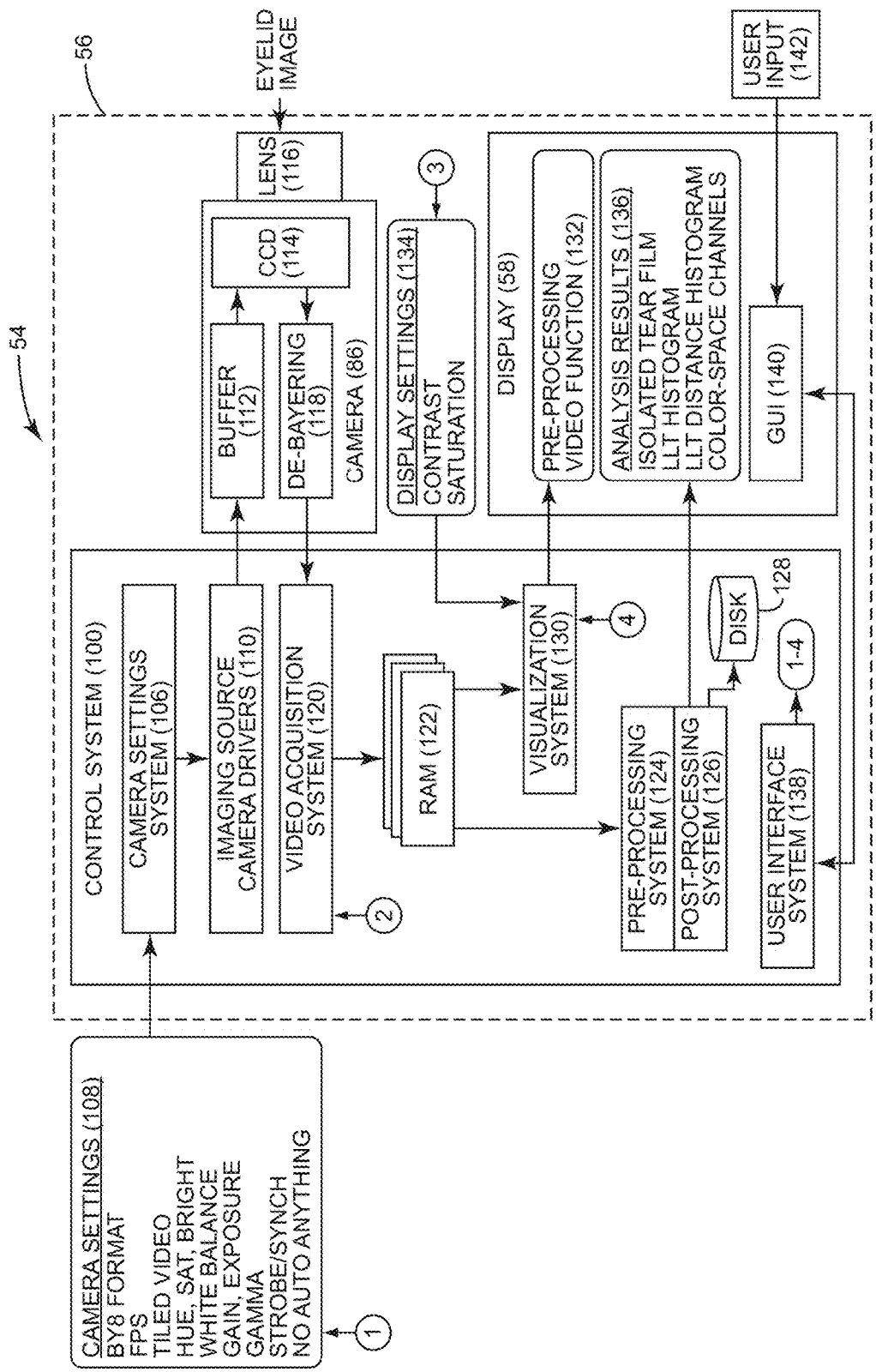
FIG. 9 illustrates an exemplary system diagram of a control system and supporting components in the MGI device in FIG. 6A.

Now that the basic imaging and illumination functions of the MGI device 54 have been described, FIG. 9 illustrates a system level diagram illustrating more detail regarding the control system and other internal components of the MGI device 54 provided inside the housing 56, according to one embodiment, to capture images of a patient's eyelid and process those images. As illustrated therein, the control system 100 is provided that provides the overall control of the MGI device 54. The control system 100 may be provided by any microprocessor-based or computer system. The control system 100 illustrated in FIG. 9 is provided in a system-level diagram and does not necessarily imply a specific hardware organization and/or structure. As illustrated therein, the control system 100 contains several systems. A camera settings system 106 may be provided that accepts camera settings from a clinician user. Exemplary camera settings 108 are illustrated, but may be any type according to the type and model of camera provided in the MGI device 54 as is well understood by one of ordinary skill in the art.

The camera settings 108 may be provided according to camera drivers 110, which may then be loaded into the video camera 86 upon initialization of the MGI device 54 for controlling the settings of the video camera 86. The settings and drivers may be provided to a buffer 112 located inside the video camera 86 to store the settings for controlling a CCD 114 for capturing ocular image information from a lens 116. Ocular images captured by the lens 116 and the CCD 114 are provided to a de-Bayering function 118 which contains an algorithm for post-processing of raw data from the CCD 114 as is well known. The ocular images are then provided to a video or still image acquisition system 120 in the control system 100 and stored in memory, such as random access memory (RAM) 122. The stored ocular images or signal representations can then be provided to a pre-processing system 124 and a post-processing system 126 to manipulate the ocular images to analyze the information therein regarding the imaged meibomian glands. The post-processed eyelid images and information may also be stored in mass storage, such as disk memory 128, for later retrieval and viewing on the display 58.

The control system 100 may also contain a visualization system 130 that provides the eyelid images to the display 58 to be displayed in human-perceptible form on the display 58. Before being displayed, the eyelid images may be pre-processed in a pre-processing video function 132. For example, if the eyelid images are provided by a linear camera, non-linearity (i.e. gamma correction) may have to be added in order for the ocular images to be properly displayed on the display 58. Further, contrast and saturation display settings 134, which may be controlled via the display 58 or a device communicating to the display 58, may be provided by a clinician user to control the visualization of ocular images displayed on the display 58. The display 58 is also adapted to display analysis result information 136 regarding the patient's eyelid, as will be described in more detail below. The control system 100 may also contain a user interface system 138 that drives a graphical user interface (GUI) utility 140 on the display 58 to receive user input 142. The user input 142 can include any of the settings for the MGI device 54, including the camera settings 108, the display settings 134, the visualization system 130 enablement, and video acquisition system 120 enablement, labeled 1-4. The GUI utility 140 may only be accessible by authorized personnel and used for calibration or settings that would normally not be changed during normal operation of the MGI device 54 once configured and calibrated.

Figure 10:
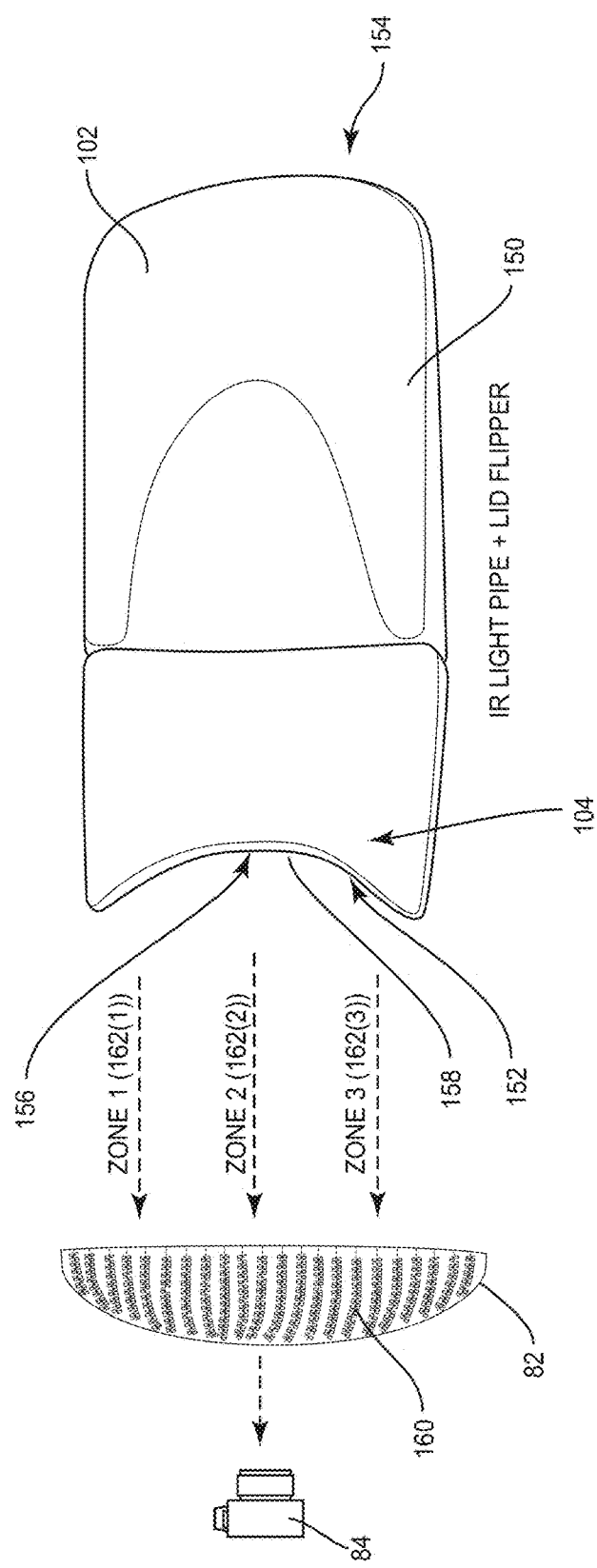
FIG. 10 is a schematic diagram of an exemplary lid flipping device that can be used with the MGI device in FIG. 6A, wherein the lip flipping device includes an integrated IR light pipe for trans-illuminating a patient's eyelid while the patient's eyelid is flipped.
Figure 11:
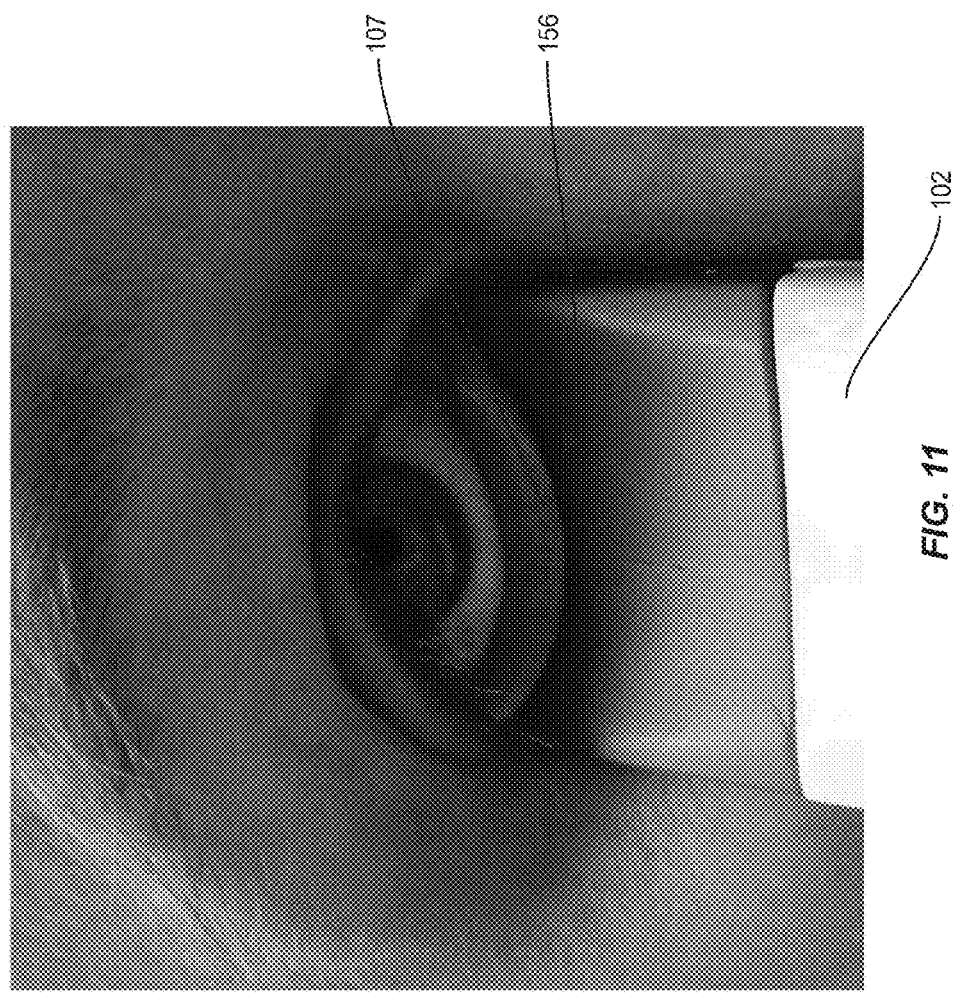
FIG. 11 illustrates the lid flipping device of FIG. 10 being positioned to flip a patient's eyelid downward such that the integrated IR light pipe contained therein can trans-illuminate the patient's eyelid.

Now that the MGI device 54 has been described, more exemplary detail of the lid flipping device 102 will now be described. In this regard, FIG. 10 is a schematic diagram of the exemplary lid flipping device 102 that can be used with the MGI device 54 in FIGS. 6A-6C to flip the patient's eyelid 82 downward (for a bottom eyelid) or upward (for an upper eyelid) to facilitate exposing the interior surface 107 of the eyelid 82 (shown in FIGS. 8 and 11) to the imaging path of the imaging device 84 to capture images. As shown in FIG. 10, the lid flipping device 102 includes a body 150 having a first end 152 and a second end 154. A curved lid flipping end surface 156 is disposed on the first end 152. The curved lid flipping end surface 156 is configured to grasp and flip an eyelid as shown in FIG. 8. The curved lid flipping end surface 156 is shaped to contain a radius that is intended to mimic the curvature of a patient's eyelid, so that ideally, the curved lid flipping end surface 156 will contact and grasp the exterior surface of the patient's eyelid equally along the curved exterior surface for even gripping and flipping.

The curved lid flipping end surface 156 itself may be planar or have a concave or convex radius for contacting the eyelid tissue. Alternatively, the curved lid flipping end surface 156 may also contain one or a series of ribs, ridges, protrusions, or indentations for providing a gripping surface on the eyelid tissue. In addition, the curved lid flipping end surface 156 may be constructed from a lower durometer, conforming or accommodative material to provide further traction or gripping surface on the eyelid tissue. In addition, the end surface material itself can be supplied in a tacky, high friction format to further enhance the grip on the eyelid tissue.

With continuing reference to FIG. 10, in this example, the lid flipping device 102 also contains the light source 104 disposed within the body 150. The light source 104 is an IR light source in this example. As will be described in more detail below, the light source 104 is controlled by the control system 100 in the MGI device 54 to generate a light along the path shown in FIG. 10 between the curved lid flipping end surface 156 and the eyelid 82. As will be shown in greater detail later in this disclosure, the body 150 of the lid flipping device 102 contains an elongated slot 158 disposed in the curved lid flipping end surface 156 to receive the light emitted from the light source 104 to form a light pipe. Thus, when the curved lid flipping end surface 156 contacts and grasps a patient's eyelid to flip the eyelid, as shown in eyelid 82 in FIG. 8, the elongated slot 158 is disposed adjacent to the exterior surface of the eyelid 82, as shown in FIG. 8 and in FIG. 10. In this manner, the light pipe illuminates an exterior surface 160 of the eyelid 82, as shown in FIG. 10, to trans-illuminate the eyelid. In this example, since the light source 104 is an IR light source, the light pipe is an IR light pipe that trans-illuminates the eyelid 82. The control system 100 of the MGI device 54 can then control the imaging device 84 to capture an image of the interior surface 107 of the patient's eyelid 82 to capture an IR trans-illumination image of the eyelid 82 and the meibomian glands disposed therein, like the IR trans-illumination image 48 in FIG. 5B, as an example. The control system 100 of the MGI device 54 can be connected directly to the imaging device 84 or wirelessly.

With continuing reference to FIG. 10, in this example of the lid flipping device 102, the light source 104 is comprised of a plurality of light sources, which may be IR light emitting diodes (LEDs) for example. In this example, there are three IR LEDs contained within the body 150 that are not shown. The IR LEDs individually emit IR light into three (3) zones 162(1)-162(3) to illuminate different areas of the exterior surface 160 of the eyelid 82 for uniform or substantially uniform illumination. As will also be discussed in more detail below, because of the curvature of the eyelid 82, and tissue thicknesses within an individual eyelid, the control system 100 may vary the intensity of the illumination between different IR LEDs differently so that a uniform intensity of light trans-illuminates the eyelid 82.

Now that the MGI device 54 and lid flipping device 102 have been described, more exemplary features of the MGI device 54 for illuminating, trans-illuminating, and capturing surface and trans-illumination images of a patient's eyelid are now discussed.

Figure 12:
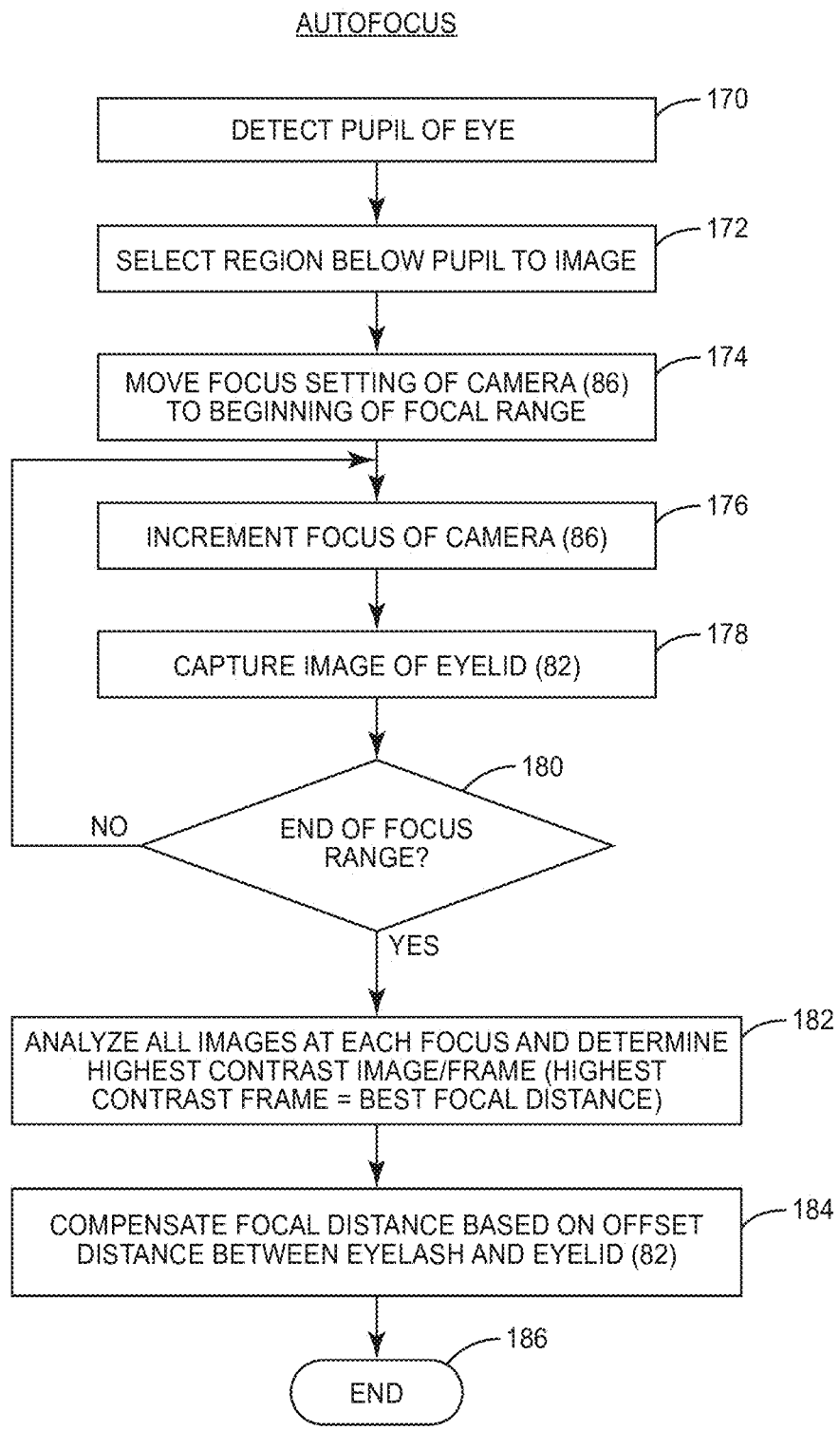
FIG. 12 is a flowchart illustrating an exemplary process for autofocusing the camera of the MGI device in FIG. 6A to a patient's eyelid before performing meibomian gland imaging.

Before the patient's eyelid 82 is flipped by a clinician and the MGI device 54 operated to illuminate and image the patient's eyelid, it may be desired to focus the imaging device 84 (e.g., video camera 86) of the MGI device 54. In this manner, the captured images of the eyelid 82 will be in focus. The imaging device 84 could be focused manually by a clinician, but the MGI device 54 may also be configured to autofocus the imaging device 84. In this regard, FIG. 12 illustrates a flowchart that provides an exemplary process for the MGI device 54 providing autofocusing of the video camera 86. In this regard, the control system 100 can instruct the video camera 86 to focus on the patient's eye or other structure of the eye to focus the video camera 86. In this regard, the control system 100 can be controlled to take a first image of the patient's eye to detect the pupil portion of the patient's eye in the image (block 170). For example, any technique to detect the pupil portion of the patient's eye in the image may be used. For example, the control system 100 may be configured to detect darker colored regions in the image to detect the location of the pupil. Next, the control system 100 analyzes the captured image to reposition the video camera 86 to be directed towards a region below the pupil of the patient's eye according to the position of the pupil in the first image captured (block 172). This is because in this example, the autofocusing method takes advantage of the discovery that the patient's eyelashes or the shadow of eyelashes on the eye present a high contrast object that can be imaged by the video camera 86 and detected by the control system 100 in a resulting image, which can be used to analyze the focus of the video camera 86 and to adjust the focus of the video camera 86, if needed. For example, a patient's eyelashes or the shadow of the eyelashes can appear in captured images of a patient's eye. Note that the eyelashes of the patient's eye therein appear in high contrast. The control system 100 may be configured to reposition the video camera 86 by a fixed distance below the pupil with the assumption that each of the patient's bottom eyelashes generally will be located within a given distance from their pupil.

Next, with continued reference to FIG. 12, the control system 100 adjusts the focus of the video camera 86 to the beginning of its focal range (block 174). The control system 100 then increments the focus of the video camera 86 to the next focal increment from the current focal setting (block 176). The control system 100 controls the video camera 86 to capture another image of the patient's eyelid 82 with the video camera 86 repositioned as discussed above (block 178). The image is stored by the control system 100 along with the focal setting for the video camera 86 when the image was captured. The control system 100 determines if the video camera 86 focus setting is at the end of its focal range (block 180). If not, the control system 100 repeats the steps in blocks 176 and 178 discussed above to capture additional images of the patient's eye with the video camera 86 remaining positioned below the pupil of the patient's eye, as discussed above, over the focal distance range of the video camera 86. Once the focal setting of the video camera 86 can be adjusted through its focal range, with images of the patient's eye at each focal setting captured and stored, the control system 100 can analyze the stored images to determine how to auto focus the video camera 86.

In this regard, with continued reference to FIG. 12, the control system 100 analyzes each of the stored images taken at different focal lengths of the video camera 86 to determine which image has the has the highest contrast ratio (block 182). The image with the highest contrast ratio is deemed to be the best focal distance between the video camera 86 and the patient's eye. The control system 100 may be programmed with image processing software, as discussed in more detail below, to determine the contrast ratio of an image to be used for comparison to other captured images captured under different focal distance settings for the video camera 86. The control system 100 can look up the focal setting that was used for the video camera 86 to capture the image having the highest contrast ratio to be used as the focal setting for the video camera 86 to be used for capturing subsequent images of the patient's ocular tear film for analysis. Optionally, the control system 100 can compensate for the focal distance setting of the video camera 86 that was used to capture the image having the highest contrast ratio for the final focal distance setting to use to auto focus the video camera 86. For example, the control system 100 may compensate the focal setting used to auto focus the video camera 198 based on knowing that there is a distance between eyelashes of the patient's eye and the eyelid 82 of the patient's eye (block 184) before the autofocus process is completed (block 186). For example, a distance between eyelashes of the patient's eye and the eyelid 82 of the patient's eye may be assumed to be a given known distance.

Figure 13:
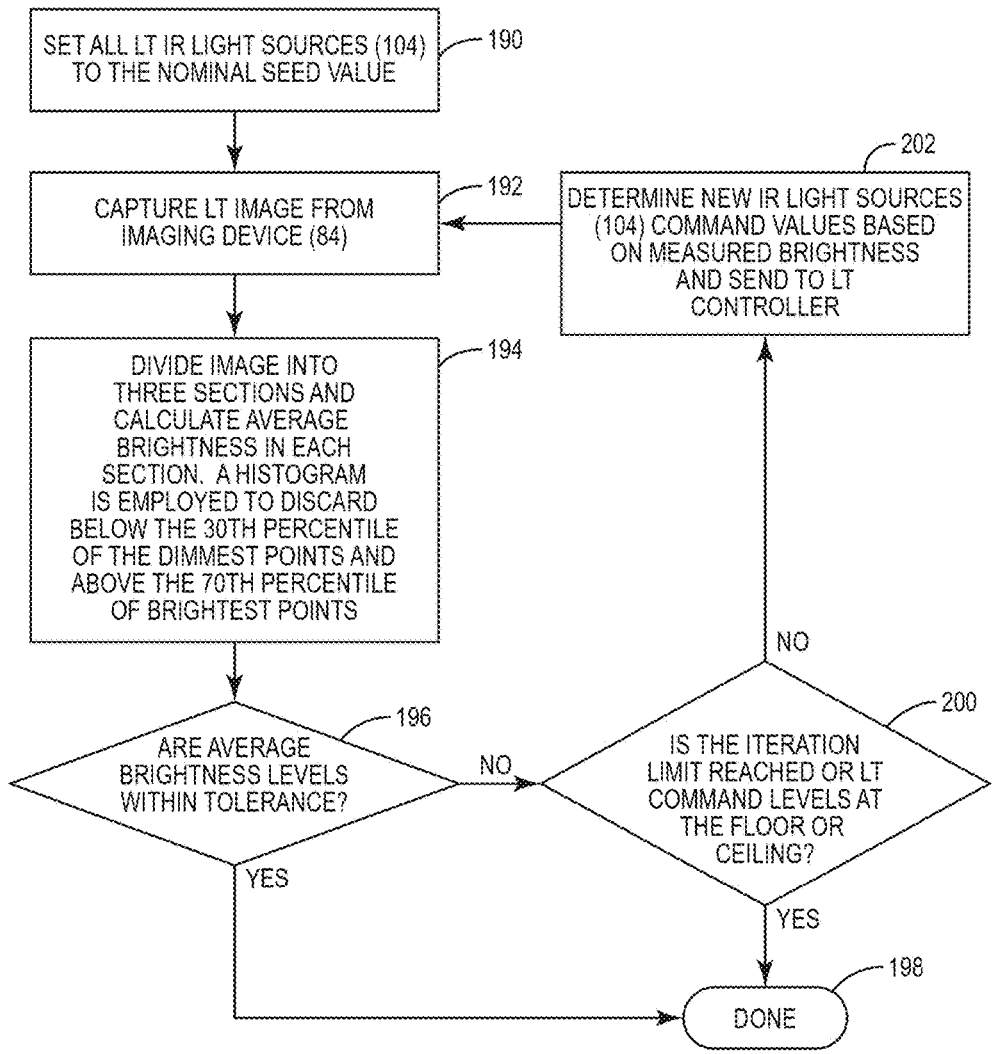
FIG. 13 is a flowchart illustrating an exemplary process for the MGI device in FIG. 6A performing lid trans-illumination imaging of a patient's eyelid.

If it is desired for the MGI device 54 to capture a trans-illumination image of the patient's eyelid, the control system 100 of the MGI device 54 can be controlled to perform a trans-illumination image capture routine. In this regard, FIG. 13 is a flowchart illustrating an exemplary process for the MGI device 54 in FIG. 6A performing lid trans-illumination imaging of a patient's eyelid. In this regard, the clinician sets the patient to be examined and uses the lid flipping device 102 to flip the eyelid to be imaged so as to expose the interior surface of the eyelid to the imaging path of the imaging device 84 in the MGI device 54. This has been previously described and illustrated above. With the patient's eyelid flipped using the lid flipping device 102, the clinician initiates the MGI device 54 to trans-illuminate and capture an IR trans-illumination image of the patient's eyelid, like the IR trans-illumination image 48 in FIG. 5B, as an example. In response, the control system 100 of the MGI device 54 sets all lid trans-illumination (LT) LEDs of the IR light source 104 in the handheld lid flipping device 102 to a nominal seed value to set the desired illumination intensity (block 190). The control system 100 then instructs the imaging device 84 to capture an IR trans-illumination image of the patient's eyelid (block 192). In this example, the process includes an auto-brightness adjustment procedure. In this regard, in this example, the captured IR trans-illumination image is divided by the control system's 100 processing systems into three (3) sections and the average brightness in the image is calculated in each section. An image histogram may be employed to record the intensities for the pixels in the image such that a certain portion of the least intensive (i.e., dimmest) pixels/points are excluded from a processed image, and likewise a portion of the most intensive (i.e., brightest) pixels/points are also excluded from a processed image (block 194). This image process may ensure that the IR trans-illumination image does not contain over saturated pixels in the image. The control system 100 then determines if the average brightness levels of the resulting processed IR trans-illumination image are within a desired tolerance (decision 196). If yes, the processing of the captured IR trans-illumination image is done (block 198), and the resulting processed IR trans-illumination image can be displayed or otherwise analyzed by a clinician.

With continuing reference to FIG. 13, if however, the average brightness in decision 196 was not within a desired tolerance, the control system 100 determines if an iteration limit has been reached for IR imaging the patient's eyelid based on different IR light source 104 intensities (decision 200). If so, the process completed (block 198) with the most recent IR trans-illumination image captured and processed will be the IR trans-illumination image of the patient's eyelid used for display and/or analysis. If the iteration limit has not been reached for IR imaging the patient's eyelid based on different IR light source 104 intensities (decision 200), the control system 100 determines new IR light source 104 intensities to command the IR light source 104 based on the measured average brightness (block 202). The control system 100 then sends commands to the IR light source 104 in the lid flipping device 102 to illuminate at the new set intensity level to capture another IR trans-illumination image of the patient's eyelid (block 192) in a repeat of the process of blocks 192-196.

Figure 14A:
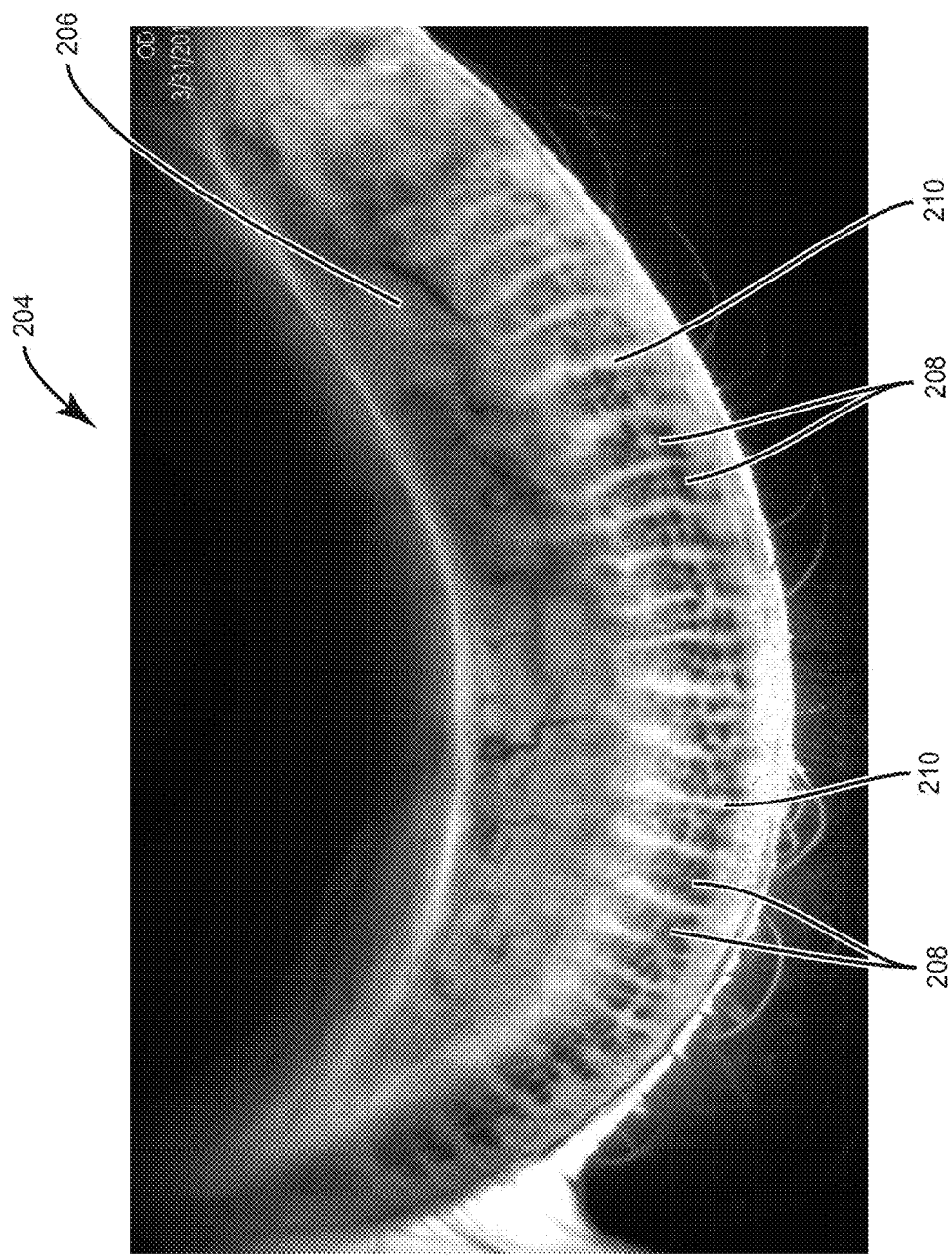
FIG. 14A is a lid trans-illumination image of a patient's eyelid captured by the MGI device in FIG. 6A while the patient's eyelid was flipped with the lid flipping device in FIG. 10 and IR trans-illuminated, wherein the meibomian glands are shown in the dark areas with non-gland material shown in the light areas.

FIG. 14A is an exemplary IR trans-illumination image 204 of a patient's eyelid 206 captured by the MGI device 54 in FIG. 6A using the process in FIG. 13, while the patient's eyelid 206 was flipped with the lid flipping device 102 in FIG. 10 and IR illuminated by the IR light source 104 therein. As shown in FIG. 14A, meibomian glands 208 in the patient's eyelid 206 are shown in the darker areas with non-gland material 210 shown in the lighter areas. The IR trans-illumination image 204 provides an enhanced contrast between the meibomian glands 208 and the non-gland material 210 in an X-ray like image, because as discussed, the IR light was directed by the IR light source 104 in the lid flipping device 102 to the exterior surface of the patient's eyelid 206. The IR light reflects from the meibomian glands 208 and passes through the non-gland material 210. Thus, the darker areas where the IR light does not pass shows the presence of meibomian glands 208 thus providing a trans-illuminated image of the meibomian glands 208 for display and/or analysis.

Figure 14B:
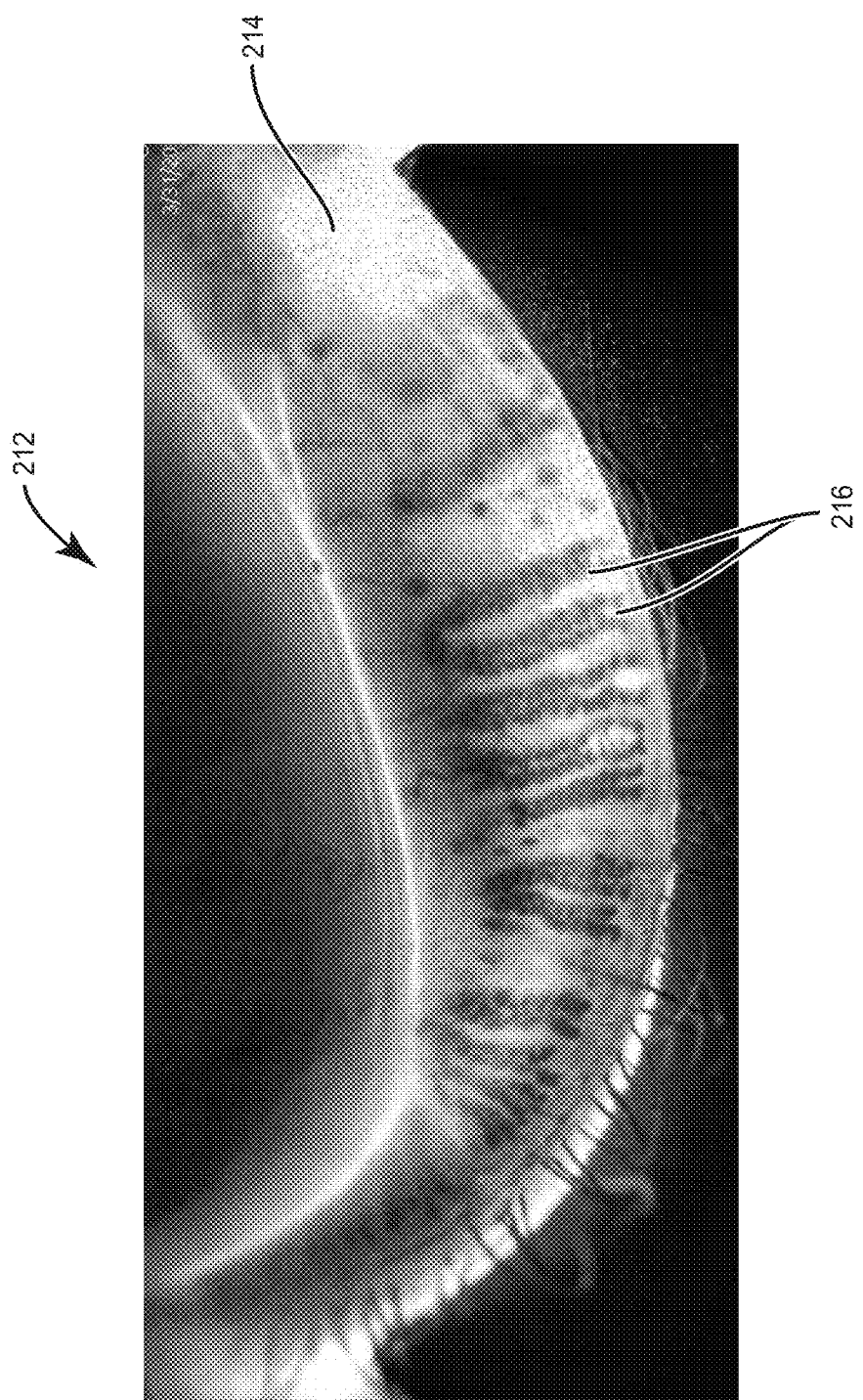
FIG. 14B is a lid trans-illumination image of another patient's eyelid captured by the MGI device in FIG. 6A while the patient's eyelid was flipped with the lid flipping device in FIG. 10 and IR trans-illuminated, illustrating where several meibomian glands are missing or damaged.

FIG. 14B is another IR trans-illumination image 212 of another patient's eyelid 214 captured by the MGI device 54 in FIG. 6A while the patient's eyelid 214 was flipped with the lid flipping device 102 in FIG. 10 and IR trans-illuminated by the IR light source 104 therein. In this patient's eyelid 214, while meibomian glands 216 are present, several areas of the eyelid 214 contain areas where meibomian glands are missing or damaged. The IR trans-illumination image 212 shows this in a high contrast image. Thus, for this patient, the ability to determine missing meibomian glands 216 may explain a lack or reduced amount of lipid production for the patient, whereas in the patient's eyelid 206 in FIG. 14A, all meibomian glands 208 are present. Thus, for the patient's eyelid 206 in FIG. 14A, if there is a lack of lipid production, such can be determined to not be a result of missing meibomian glands based on a viewing and analysis of the IR trans-illumination image 204.

As discussed above, it may also be desired to capture an IR surface meibography image of the patient's eyelid for analysis and for combining with an IR trans-illumination image of the patient's eyelid to provide a higher contrast image of the patient's meibomian glands. As discussed above, with IR surface illumination, the MGI device 54 is configured to command IR illuminators 64A, 64 present in the housing 56 (not the lid flipping device 102) to illuminate the patient's eyelid. This is because the interior surface of the patient's eyelid is being illuminated for IR surface meibography, as opposed to the exterior surface as provided for IR trans-illumination using the IR light sources 104 in the lid flipping device 102.

Figure 15A:
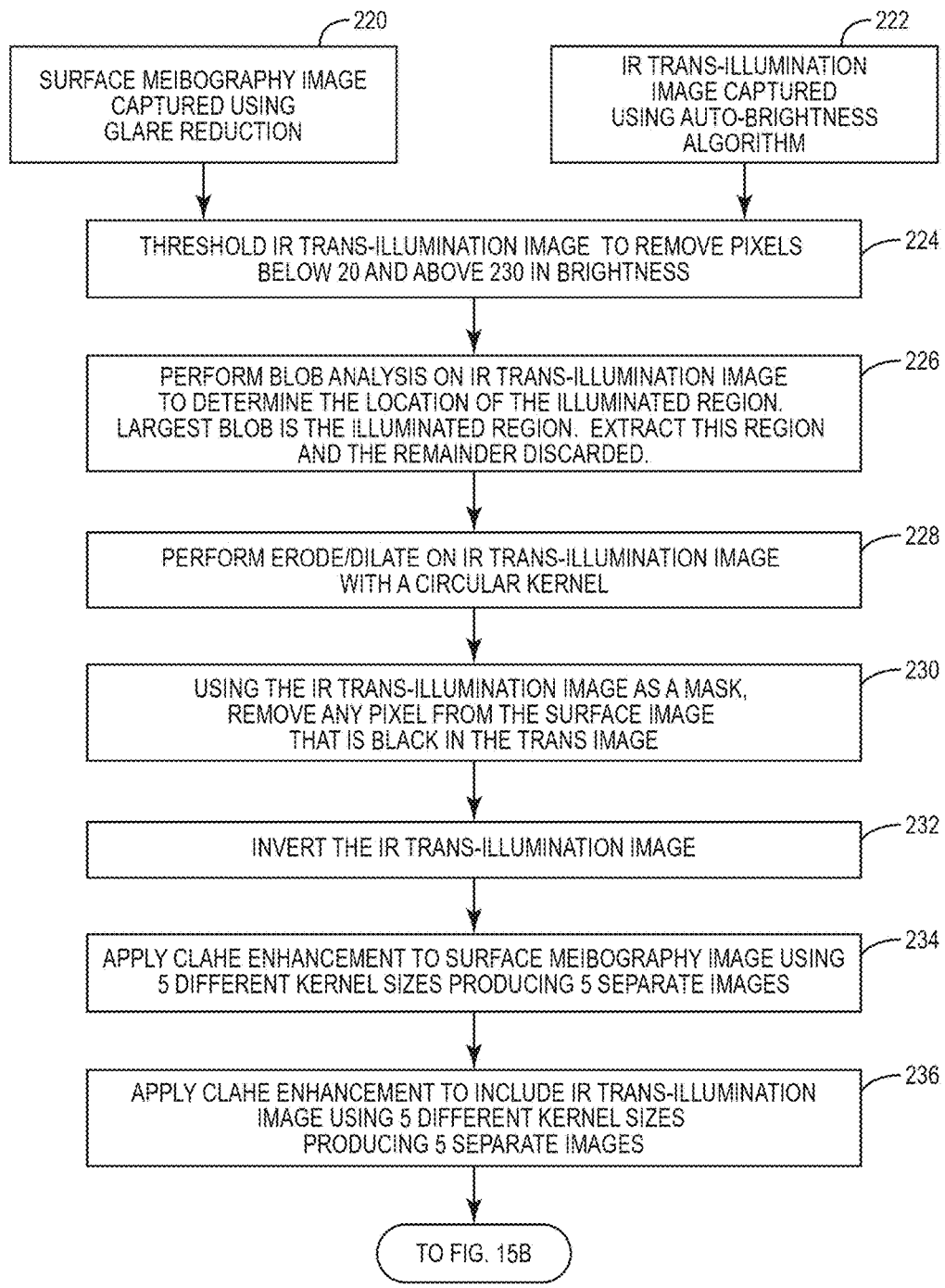
FIGS. 15A and 15B are flowcharts for an exemplary process of the MGI device in FIG. 6A generating a combined surface meibography/lid trans-illumination image of meibomian glands.
Figure 15B:
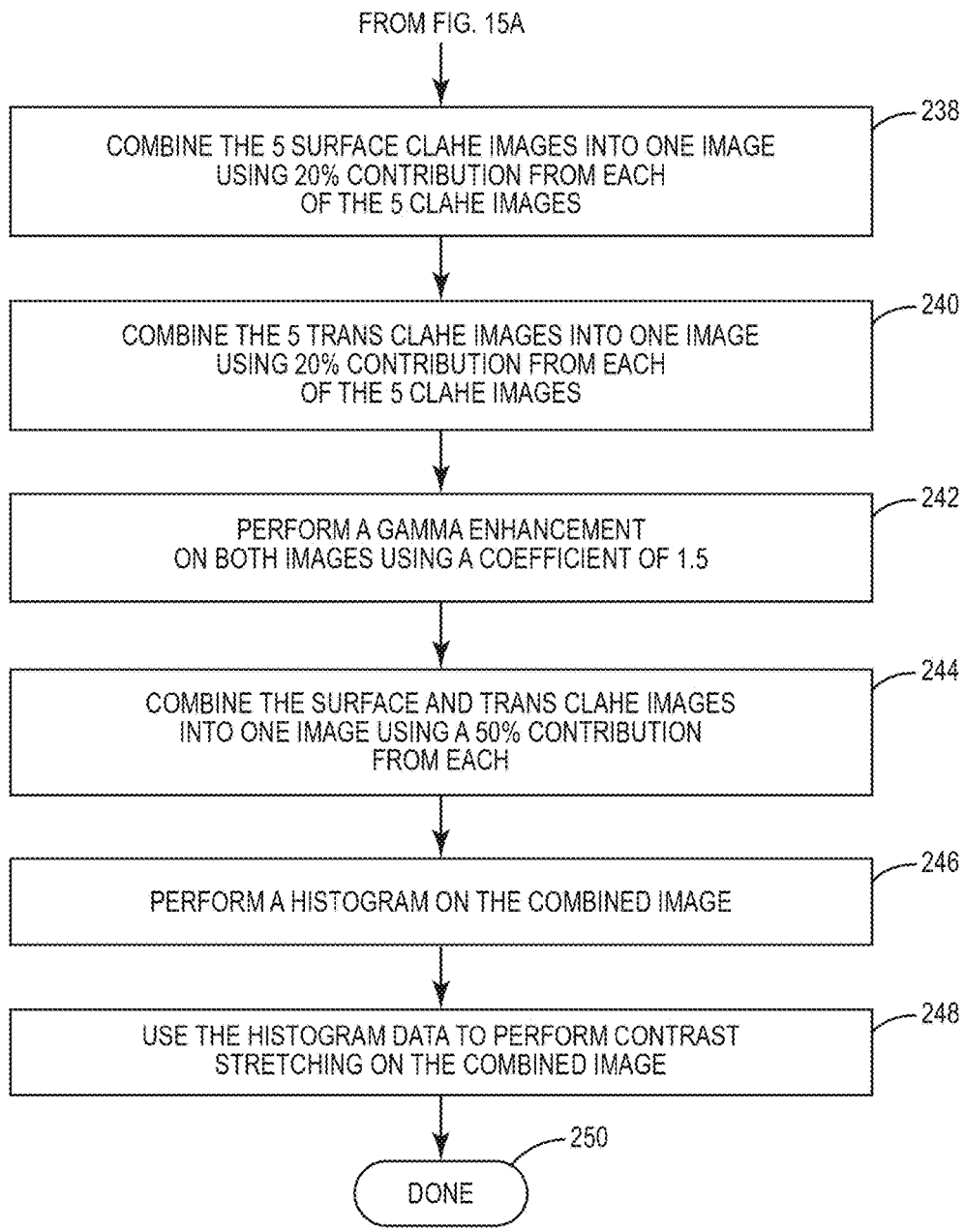

In this regard, FIGS. 15A and 15B are flowcharts for an exemplary process of the MGI device 54 in FIG. 6A generating a resulting combined surface meibography/lid trans-illumination image of meibomian glands. In this regard, with a captive patient being positioned in the MGI device 54, and the patient's eyelid to be imaged flipped with the lid flipping device 102, the patient's eyelid is imaged by the imaging device 84. As will be discussed in more detail below, the MGI device 54 may be configured to capture the surface meibography image of a patient's eyelid using a glare reduction technique to reduce or avoid glare in the surface meibography image from the IR illuminator 64A, 64B (block 220). Also, as described above, the MGI device 54 is also configured to capture an IR trans-illumination image of the patient's eyelid using the IR light sources 104 in the lid flipping device 102 to trans-illuminate the patient's eyelid (block 222). The auto-brightness adjustment described above with regard to FIG. 13 may be employed as an option.

With continuing reference to FIG. 15A, next the control system 100 processes IR trans-illumination image of the patient's eyelid to remove pixels below and above given intensity thresholds (block 224). The control system 100 can then perform a blob analysis on the IR trans-illumination image to determine the location of the illumination region (block 226). The illuminated region may be determined to be the region that has the largest blob present (block 226). The control system 100 can then extract this region of interest from the illumination region and discard the remainder of the image (block 226). Next, the control system 100 can perform optional erode and dilate functions on the IR trans-illumination image with a circular kernel (block 228). Next, using the remaining/resulting IR trans-illumination image as a mask, the control system 100 removes any pixels from the surface meibography image that is black in color in the IR trans-illumination image to enhance the surface meibography image (block 230). The IR trans-illumination image is next inverted by the control system 100 prior to combining or subtracting with the surface meibography image so that the images are compatible to be combined with the meibomian glands being both shown in light or white areas (block 232). Clahe enhancements can further be added to the surface meibography image (block 234) and the inverted IR trans-illumination image (block 236).

Figure 17A:
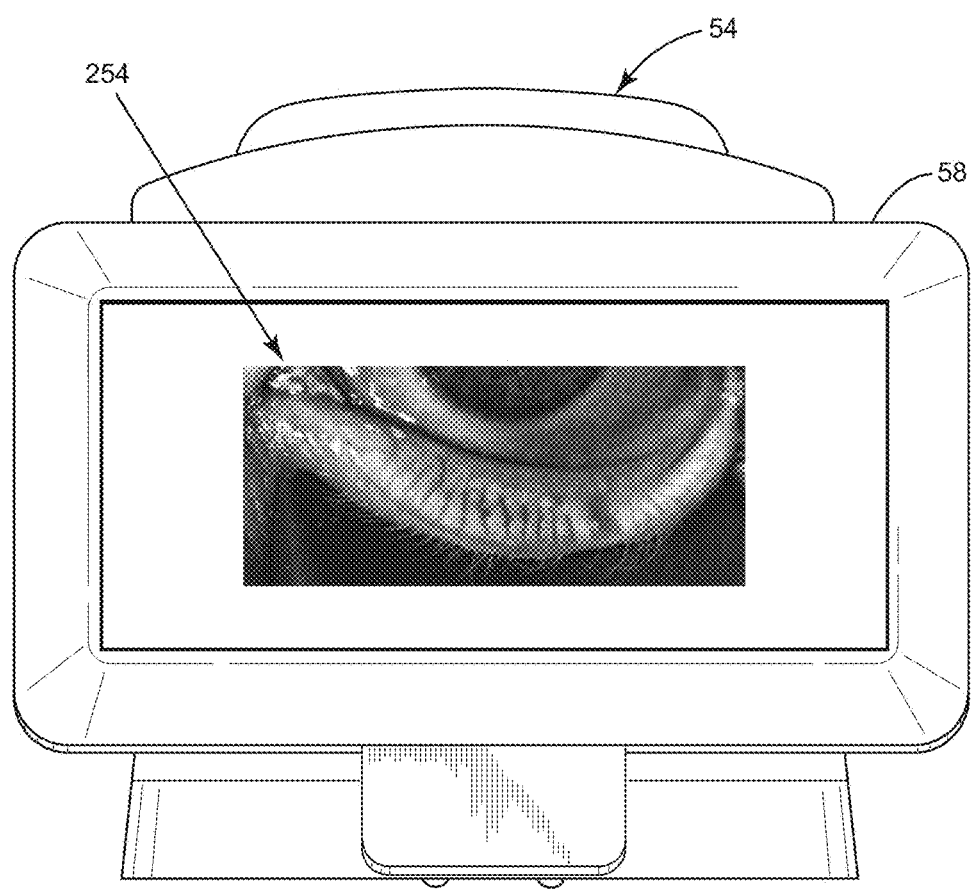
FIGS. 17A-17C illustrate a surface meibography image, a lid trans-illumination image, and a combined surface meibography/lid trans-illumination image on a display of the MGI device in FIG. 6A.
Figure 17B:
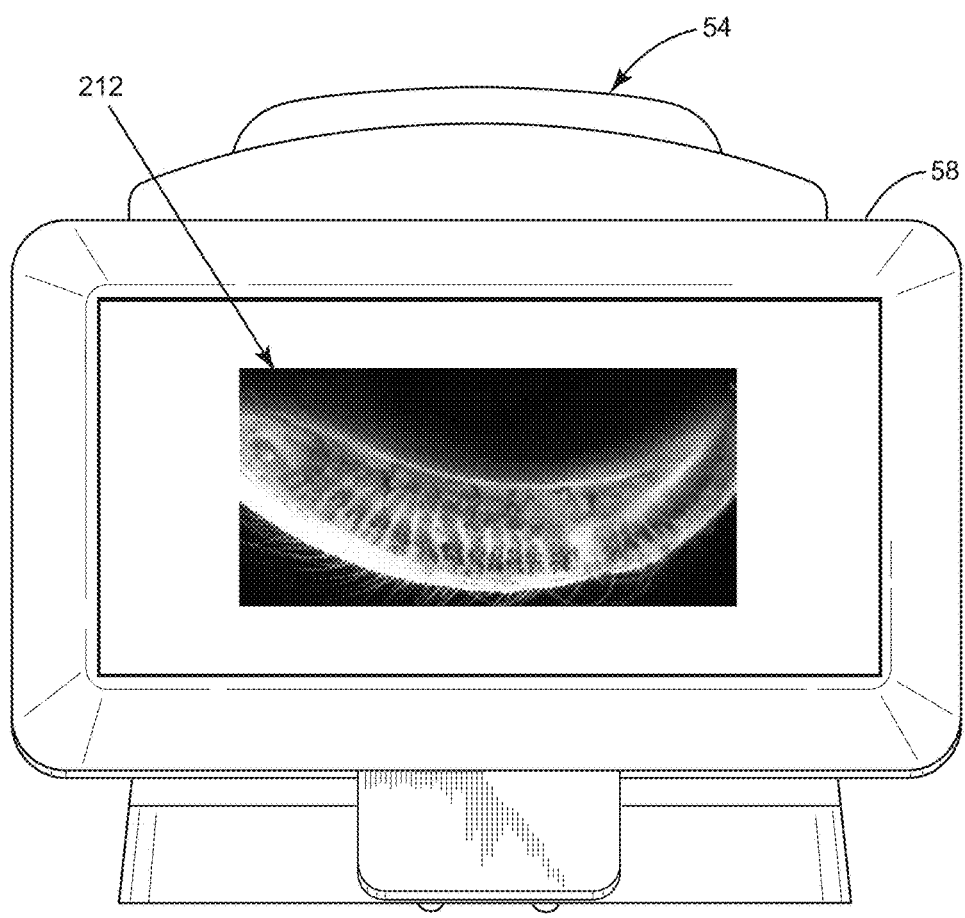

With reference to FIG. 17B, the control system 100 can then combine the Clahe enhanced images of the surface meibography image into the inverted IR trans-illumination image (block 238), and vice versa (block 240) to provide Clahe surface meibography and IR trans-illumination images. The control system 100 can then perform a gamma enhancement on the surface meibography and IR trans-illumination images (block 242). Next, the control system 100 can combine the surface meibography and IR trans-illumination images into a resulting combined surface meibography/IR trans-illumination image using a contribution from each of the separate surface meibography and IR trans-illumination images (e.g., 50%) (block 244). The control system 100 can then perform an image histogram on the combined surface meibography/IR trans-illumination image (block 246) to perform contrast stretching on the combined surface meibography/IR trans-illumination image (block 248), and the process ends (block 250).

Figure 17C:
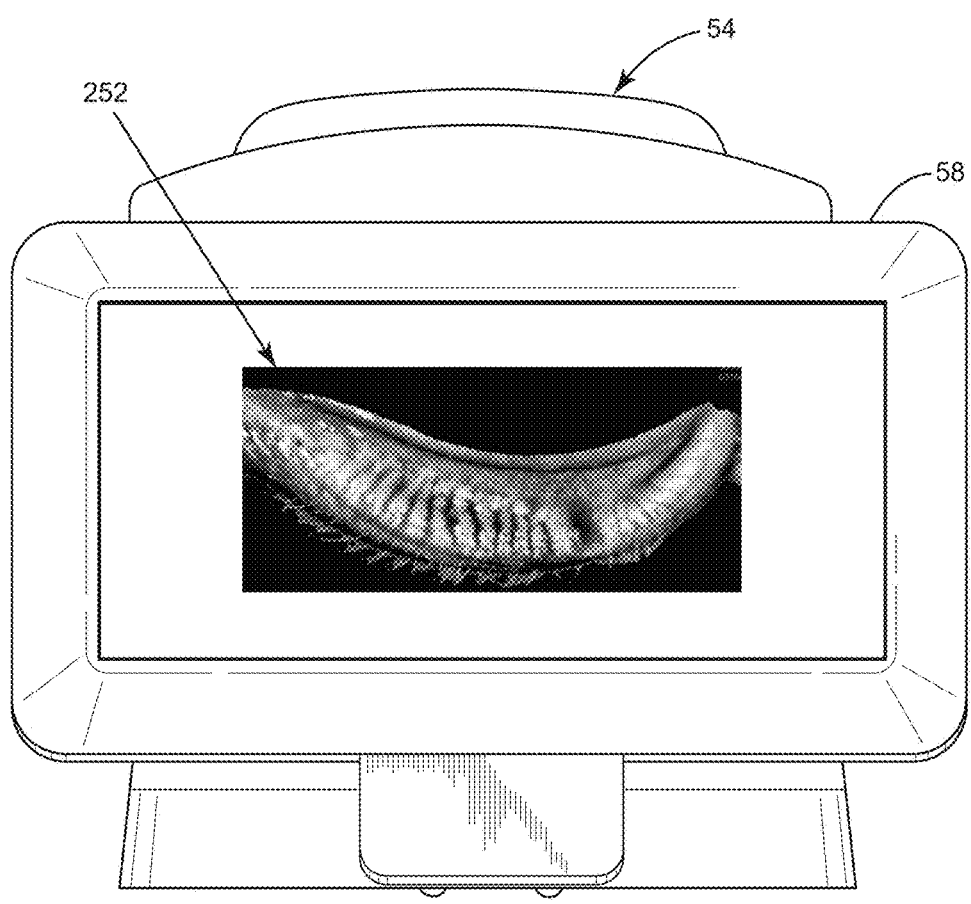

The resulting combined surface meibography/IR trans-illumination image can then be displayed or analyzed as an image containing a high contrast image of the meibomian glands in the patient's eyelid. This is illustrated in FIG. 16C. FIG. 16C is a combined surface meibography/IR trans-illumination image 252 resulting from the surface meibography image 254 of the patient's eyelid 214 in FIG. 16A and the previously discussed IR trans-illumination image 212 of the patient's eyelid 214 in FIG. 16B. Notice the higher contrast images of the meibomian glands 216 in the combined surface meibography/IR trans-illumination image 252 as compared to the corresponding images of the same meibomian glands 216 in the surface meibography image 254 in FIG. 16A. FIGS. 17A and 17B illustrate the surface meibography image 254 and the IR trans-illumination image 212, resulting from the surface meibography and the IR trans-illumination performed on a patient's eyelid by the MGI device 54 being displayed on the display 58, respectively, for analysis by a clinician. FIG. 17C illustrates the combined surface meibography/IR trans-illumination image 252 generated by the control system 100 using the exemplary IR illumination, IR imaging, and image processing processes described above displayed on the display 58 of the MGI device 54 for analysis by a clinician.

As discussed above with regard to block 220 in FIG. 15A, it may be desired to reduce glare in a surface meibography image captured by the MGI device 54. Because the IR illuminators 64A, 64B in the MGI device 54 are configured to illuminate the interior surface of a patient's eyelid, as well as the surface imaged, the reflection of the IR light emitted from the IR illuminators 64A, 64B is received and captured by the imaging device 84. This is not an issue for the IR trans-illumination image described above, because the IR light source 104 in the lid flipping device 102 trans-illuminates the eyelid from the exterior surface of the eyelid, whereas the imaging device captures the IR trans-illumination image from the interior surface of the eyelid. Thus, reflections of the IR light emitted by the IR light sources 104 in the lid flipping device 102 are not captured in the IR trans-illumination image by the imaging device 84.

Figure 18:
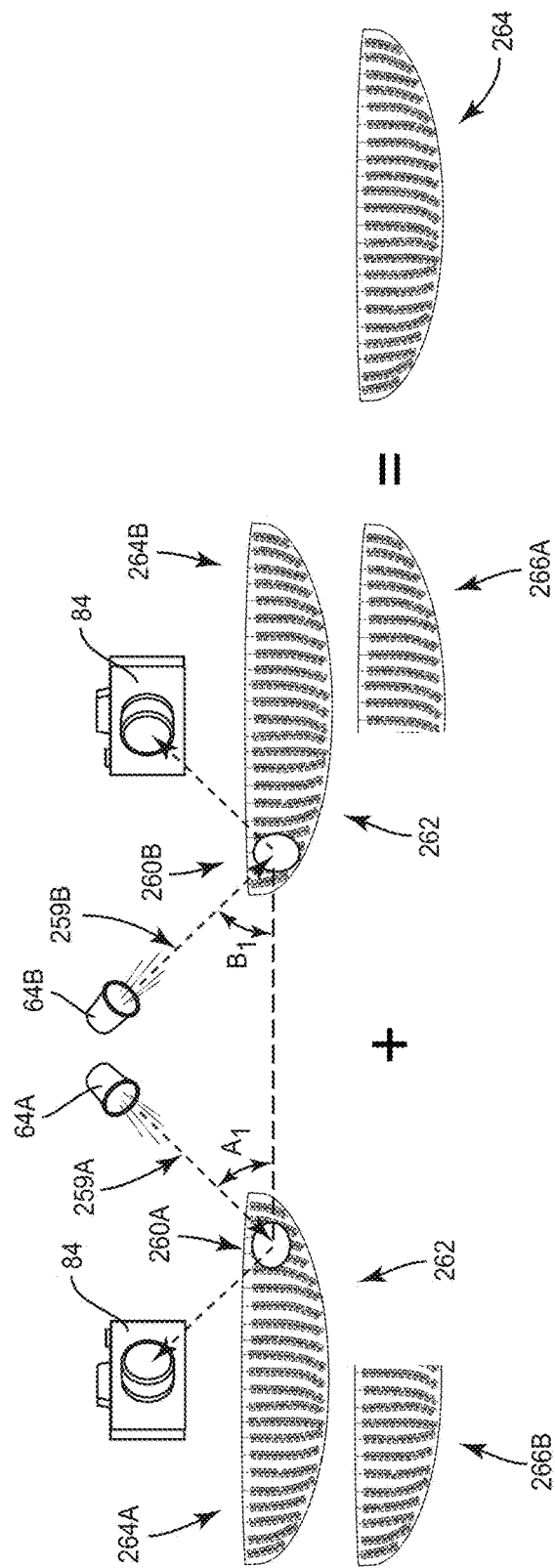
FIG. 18 is a schematic diagram of the MGI device in FIG. 6A capturing two different images of the surface of a patient's flipped-down eyelid with the eyelid being illuminated from two different directions, each containing glare from the captured reflection of the IR light, which can be spliced together by the MGI device to form one surface meibography image with reduced glare.

In this regard, FIG. 18 is a schematic diagram of an anti-glare or glare reduction technique that may be employed in the MGI device 54 during surface meibography to reduce or avoid glare from the IR light reflected from the IR illuminators 64A, 64B and captured by the imaging device 84. In this regard, the MGI device 54 is configured such that the control system 100 first directs a first IR illuminator 64A to emit a first IR light 259A from at a first angle A1 to a first angle end 260A of an interior portion of the eyelid 262 while directing the second IR illuminator 64B to not direct a second IR light 259B at a second angle B1, opposite the first angle A1, to the interior portion of the eyelid 262. A first surface meibography image 264A of the eyelid 262 is then captured by the imaging device 84. Then, the control system 100 directs the second IR illuminator 64B to emit the second IR light 259B at the second angle B1, opposite the first angle A1, to a second angle end 260B of the interior portion of the eyelid 262 directing the first IR illuminator 64A to not direct the first IR light 259A at the first angle A1 to the interior portion of the eyelid 262. A second surface meibography image 264B of the eyelid 262 is then captured by the imaging device 84. The control system 100 then combines a second angle end 266B of the first surface meibography image 264A with the first angle end 266A of the second surface meibography image 264B to produce a resulting surface meibography image 264 having reduced glare. The reduction in glare comes from the fact that the second angle end 266B of the first surface meibography image 264A only includes the half of the first surface meibography image 264A that does not include the glare from the reflected first IR light 259A from the first IR illuminator 64A, and the first angle end 266A of the second surface meibography image 264A only includes the half of the second surface meibography image 264B that does not include the glare from the reflected second IR light 259B.

Figure 19:
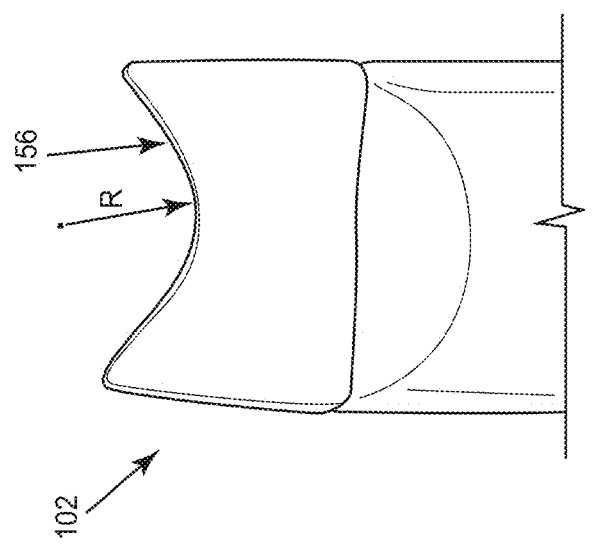
FIG. 19 is a diagram of an exemplary lid flipping device illustrating the curvature of a lid flipping end for grasping a curved eyelid for lid flipping in which the IR light pipe is disposed.

Now that the exemplary IR trans-illumination imaging and IR surface meibography imaging have been described, FIGS. 19-22 are now described to provide additional exemplary information on the lid flipping device 102 described above. In this regard, FIG. 19 is a diagram of the lid flipping device 102 illustrating the curvature of a lid flipping end surface 156 for grasping a curved eyelid for lid flipping. As shown there, the radius R of the lid flipping end surface 156 is shaped to attempt to mimic the average curvature of the eyelid as the eyelid curves out from a patient's eye. The goal is for every point on the lid flipping end surface 156 to contact the exterior surface of an eyelid simultaneously when the lip flipping end surface 156 contacts the exterior surface of the eyelid. In this manner, the lid flipping end surface 156 can grasp the eyelid to flip the eyelid equally or substantially equally along the exterior surface of the eyelid.

Alternatively, the curved lid flipping end surface 156 itself may be planar or have a concave or convex radius for contacting the eyelid tissue. Alternatively, the curved lid flipping end surface 156 may also contain one or a series of ribs, ridges, protrusions, or indentations for providing a gripping surface on the eyelid tissue surface. In addition, the curved lid flipping end surface 156 may be constructed from a lower durometer, conforming or accommodative material to provide further traction or gripping surface on the eyelid tissue. In addition, the end surface material itself can be supplied in a tacky, high friction format to further enhance the grip on the eyelid tissue.

Figure 20:
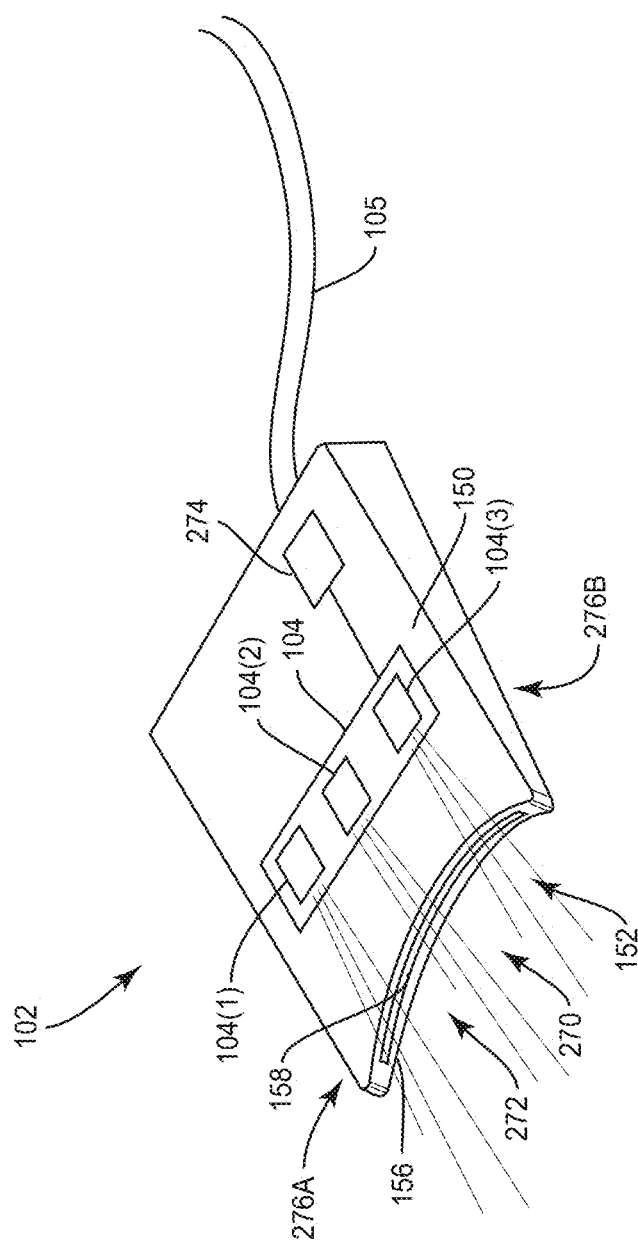
FIG. 20 is a schematic diagram of another exemplary embodiment of a lid flipping device that shows the IR light pipe disposed on the lid flipping end of the lid flipping device.

FIG. 20 illustrates a side perspective view of the lid flipping device 102 in FIG. 19 to show the light pipe. As previously discussed a light source is disposed inside the body 150 of the lid flipping device 102. The elongated slot 158 is shown disposed in the first end 152 of the body 150. The light source 104 disposed in the body 150 is configured to direct emitted light 270 towards the elongated slot 158 to form a light pipe 272. In this manner, when the curved lid flipping end surface 156 is disposed against the exterior surface of an eyelid to flip the eyelid, the light pipe 272 trans-illuminates the eyelid as discussed above. The light source 104 disposed in the body 150 of the lid flipping device 102 may be an IR light source or a visible spectrum light source, as examples. The light source 104 may be comprised of one or more LEDs as previously discussed above, wherein each LED is individually controllable by the control system 100 of the MGI device 54. A control circuit 274 may be provided in the lid flipping device 102 to interface with the control system 100 through the interface cable 105. The control circuit 274 is configured to control the activation and deactivation of the light source 104 and to control the intensity of individual LEDs or other light sources that comprise the light source 104. For example, the light source 104 may be comprised of a central emitter 104(2) having an optical path along a central portion of the elongated slot 158, a first end emitter 104(1) disposed adjacent to a first end 276A of the elongated slot 158; and a second end emitter 104(3) disposed adjacent to a second end 276B of the elongated slot 158. The control circuit 274 is configured to control each of the emitters 104(1)-104(3) individually to control the illumination intensity of each, as previously described. The control circuit 274 may also include a communications interface that is configured to receive control signals for controlling the IR light source 104 either through the interface cable 105 or through wireless communications.

Figure 21:
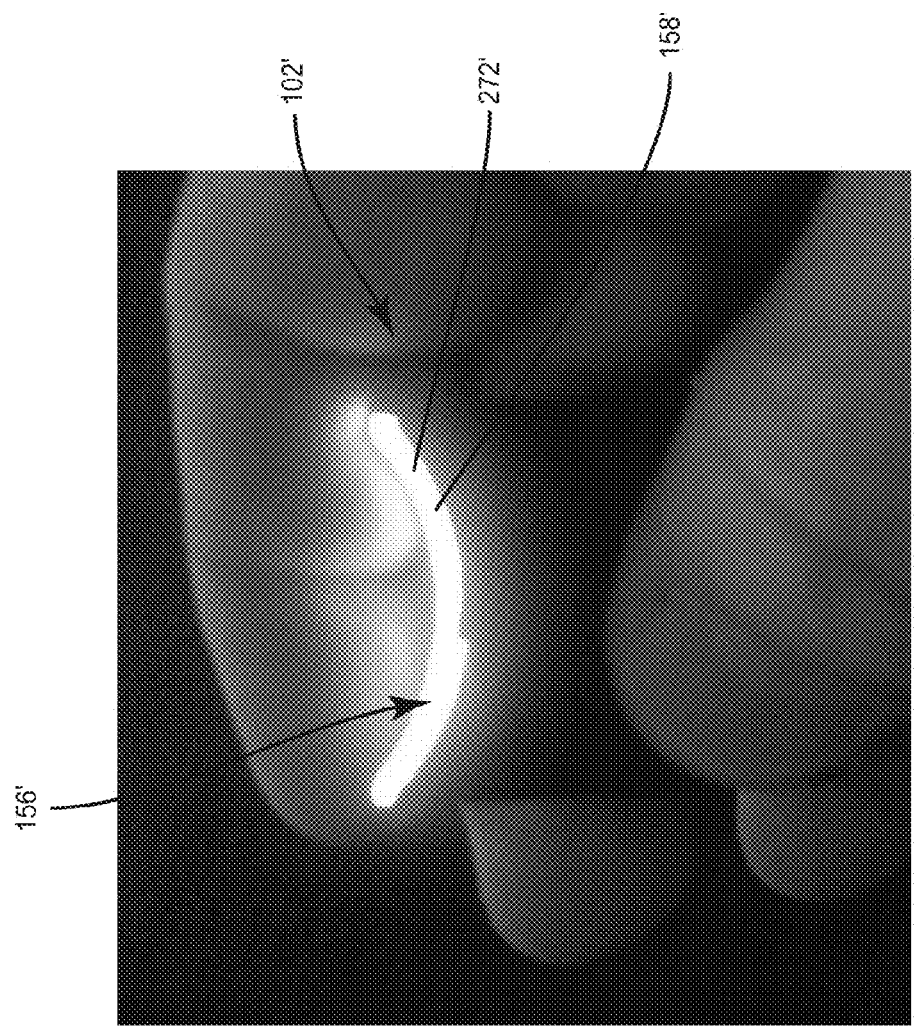
FIG. 21 is a schematic diagram of a lid flipping device that includes a visible light spectrum light pipe disposed on a lid flipping end of the lid flipping device for visible light lid trans-illuminating a patient's eyelid.
Figure 22:
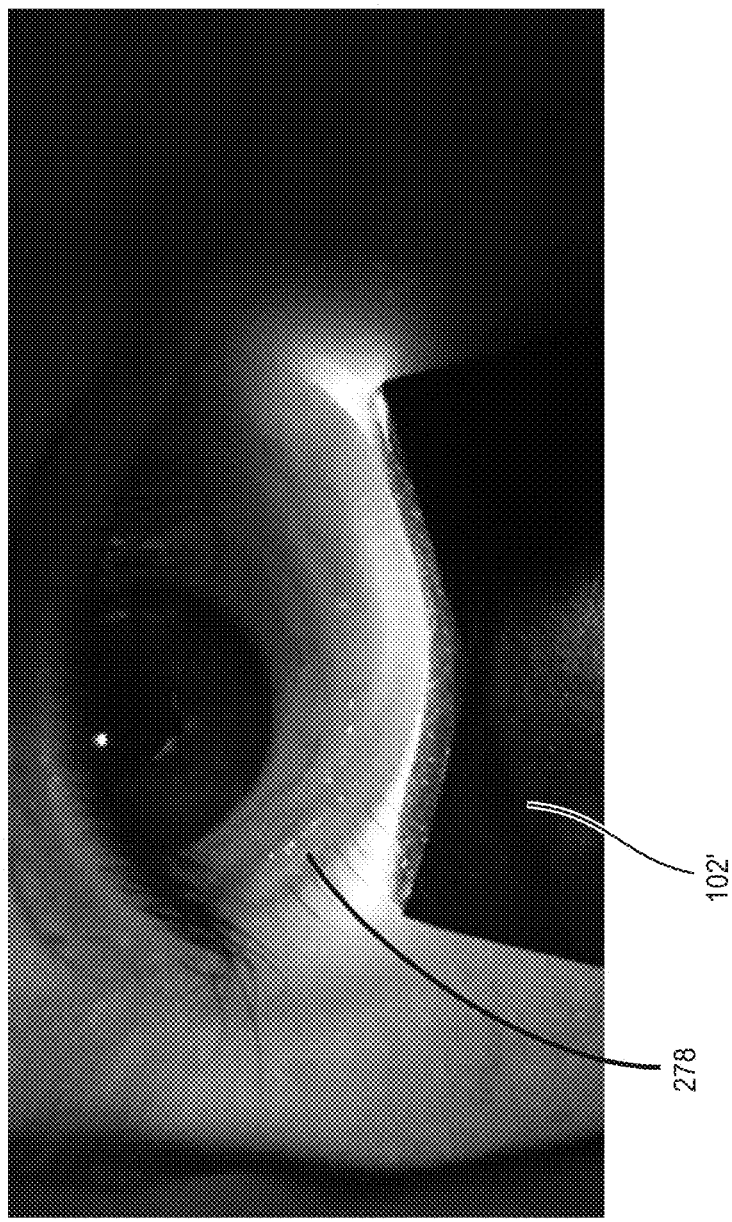
FIG. 22 is a diagram of the lid flipping device in FIG. 21 visible light spectrum lid trans-illuminating a patient's eyelid.

As discussed above, the light source 104 in the lid flipping device 102 may be an IR light source or a visible spectrum light source. It may be desired to use a visible spectrum light source to trans-illuminate the patient's eyelid. In this regard, FIG. 21 is a schematic diagram of an alternative lid flipping device 102' that includes a visible light spectrum light pipe 272' disposed on a first end 152' and illuminating through an elongated slot 158' of the lid flipping device 102'. The visible light spectrum light pipe 272' is configured to visible light lid trans-illuminate a patient's eyelid when the curved lid flipping end surface 156' of lid flipping device 102' is engaged with a patient's eyelid to flip the eyelid. FIG. 22 is a diagram of the lid flipping device 102' in FIG. 22 visible light trans-illuminating a patient's eyelid that is flipped down with the lid flipping device 102'. The MGI device 54 in FIG. 6A may be configured to capture a visible spectrum trans-illumination image of the patient's eyelid 278 when employing the lid flipping device 102' in FIGS. 21 and 22.

The embodiments discussed above that involve trans-illumination of a patient's eyelid involve directing a light source from the exterior surface of the eyelid towards the interior surface of the eyelid. The interior surface of the patient's eyelid is imaged to obtain a lid trans-illumination image of the meibomian glands in the patient's eyelid. Thus, to expose the interior surface of the patient's eyelid for imaging, yet be able to direct a light source to the exterior surface of the patient's eyelid, the eyelid is flipped downward with a lid flipping device that contains a light source. However, it may be desired to find an alternative method of trans-illuminating a patient's eyelid that does not require lid flipping or otherwise inverting or kinking the eyelid.

Figure 23:
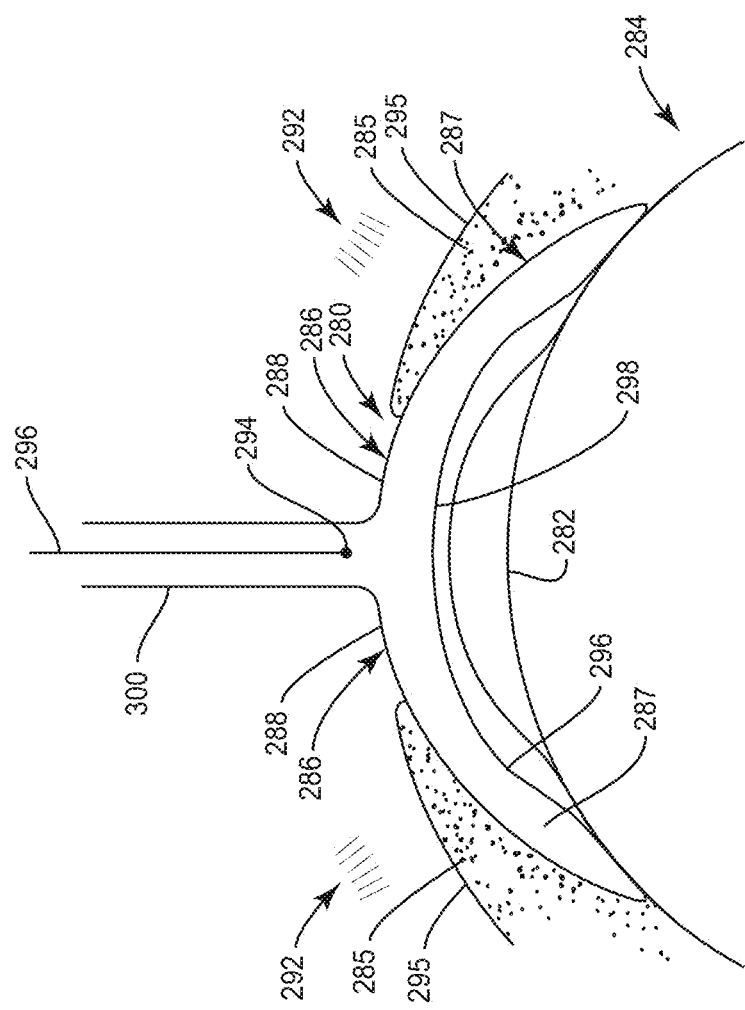
FIG. 23 is a schematic diagram of a mirrored scleral lens disposed on the cornea of a patient's eye, wherein the mirrored scleral lens is configured to illuminate the interior surface of the patient's eyelid without lid flipping to lid trans-illuminate the patient's eyelid.
Figure 24:
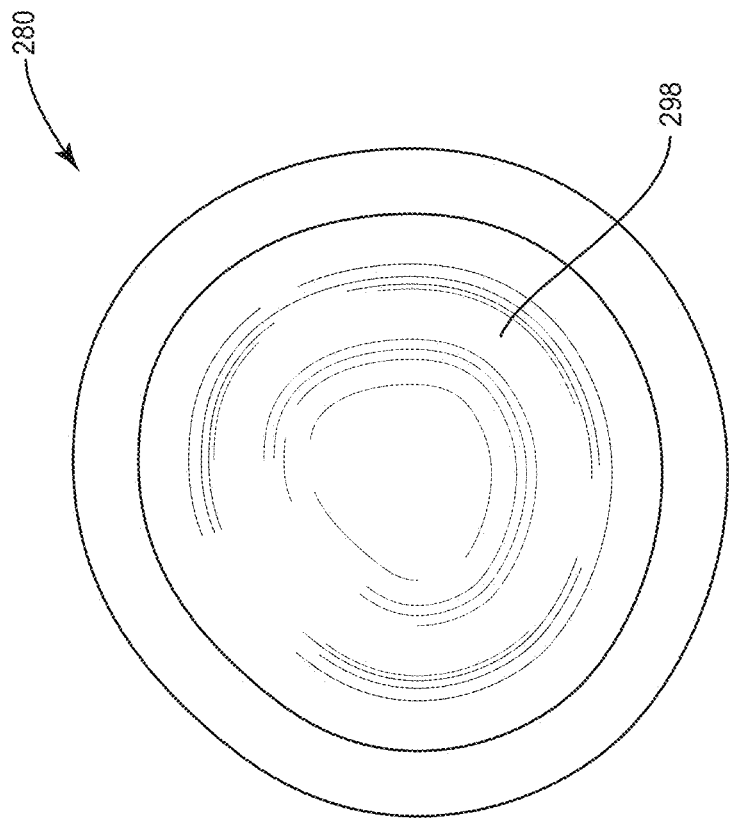
FIG. 24 is a schematic diagram of the interior surface of the mirrored scleral lens in the mirrored scleral lens in FIG. 23.

In this regard, FIG. 23 is a schematic diagram of a mirrored scleral lens 280 disposed or fitted on the cornea 282 of a patient's eye 284. The mirrored scleral lens 280 fits on the cornea 282 like a contact lens. The mirrored scleral lens 280 is configured to illuminate an interior surface 287 of the patient's eyelid 285 without lid flipping to lid trans-illuminate the patient's eyelid 285. In this regard, the outermost or exterior surface 286 of the mirrored scleral lens 280 has a mirrored surface 288 (one mirror or a series of minors) disposed on an eyecup 298 (see also, FIG. 24) to view or illuminate the interior portion of a patient's eyelid 285. In this manner, the patient's eyelid 285 can be trans-illuminated without eyelid flipping or kinking, because the patient's eyelid 285 in its natural state is disposed over the exterior surface 286 of the mirrored scleral lens 280.

With continuing reference to FIG. 23, to trans-illuminate the patient's eyelid 285 from the interior surface 287, light 292 from an external light source is directed to an exterior surface 295 of the patient's eyelid 285. For example, the light source may be from the MGI device 54 in FIG. 6A. The light 292 passes through the patient's eyelid 285 and is reflected from the mirrored surface 288 towards a camera 294 disposed in the eyecup 298 to capture a trans-illuminated image of the patient's eyelid 285. In this regard, the camera 294 is disposed in a platform 300 that extends from the eyecup 298 when the eyecup 298 is disposed on the patient's cornea 282. The camera 294 is communicatively coupled via a cable 296 disposed in the platform 300 to a system, such as control system 100 in the MGI device 54, to receive and process the trans-illumination images of the patient's eyelid 285 and the meibomian glands contained therein. FIGS. 25A-25C illustrate the mirrored scleral lens 280 from different views. As illustrated therein, the eyecup 298 is disposed on the end of the platform 300. The mirrored surface 288 is disposed on the eyecup 298. An electrical interface 302 is disposed on an end 304 of the platform 300 to allow power signals and an image signal to be communicated between the cameras 294A, 294B (FIG. 23) and a control system, such as control system 100 in the MGI device 54 in FIG. 6A.

We claim:

1. A method of trans-illuminating a meibomian gland in an eyelid of a patient to image the meibomian gland, comprising:
    flipping the eyelid to expose an interior portion of an interior surface of the eyelid to an imaging path of an imaging device, wherein the flipping of the eyelid is done using a lid flipping device comprising a body and a curved lid flipping end surface disposed on an end of the body, wherein the curved lid flipping end surface is anatomically shaped to contain a radius that is intended to mimic a curvature of the patient's eyelid, so that the curved lid flipping end surface will contact and grasp an exterior surface of the patient's eyelid equally along the exterior surface;
    directing an infrared (IR) light from an IR light source to an exterior portion of the eyelid to IR trans-illuminate meibomian glands in the eyelid;
    imaging the eyelid with the imaging device during IR trans-illumination to produce an IR trans-illumination image of meibomian glands in the eyelid, wherein the imaging of the eyelid with the imaging device during IR trans-illumination is performed while the eyelid is flipped;
    receiving the IR trans-illumination image of the eyelid at a computer control system associated with the imaging device;
    storing the IR trans-illumination image in a non-transitory memory associated with the imaging device;
    directing a second IR light from a second IR light source to the interior portion of the interior surface of the eyelid to surface illuminate the interior portion of the interior surface of the eyelid;
    imaging the interior portion of the interior surface of the eyelid with the imaging device when the interior portion is illuminated with the second IR light to produce a surface meibography image of meibomian glands in the eyelid, wherein the imaging of the interior portion of the interior surface of the eyelid to produce the surface meibography image is performed while the eyelid is flipped; and
        subtracting the IR trans-illumination image of meibomian glands from the surface meibography image of meibomian glands to generate a resultant image of meibomian glands.

2. The method of claim 1, wherein directing the IR light from the IR light source to the exterior portion of the eyelid comprises directing the IR light from the IR light source to the exterior portion of the exterior surface of the eyelid to IR trans-illuminate the meibomian glands in the eyelid.

3. The method of claim 2, wherein imaging the eyelid with the imaging device during IR trans-illumination comprises imaging the interior portion of the interior surface of the eyelid with the imaging device during IR trans-illumination to produce the IR trans-illumination image of meibomian glands in the eyelid.

4. The method of claim 1, wherein directing the IR light from the IR light source to the eyelid further comprises directing the IR light from the IR light source to the interior portion of the interior surface of the eyelid to IR trans-illuminate the meibomian glands in the eyelid.

5. The method of claim 4, wherein imaging the eyelid with the imaging device during IR trans-illumination comprises imaging an exterior portion of the exterior surface of the eyelid with the imaging device during IR trans-illumination to produce the IR trans-illumination image of meibomian glands in the eyelid.

6. The method of claim 1, wherein:
    directing the IR light from the IR light source to the exterior portion of the eyelid to IR trans-illuminate the meibomian glands in the eyelid further comprises directing the IR light from the IR light source to a lower eyelid; and
    imaging the eyelid with the imaging device during IR trans-illumination further comprises imaging the lower eyelid with the imaging device during IR trans-illumination to produce the IR trans-illumination image of meibomian glands in the lower eyelid.

7. The method of claim 1, wherein:
    directing the IR light from the IR light source to the exterior portion of the eyelid to IR trans-illuminate the meibomian glands in the eyelid further comprises directing the IR light from the IR light source to an upper eyelid; and
    imaging the eyelid with the imaging device during IR trans-illumination further comprises imaging the upper eyelid with the imaging device during IR trans-illumination to produce the IR trans-illumination image of meibomian glands in the upper eyelid.

8. The method of claim 1, wherein directing the IR light from the IR light source to the exterior portion of the eyelid to IR trans-illuminate the meibomian glands in the eyelid further comprises directing the IR light from the IR light source in an IR spectrum between 890 and 940 nanometers (nm) to the eyelid.

9. The method of claim 1, further comprising displaying the IR trans-illumination image of meibomian glands in the eyelid on a computer display.

10. The method of claim 1, wherein the IR light source and the second IR light source are different IR light sources.

11. The method of claim 1, further comprising not directing the IR light from the IR light source to the exterior portion of the eyelid when directing the second IR light from the second IR light source to the interior portion of the interior surface of the eyelid.

12. The method of claim 1, further comprising not directing the second IR light from the second IR light source to the interior portion of the interior surface of the eyelid when directing the IR light from the IR light source to the exterior portion of the eyelid.

13. The method of claim 1, further comprising displaying the surface meibography image of meibomian glands in the eyelid on a computer display.

14. The method of claim 1, wherein directing the second IR light from the second IR light source further comprises:
    directing the second IR light from a first angle to a first angle end of the interior portion of the eyelid while not directing the second IR light from a second angle, opposite the first angle, to the interior portion of the eyelid; and
    directing the second IR light from the second angle, opposite the first angle, to a second angle end of the interior portion of the eyelid while not directing the second IR light from the first angle to the interior portion of the eyelid;
    wherein imaging the interior portion of the interior surface of the eyelid with the imaging device further comprises:
    imaging the interior portion of the interior surface of the eyelid with the imaging device when the interior portion is illuminated with the second IR light at the first angle to produce a first surface meibography image of meibomian glands in the eyelid; and imaging the interior portion of the interior surface of the eyelid with the imaging device when the interior portion is illuminated with the second IR light at the second angle to produce a second surface meibography image of meibomian glands in the eyelid; and wherein the method further comprises combining the second angle end of the first surface meibography image of meibomian glands with the first angle end of the second surface meibography image of meibomian glands to produce the surface meibography image of meibomian glands having reduced glare resulting from imaged reflections of the second IR light from the interior portion of the interior surface of the eyelid.

15. The method of claim 14, wherein the second angle end of the first surface meibography image of meibomian glands only includes a portion of the first surface meibography image of meibomian glands that does not include glare from reflected IR light from a first IR light source, and the first angle end of the second surface meibography image of meibomian glands only includes a portion of the second surface meibography image of meibomian glands that does not include glare from the reflected second IR light.

16. A meibomian gland imaging system for lid trans-illumination imaging of meibomian glands in an eyelid of a patient, comprising:
an infrared (IR) light source configured to direct an IR light to an exterior portion of the eyelid to IR trans-illuminate the meibomian glands in the eyelid;
a second IR light source configured to direct a second IR light to an interior portion of an interior surface of the eyelid;
an imaging device configured to image the eyelid during IR trans-illumination;
a lid flipping device comprising a body and a curved lid flipping end surface disposed on an end of the body, the curved lid flipping end surface configured to grasp and flip the eyelid to expose the interior portion of the interior surface of the eyelid to an imaging path of the imaging device, wherein the curved lid flipping end surface is anatomically shaped to contain a radius that is intended to mimic a curvature of the patient's eyelid, so that the curved lid flipping end surface will contact and grasp an exterior surface of the patient's eyelid equally along the exterior surface; and
a computer control system configured to:
control the IR light source to direct the IR light to the exterior portion of the eyelid to IR trans-illuminate the meibomian glands in the eyelid;
control the imaging device to capture an image of the eyelid during IR trans-illumination, wherein the image of the eyelid is captured by the imaging device during IR trans-illumination while the eyelid is flipped;
receive the image of the eyelid;
store an IR trans-illumination image of meibomian glands in the eyelid from the received image of the eyelid in a non-transitory memory;
control the second IR light source to direct the second IR light to the interior portion of the interior surface of the eyelid to surface illuminate the interior surface of the eyelid, when not directing the IR light source to direct the IR light to the exterior portion of the eyelid;
control the imaging device to image, in a surface meibography image of the eyelid, the interior portion of the interior surface of the eyelid when the second IR light source is directed to direct the second IR light to the interior portion of the interior surface of the eyelid, wherein the image of the interior portion of the interior surface of the eyelid in the surface meibography image is captured by the imaging device while the eyelid is flipped;
receive the surface meibography image of the eyelid;
store a surface meibography image of meibomian glands in the eyelid from the received surface meibography image of the eyelid; and
subtract the IR trans-illumination image of meibomian glands from the surface meibography image of meibomian glands to generate a resultant image of meibomian glands.

17. The meibomian gland imaging system of claim 16, further comprising a wherein the lid flipping device comprising further comprises:
a body;
a curved lid flipping end surface disposed on an end of the body, the curved lid flipping end surface configured to grasp and flip the eyelid;
the IR light source disposed in the body and configured to generate the IR light under control of the computer control system; and
an elongated slot disposed in the curved lid flipping end surface of the body to receive the IR light from the IR light source to form an IR light pipe.

18. The meibomian gland imaging system of claim 17, wherein the computer control system is configured to:
control the IR light source to direct the IR light through the elongated slot in the lid flipping device to an exterior portion of an exterior surface of the eyelid, to IR trans-illuminate the meibomian glands in the eyelid when the curved lid flipping end surface of the lid flipping device is engaged with the eyelid to flip the eyelid; and
control the imaging device to image the interior portion of the interior surface of the eyelid during IR trans-illumination when the eyelid is flipped by the lid flipping device.

19. The meibomian gland imaging system of claim 17, wherein the IR light source comprises:
a central IR emitter disposed along a central portion of the elongated slot;
a first end IR emitter disposed adjacent to a first end of the elongated slot; and
a second end IR emitter disposed adjacent to a second end of the elongated slot;
each of the central IR emitter, the first end IR emitter, and the second end IR emitter are configured to independently emit the IR light under control of the computer control system.

20. The meibomian gland imaging system of claim 19, wherein the computer control system is further configured to provide a uniform or substantially uniform trans-illumination of meibomian glands by the IR light source along an outer surface of the flipped eyelid, wherein the computer control system is configured to adjust an intensity of the first end IR emitter and the second end IR emitter to be greater than an intensity of the central IR emitter to provide for the uniform or substantially uniform trans-illumination of the meibomian glands by the IR light source.

21. The meibomian gland imaging system of claim 16, wherein the imaging device is comprised of a high definition IR camera.

22. The meibomian gland imaging system of claim 16, further comprising a computer display, the computer control system further configured to display the IR trans-illumination image of meibomian glands in the eyelid on the computer display.

23. The meibomian gland imaging system of claim 16, wherein the computer control system is further configured to:
  direct the second IR light at a first angle to a first angle end of the interior portion of the eyelid while not directing the second IR light from a second angle, opposite the first angle, to the interior portion of the eyelid;
  direct the second IR light to the second angle, opposite the first angle, to a second angle end of the interior portion of the eyelid while not directing the second IR light from the first angle to the interior portion of the eyelid;
  image the interior portion of the interior surface of the eyelid with the imaging device when the interior portion is illuminated with the second IR light at the first angle to produce a first surface meibography image of meibomian glands in the eyelid;
  image the interior portion of the interior surface of the eyelid with the imaging device when the interior portion is illuminated with the second IR light at the second angle to produce a second surface meibography image of meibomian glands in the eyelid; and
  combine the second angle end of the first surface meibography image of meibomian glands with the first angle end of the second surface meibography image of meibomian glands to produce the surface meibography image of meibomian glands having reduced glare resulting from imaged reflections of the second IR light from the interior portion of the interior surface of the eyelid.

24. The meibomian gland imaging system of claim 23, wherein the second angle end of the first surface meibography image of meibomian glands only includes a portion of the first surface meibography image of meibomian glands that does not include glare from reflected IR light from a first IR light source, and the first angle end of the second surface meibography image of meibomian glands only includes a portion of the second surface meibography image of meibomian glands that does not include glare from the reflected second IR light.

* * * * *